US012746285B2

(12) United States Patent
Tiganis et al.

(10) Patent No.: US 12,746,285 B2
(45) Date of Patent: Sep. 29, 2026

(54) METHODS OF ACTIVATING CELLS VIA PTP 1B INHIBITION

(71) Applicants: Monash University, Clayton (AU); Peter MacCallum Cancer Institute, Melbourne (AU)

(72) Inventors: Tony Tiganis, Clayton (AU); Florian Wiede, Clayton (AU)

(73) Assignees: MONASH UNIVERSITY, Clayton (AU); PETER MACCALLUM CANCER INSTITUTE, Melbournd (AU)

(*) Notice: Subject to any disclaimer, the term of this patent is extended or adjusted under 35 U.S.C. 154(b) by 1095 days.

(21) Appl. No.: 17/058,551

(22) PCT Filed: May 31, 2019

(86) PCT No.: PCT/AU2019/050565
§ 371 (c)(1),
(2) Date: Nov. 24, 2020

(87) PCT Pub. No.: WO2019/227176
PCT Pub. Date: Dec. 5, 2019

(65) Prior Publication Data

US 2021/0207095 A1 Jul. 8, 2021

(30) Foreign Application Priority Data

Jun. 1, 2018 (AU) ................................ 2018901979

(51) Int. Cl.

| | |
|---|---|
| ***A61P 35/00*** | (2006.01) |
| ***A61K 31/56*** | (2006.01) |
| ***A61K 31/575*** | (2006.01) |
| ***A61K 40/11*** | (2025.01) |
| ***A61K 40/31*** | (2025.01) |
| ***A61K 40/42*** | (2025.01) |
| ***A61P 35/02*** | (2006.01) |
| ***A61P 35/04*** | (2006.01) |

(52) U.S. Cl.
CPC .............. *A61K 40/31* (2025.01); *A61K 31/56* (2013.01); *A61K 31/575* (2013.01); *A61K 40/11* (2025.01); *A61K 40/4205* (2025.01); *A61P 35/00* (2018.01); *A61K 2239/31* (2023.05); *A61K 2239/38* (2023.05); *C12N 2310/14* (2013.01); *C12N 2310/141* (2013.01); *C12N 2310/531* (2013.01); *C12N 2501/73* (2013.01)

(58) Field of Classification Search
CPC ...... A61K 31/575; A61K 40/31; A61K 31/56; A61K 40/11; A61K 40/4205; A61K 40/42; A61P 35/00; A61P 35/02; A61P 35/04
See application file for complete search history.

(56) References Cited

U.S. PATENT DOCUMENTS

2015/0283178 A1* 10/2015 June .................... A61K 39/3955 424/85.2
2023/0355670 A1* 11/2023 Tiganis .................. A61K 40/42

FOREIGN PATENT DOCUMENTS

| | | | |
|---|---|---|---|
| WO | WO-9744044 A1 * | 11/1997 | ........... A61K 31/575 |
| WO | 2004/016735 | 2/2004 | |
| WO | 2006016741 A1 | 12/2006 | |
| WO | 2008/043181 | 4/2008 | |
| WO | 2009/033293 | 3/2009 | |
| WO | 2009100254 A2 | 8/2009 | |
| WO | 2015/188228 | 12/2015 | |
| WO | 2019036815 A1 | 2/2019 | |
| WO | 2019/178422 | 9/2019 | |
| WO | 2019/246513 A1 | 12/2019 | |

OTHER PUBLICATIONS

Le Sommer et al., Protein Tyrosine Phosphatase 1B (PTP1B) in the immune system, Inflamm. Cell Signal. 2:e965, doi: 10.14800/ics.965, 10 pages, 2015.*
He et al., Protein tyrosine phosphatases as potential therapeutic targets, Acta Pharmacol. Sinica, 35:1227-1246, doi: 10.1038/aps.2014.80;, 2014.*
Antunes et al. (Bioengineering (2022), 9(4), 166. https://doi.org/10.3390/bioengineering9040166). (Year: 2022).*
Bourebaba et al. (Front Endocrinol (Lausanne). Mar. 20, 2023; 14:1149610. doi: 10.3389/fendo.2023.1149610. PMID: 37020593; PMCID: PMC10067883). (Year: 2023).*
Tang et al. (Front. Pharmacol. (2024), 15:1466017. doi: 10.3389/fphar.2024.1466017). (Year: 2024).*
Chalak et al. (Life (2024), 14, 417. https://doi.org/10.3390/life14030417). (Year: 2024).*
Altea-Manzano et al. (EMBO Reports (2020) 21: e50635. DOI 10.15252/embr.202050635). (Year: 2020).*
Lantz et al. (Obesity (Silver Spring). Aug. 2010;18(8):1516-23. doi: 10.1038/oby.2009.444. Epub Jan. 14, 2010. PMID: 20075852). (Year: 2010).*
Blanquart et al. (2009) "Implication of protein tyrosine phosphatase 1B in MCF07 cell proliferation and resistance to 4-OH tamoxifen." Biochemical and Biophysical Research Communications 387: 748-753.

(Continued)

*Primary Examiner* — James H Alstrum-Acevedo
*Assistant Examiner* — Chris E Simmons
(74) *Attorney, Agent, or Firm* — McDonnell Boehnen Hulbert & Berghoff, LLP

(57) ABSTRACT

The present invention generally relates to methods of activating cells for use in therapy. For example, the invention relates to preparing cells ex vivo for use in immunotherapy, particularly cancer immunotherapy. More specifically, the invention relates to methods for the preparation of leukocytes, particularly T cells through PTP1B inhibition, exhibiting cytotoxic properties for use in adoptive cell transfer. The invention also relates to cells and compositions including them for cancer immunotherapy. The invention also relates to methods of immunotherapy, particularly cancer immunotherapy.

7 Claims, 48 Drawing Sheets

Specification includes a Sequence Listing.

(56) References Cited

OTHER PUBLICATIONS

Penafuerte et al. (2017) "Downregulation of PTP1B and TC-PTP phosphatases potentiate dendritic cell-based immunotherpay through IL-12/IFYgamma signaling." Oncoimmunology 6:6, e1321185.
Bence et al. (2006) "Neuronal PTP1B regulates body weight, adiposity and leptin action," Nature Medicine. 12, 917-24.
Blanquart, C. et al., "Implication of protein tyrosine phosphatase 1B in MCF-7 cell proliferation and resistance to 4-OH tamoxifen", Biochemical and Biophysical Research Communications, 2009, vol. 387, No. 4, pp. 748-753.
Dube, N. et al., "Involvement of the small protein tyrosine phosphatases TC-PTP and PTP1B in signal transduction and diseases: From diabetes, obesity to cell cycle, and cancer", Biochimerica et Biophysica Acta, 2005, vol. 1754, No. 1-2, pp. 108-117.
Stuible, M. et al., "PTP1B and TC-PTP: regulators of transformation and tumorigenesis", Cancer Metastasis Rev, 2008, vol. 27, No. 2, pp. 215-230.
The International Search Report and Written Opinion, Application No. PCT/AU2019/050565, mailed Aug. 2, 2019, 13 pages.
Chang, Ya-Fang, Hui-Yen Chuang, Chien-Hui Hsu, Ren-Shyan Liu, Sanjiv Sam Gambhir, and Jeng-Jong Hwang. "Immunomodulation of curcumin on adoptive therapy with T cell functional imaging in mice." Cancer Prevention Research 5, No. 3 (2012): 444-452.
Bhattacharyya, Sankar, Dewan Md Sakib Hossain, Suchismita Mohanty, Gouri Sankar Sen, Sreya Chattopadhyay, Shuvomoy Banerjee, Juni Chakraborty et al. "Curcumin reverses T cell-mediated adaptive immune dysfunctions in tumor-bearing hosts." Cellular & molecular immunology 7, No. 4 (2010): 306-315.
Kostrzewa, Tomasz, Paulina Przychodzen, Magdalena Gorska-Ponikowska, and Alicja Kuban-Jankowska. "Curcumin and cinnamaldehyde as PTP1B inhibitors with antidiabetic and anticancer potential." Anticancer research 39, No. 2 (2019): 745-749.
Perez-Quintero L.A. et al. (2019) 'Abstract B035: Enhancing antitumoral activity of cell-based immunotherapies by modulating the JAK-STAT axis', Cancer Immunology Research, 7(2_Supplement), pp. B035-B035.
Heinonen KM et al., 'Protein tyrosine phosphatases PTP-1B and TC-PTP play nonredundant roles in macrophage development and IFN-gamma signaling', Proc Natl Acad Sci U S A. Jun. 9, 2009;106(23):9368-72.
Krishnan et al. (2014) "Targeting the disordered C terminus of PTP1B with an allosteric inhibitor", Nat Chem Biol, Jul. 10(7):558-66. doi: 10.1038/nchembio.1528.
Li et al. (2010) "Curcumin inhibits hepatic protein-tyrosine phosphatase 1B and prevents hypertriglyceridemia and hepatic steatosis in fructose-fed rats", Hepatology, May 51(5):1555-66. doi: 10.1002/hep.23524.
Li et al. (2016) "The design strategy of selective PTP1B inhibitors over TCPTP", Bioorg Med Chem, Aug. 15;24(16):3343-52. doi: 10.1016/j.bmc.2016.06.035.
Manjunath et al. (2013) "Newer gene editing technologies toward HIV gene therapy", Viruses, Nov. 14;5(11):2748-66. doi: 10.3390/v5112748.
Provasi et al. (2012) "Editing T cell specificity towards leukemia by zinc finger nucleases and lentiviral gene transfer", Nat Med, May 18(5):807-815. doi: 10.1038/nm.2700.
Schumacher and Schreiber (2015) "Neoantigens in cancer immunotherapy", Science, Apr. 3;348(6230):69-74. doi: 10.1126/science.aaa4971.

* cited by examiner

A

C

D

D

C

D

A

B

C

A

METHODS OF ACTIVATING CELLS VIA PTP 1B INHIBITION

CROSS REFERENCE TO RELATED APPLICATION

This application is a U.S. national phase of International Application No. PCT/AU2019/050565, filed May 31, 2019, which claims priority to Australian Patent Application No. 2018901979, filed Jun. 1, 2018, both of which are incorporated by reference herein in their entirety.

FIELD OF THE INVENTION

The present invention generally relates to methods of activating cells for use in therapy. For example, the invention relates to preparing cells ex vivo for use in immunotherapy, particularly cancer immunotherapy. More specifically, the invention relates to methods for the preparation of leukocytes, particularly T cells, exhibiting cytotoxic properties for use in adoptive cell transfer. The invention also relates to cells and compositions including them for cancer immunotherapy. The invention also relates to methods of immunotherapy, particularly cancer immunotherapy.

SEQUENCE LISTING STATEMENT

A computer readable form of the Sequence Listing is filed with this application by electronic submission and is incorporated into this application by reference in its entirety. The Sequence Listing is contained in the file created on Jun. 2, 2026, having the file name "20-1828-PCT-US_ST25.txt" and is 3,556 bytes in size.

ASSOCIATED APPLICATION

The present application claims priority from Australian provisional application AU 2018901979, the contents and disclosure of which are hereby incorporated by reference in their entirety.

BACKGROUND OF THE INVENTION

Immunotherapy is the use of the immune system of a patient to reject a disease, such as cancer or viral infection, by stimulating the patient's immune system to attack the malignant tumour or virally infected cells (and spare the normal cells of the patient). One mode of immunotherapy employs immunization of the patient (e.g., by administering a cancer vaccine) to train the patient's immune system to recognize and destroy tumour cells. Another approach uses the administration of therapeutic antibodies, thereby recruiting the patient's immune system to destroy tumour cells. Cell-based immunotherapy is another approach, which involves immune cells such as the Natural killer Cells (NK cells), Lymphokine Activated killer cell (LAK), Cytotoxic T Lymphocytes (CTLs), Dendritic Cells (DC), etc.

Many kinds of tumour cells or viral infected cells are tolerated by the patient's own immune system, as they are the patient's own cells (e.g., they are self) and are not effectively recognised by the patient's immune system allowing the tumour or viral infected cells to grow and divide without proper regulatory control. In addition, tumour-specific T cells are normally tolerized so that they do not respond to tumour activity. Accordingly, the patient's own immune system requires stimulation to attack the diseased cells.

Adoptive cell transfer (ACT) is an effective form of immunotherapy and involves the transfer of immune cells with anti-tumour or anti-viral activity into patients. ACT is a treatment approach that typically involves the identification of lymphocytes with anti-tumour or anti-viral activity, the in vitro expansion of these cells to large numbers and their infusion into the disease bearing host.

Adoptive T cell therapy depends on the ability to optimally select or genetically engineer cells with targeted antigen specificity and then induce the T cells to proliferate while preserving their effector function and engraftment and homing abilities. However, clinical trials have been carried out with adoptively transferred cells that were cultured in what are now understood to be suboptimal conditions that impair the essential functions of T cells such as antigen specific cytotoxic activity.

The methods which are currently used to prepare cells for use in adoptive cell therapy are limited in that they provide cells that have less than the expected cell killing of target cells, such as tumour cells. There is therefore a need for new or improved methods and/or compositions for adoptive cell therapy or for preparing cells for use in adoptive cell therapy.

There is also a separate need for new or improved methods and/or compositions for stimulating the immune system for the treatment of cancer.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

The present invention relates to a method for producing a leukocyte that has an enhanced capacity for killing a target cell, the method comprising contacting the leukocyte with a PTP1B inhibitor in conditions for enabling the inhibitor to inactivate PTP1B in the leukocyte, thereby producing a leukocyte that has an enhanced capacity for killing a target cell.

The present invention relates to a method for producing a leukocyte cell that has an enhanced capacity for killing a target cell, the method comprising contacting the leukocyte ex vivo with a PTP1B inhibitor for a sufficient time and under conditions for inactivation of PTP1B in the leukocyte, thereby producing a leukocyte cell that has an enhanced capacity for killing a target cell.

The present invention relates to a method for preparing an ex vivo population of T cells exhibiting at least one property of a cytotoxic T cell comprising culturing T cells in the presence of a PTP1B inhibitor.

The present invention relates to a method for preparing an ex vivo population of T cells exhibiting at least one property of a cytotoxic T cell comprising the steps of:

culturing a T cell population from a biological sample in the presence of a PTP1B inhibitor;

expanding the cells in culture;

thereby preparing an ex vivo population of T cells exhibiting cytotoxic properties. Preferably the biological sample is derived from a subject having a cancer or have been conditioned or engineered to have specificity for a cancer.

The present invention relates to an ex vivo method for preparing a composition comprising antigen-specific cytotoxic T cells, the method comprising:

providing a biological sample containing a population of T cells;

co-culturing antigenic material with the T cell population in the presence of a PTP1B inhibitor; and expanding the cells in culture, thereby preparing a composition comprising antigen-specific cytotoxic T cells ex vivo.

The present invention relates to a method for expanding a population of leukocytes, the method comprising contacting a population of leukocytes with a PTP1B inhibitor in conditions for enabling the inhibitor to inactivate PTP1B in the leukocytes, thereby expanding the population of leukocytes. The leukocytes may comprise T cell or B cells. Preferably, the leukocytes comprise T cells including CD4+ and CD8+ T cells. The T cells may also include effector and effector memory T cells and/or central memory T cells. The T cells may also be genetically engineered to express anti-tumour T cell receptors or chimeric antigen receptors (CARs), or may be γδ T cells. The leukocytes may also comprise tumour infiltrating lymphocytes, peripheral blood lymphocyte, or be enriched with mixed lymphocyte tumour cell cultures (MLTCs) or cloned using autologous antigen presenting cells and tumour derived peptides. The lymphocytes may be isolated from a histocompatible donor, or from a cancer-bearing subject.

The present invention relates to a method for increasing the level of T cells in a subject exhibiting an effector memory phenotype comprising the steps of:

culturing a T cell population from a biological sample ex vivo in the presence of a PTP1B inhibitor;

expanding the cells in culture;

administering the cultured cells to the subject;

thereby increasing the level of T cells in a subject exhibiting an effector memory phenotype.

The present invention also provides a method for forming an immune response in a subject suitable for the treatment of cancer comprising the steps of obtaining T cells from the subject or a histocompatible donor subject;

culturing the T cells in the presence of a PTP1B inhibitor ex vivo for a sufficient time and under conditions for to generate a population of T cells exhibiting at least one cytotoxic T cell property, thereby forming a population of cytotoxic T cells, administering the population of cytotoxic T cells to the subject, thereby producing an immune response in a subject suitable for the treatment of cancer.

The present invention also relates to a method of increasing CD8+ T cell mediated immunity in a subject having a disease state comprising:

contacting CD8+ T cells with a PTP1B inhibitor ex vivo for a sufficient time and under conditions to generate a population of CD8+ T cells exhibiting at least one property of a cytotoxic T cell;

administering the population of CD8+ T cells to the subject, thereby increasing CD8+ T cell mediated immunity in a subject.

The present invention also relates to a method of increasing CD8+ T cell mediated immunity in a subject having a disease state comprising:

isolating a population of the subject's CD8+ T cells;

introducing a nucleic acid molecule encoding an siRNA, shRNA or gRNA directed to PTP1B into the isolated CD8+ T cells, thereby reducing the level of PTP1B in a CD8+ T cell; and reintroducing the CD8+ T cells into said subject, thereby increasing the CD8+ T cell mediated immunity in a subject.

The present invention relates to a method of promoting regression of a cancer in a subject comprising the steps of:

culturing T cells obtained from a subject in the presence of a PTP1B inhibitor, administering the cultured T cells to the subject, whereupon regression of the cancer is promoted.

The present invention relates to a method of promoting regression of a cancer in a subject having cancer comprising the steps of:

culturing CAR-T cells specific for a tumour antigen expressed by the cancer in the presence of a PTP1B inhibitor, administering the cultured CAR-T cells to the subject, whereupon regression of the cancer is promoted.

The present invention relates to a method of prolonging survival of a subject having cancer comprising the steps of:

culturing CAR-T cells specific for a tumour antigen expressed by the cancer in the presence of a PTP1B inhibitor, administering the cultured CAR-T cells to the subject, whereupon survival of the subject is prolonged.

In some examples of the above embodiments, the cancer is a Her-2 positive cancer and the CAR-T cell is specific for Her-2, however it will be appreciated that the method is not limited to the type of tumour antigen expressed by the cancer. (In other examples, the cancer is positive for the tumour antigens CD171, EGFR, MSLN, CD19, CD123, Lewis Y, FAP, CD22, GD2, or CD131 and the CAR-T cell is specific for any one or more of those antigens.)

In any method of the invention, the T cells do not require exposure to a cytokine (such as IL-2, IL-15 or IL-17) prior to being administered to a subject. Alternatively, the individual to whom the T cells are being administered, does not require concomitant administration of a cytokine for enhancing proliferation of the T cells (such as IL-2, IL-15 or IL-17).

The present invention also relates to tumour antigen-specific cytotoxic T cells for use in adoptive immunotherapy comprising an exogenous nucleic acid coding an interfering RNA, for example a microRNA, shRNA, siRNA, or gRNA molecule that can reduce the level of PTP1B in a cell.

The present invention relates to an isolated, purified or recombinant cell comprising an antigen-specific T cell receptor and an exogenous nucleic acid encoding an interfering RNA, for example a microRNA, shRNA, siRNA or gRNA molecule that can reduce the level of PTP1B in a cell. Preferably, the TCR is specific for a cancer antigen and the cell is a CD8+ T cell. The CD8+ T cell may be a tumour infiltrating lymphocyte or a peripheral blood lymphocyte isolated from a host afflicted with cancer.

The present invention relates to a method of treating cancer in a subject comprising administering a population of isolated or purified CD8+ T cells effective to treat the cancer, the CD8+ T cell comprising an antigen-specific T cell receptor and an exogenous nucleic acid encoding an interfering RNA, for example a microRNA, shRNA, siRNA or gRNA molecule directed to PTP1B.

The present invention also provides a method for proliferating, enriching or expanding a composition of cells comprising a CD8+ T cell, the method comprising culturing a composition of cells in a medium, the medium comprising a PTP1B inhibitor, wherein the PTP1B inhibitor is provided in the medium to permit contact with a CD8+ T cell during culture. Preferably the proliferating, enriching or expanding will result in a doubling of the number of CD8+ T cells that exhibit at least one cytotoxic T cell property. More preferably the cell expansion result in 3× or 4× number of CD8+ T cells that exhibit at least one cytotoxic T cell property. The expansion of CD8+ T cells may be 5×, 6×, 7×, 8×, 9× or over 10×. The method may also increase the relative number of CD8+ T cells in the composition that exhibit at least one cytotoxic T cell property.

The present invention also relates to a composition of cytotoxic cells wherein greater than 20% of the cells have complete or partial inhibition of PTP1B. Preferably, the composition includes greater than 30%, 40%, 50%, 60%, 70%, 80%, 85%, 90%, 91%, 92%, 93%, 94%, 95%, 96%, 97%, 98 or 99% of cells that have complete or partial inhibition of PTP1B. In one embodiment, all cells have complete or partial inhibition of PTP1B.

The present invention also relates to a composition comprising a leukocyte and a PTP1B inhibitor as described herein. Preferably, the PTP1B inhibitor is an interfering RNA as described herein or the small molecule inhibitor, claramine, trodusquemine, derivatives thereof (including DPM-1001) or any other small molecule inhibitor described herein. The composition may further include a cytokine for enhancing cell killing, such as IL-2 or IFNγ. Preferably, the leukocyte is a CAR T cell, more preferably the CAR T cell is specific for a cell surface tumour antigen. In one example, the CAR-T cell is specific for Her-2, however it will be appreciated that the method is not limited to the type of tumour antigen expressed by the cancer. In other examples, the CAR-T cell is specific for one or more tumour antigens including but not limited to CD171, EGFR, MSLN, CD19, CD123, Lewis Y, FAP or CD131 or any other tumour antigen.

The T cells may be selected from the group consisting of tumour infiltrating lymphocytes, peripheral blood lymphocyte, genetically engineered to express anti-tumour T cell receptors or chimeric antigen receptors (CARs), γδ T cells, enriched with mixed lymphocyte tumour cell cultures (MLTCs) or cloned using autologous antigen presenting cells and tumour derived peptides. The lymphocytes may be isolated from a histocompatible donor, or from the cancer-bearing subject.

In any method of the invention, the leukocytes or T cells are purified or substantially purified prior to culture in the presence of a PTP1B inhibitor. This step enriches the leukocytes or T cells by removing other cell types from the biological sample.

In one embodiment, the CAR-T cells are Her-2 specific CAR CD8+ T cells. In alternative embodiments the CAR-T cells are CD19-specific CAR CD8+ T cells, or are CD171-specific CAR CD8+ T cells, or EGFR-specific CAR CD8+ T cells, or CD22-specific CAR CD8+ T cells, or CD123-specific CAR CD8+ T cells, or Lewis Y specific CAR CD8+ T cells, or MSLN-specific CAR CD8+ T cells, or FAP-specific CAR CD8+ T cells, or CD131-specific CAR CD8+ T cells etc. The T cells may be a population that includes more than one type of T cells, comprising any one or more types described herein. For example, the population of T cells may include naïve, activated and/or memory T cells.

The present invention relates to a method for increasing the level of T cells in a subject exhibiting an effector memory phenotype comprising the steps of:

administering a PTP1B inhibitor to the subject;

thereby increasing the level of T cells in a subject exhibiting an effector memory phenotype.

The present invention also provides a method for forming an immune response in a subject suitable for the treatment of cancer comprising the steps of administering a PTP1B inhibitor to the subject;

thereby producing an immune response in a subject suitable for the treatment of cancer.

The present invention also relates to a method of increasing CD8+ T cell mediated immunity in a subject having a disease state comprising:

administering a PTP1B inhibitor to the subject;

thereby increasing CD8+ T cell mediated immunity in a subject.

The present invention also relates to a method of treating cancer in a subject comprising:

administering a PTP1B inhibitor to the subject;

thereby treating cancer in the subject.

The present invention also relates to a method of activating exhausted tumour infiltrating lymphocytes in a subject suffering from cancer, comprising:

administering a PTP1B inhibitor to the subject;

thereby activating the tumour infiltrating lymphocytes in the subject.

The present invention relates to a method of promoting regression of a cancer in a subject having cancer comprising the steps of:

administering a PTP1B inhibitor to the subject;

whereupon regression of the cancer is promoted.

In some embodiments, the cancer is a Her-2 positive cancer. Alternatively, the cancer may be a CD19 positive cancer, a CD171 positive cancer, an EGFR-positive cancer, a CD22-positive cancer, a CD123-positive cancer, a Lewis Y positive cancer cells, or an MSLN-positive cancer, an FAP-positive cancer, or CD131-positive cancer. It will be appreciated however that the present invention is not limited by the type of cancer requiring treatment.

The present invention relates to a method of prolonging survival of a subject having cancer comprising the steps of:

administering a PTP1B inhibitor to the subject;

whereupon survival of the subject is prolonged. Preferably, the cancer is a Her-2 positive cancer.

In any of the above methods, the methods may further include administration of a CAR T cell to the individual. The CAR-T cell may be a Her-2 specific CAR CD8+ T cell.

In other examples, the CAR-T cell is specific for one or more tumour antigens including but not limited to CD171, EGFR, MSLN, CD19, CD123, Lewis Y, FAP or CD131 or any other tumour antigen.

Accordingly, the present invention also relates to a method of treating cancer in a subject comprising:

providing a subject who has received a CAR-T cell for the treatment of cancer, administering a PTP1B inhibitor to the subject;

thereby treating cancer in the subject.

Further, the present invention relates to a method of enhancing a CAR-T therapy for cancer in a subject, the method comprising:

providing a subject who has received a CAR-T cell for the treatment of cancer, administering a PTP1B inhibitor to the subject, thereby enhancing the CAR-T therapy for cancer in the subject.

The present invention also provides use of a PTP1B inhibitor in the manufacture of a medicament for:

increasing the level of T cells in a subject exhibiting an effector memory phenotype;

forming an immune response in a subject suitable for the treatment of cancer;

increasing CD8+ T cell mediated immunity in a subject having a disease state;

treating cancer in a subject;

promoting regression of a cancer in a subject having cancer; or prolonging survival of a subject having cancer.

The medicament may further include CAR-T cells. Preferably the CAR-T cells are Her-2 specific CAR CD8+ T cells. In other examples, the CAR-T cell is specific for one or more tumour antigens including but not limited to CD171, EGFR, MSLN, CD19, CD123, Lewis Y, FAP or CD131 or any other tumour antigen.

The present invention also provides a PTP1B inhibitor or pharmaceutical composition comprising a PTP1B inhibitor for use in:

increasing the level of T cells in a subject exhibiting an effector memory phenotype;

forming an immune response in a subject suitable for the treatment of cancer;

increasing CD8+ T cell mediated immunity in a subject having a disease state;

treating cancer in a subject;

promoting regression of a cancer in a subject having cancer; or prolonging survival of a subject having cancer.

The above use may be in combination with the administration of CAR-T cells to an individual requiring treatment. The CAR-T cells may be, but are not limited to Her-2 specific CAR CD8+ T cells.

In any aspect of the present invention, the PTP1B inhibitor may be administered directly to an individual. The route of administration may be systemic or any route as described herein that allows the PTP1B inhibitor to enter the circulation. It will be appreciated that administration of a PTP1B inhibitor directly to an individual can be used to activate otherwise exhausted tumour infiltrating lymphocytes.

As used herein, a PTP1B inhibitor may be any molecule that inhibits the phosphatase activity of PTP1B. The inhibitor may be a direct inhibitor of the phosphatase active site, may act allosterically to inhibit phosphatase activity, inhibit interaction of PTP1B with its substrate, or may reduce the level of PTP1B by reducing the transcriptional activity of the PTP1B gene, or reducing the amount of PTP1B mRNA or protein present in the cell.

The PTP1B inhibitor may specifically bind to and directly inhibit PTP1B such that the off-target effects of the PTP1B are minimal. Preferably, PTP1B inhibitor inhibits or reduces activity or expression of another target by no more than about 5%, no more than about 10%, no more than about 15%, or no more than about 20%. Preferably, the PTP1B inhibitor inhibits or reduces the activity of PTP1B by at least 50%, at least 60%, at least 70%, at least 80%, at least 90% or more. In certain embodiments, the inhibitor completely inhibits or prevents activity of PTP1B.

Typically, the inhibitor is a small molecule, for example claramine, trodusquemine (or the derivative DPM-1001) or any other small molecule inhibitor as described herein, or a peptide, or a peptidomimetic. The inhibitor may also be an inhibitory or interfering RNA, such as antisense RNA, siRNA, microRNA or shRNA.

In further embodiments, the inhibitor is a gRNA (including an sgRNA) for CRISPR-based genome editing that results in partial or complete reduction of ptp1b expression or partial or complete reduction of PTP1B activity. Although gRNAs are typically used with genome editing systems such as CRISPR-Cas9, it will be understood that other genome editing approaches that make use of gRNA can also be used (e.g., Cpf1 or CRISPR-Cas12a)

In any aspect of the invention, the only inhibition is of PTP1B. In other words, no other gene or gene product other than PTP1B is inhibited. For example, the only small molecule inhibitor used is a PTP1B inhibitor or the only miRNA, shRNA, siRNA or gRNA used targets PTP1B, or the only genome editing occurs to the PTP1B gene.

In any aspect of the invention, the only phosphatase inhibited is PTP1B. In other words, no other phosphatase is inhibited. For example, the PTP1B inhibitor does not inhibit another phosphatase.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

$$\frac{(Nr.HER2/Nr.LML)4\text{ hours}}{(Nr.HER2/Nr.LML)\text{No CAR}-T}.$$

PTP1B-deficient $CD8^+$ central/memory or effector/memory CAR T cells significantly reduced the Viability Index of Target cells in comparison with their wild-type counterpart (p<0.0001, p<0.0001). B) PTP1B-deficiency leads to increased effector/memory (p=0.0079) and reduced central/memory (p=0.0079) CAR T cell numbers. C) The activation markers CD25, Lag3, and PD-1 were significantly increased in PTP1B-deficient CAR T cells (p=0.0159, p=0.0079, p=0.0079). Expression of the cytotoxic markers granzyme B and interferon gamma were increased (p=0.0159, p=0.0159). Results shown are means±SEM and are representative of two independent experiments. Significances were determined using 2-way ANOVA test for the assessment of CAR T cell cytotoxicity and 2-tailed Mann-Whitney U test for CAR T cell phenotyping.

Figure 14:
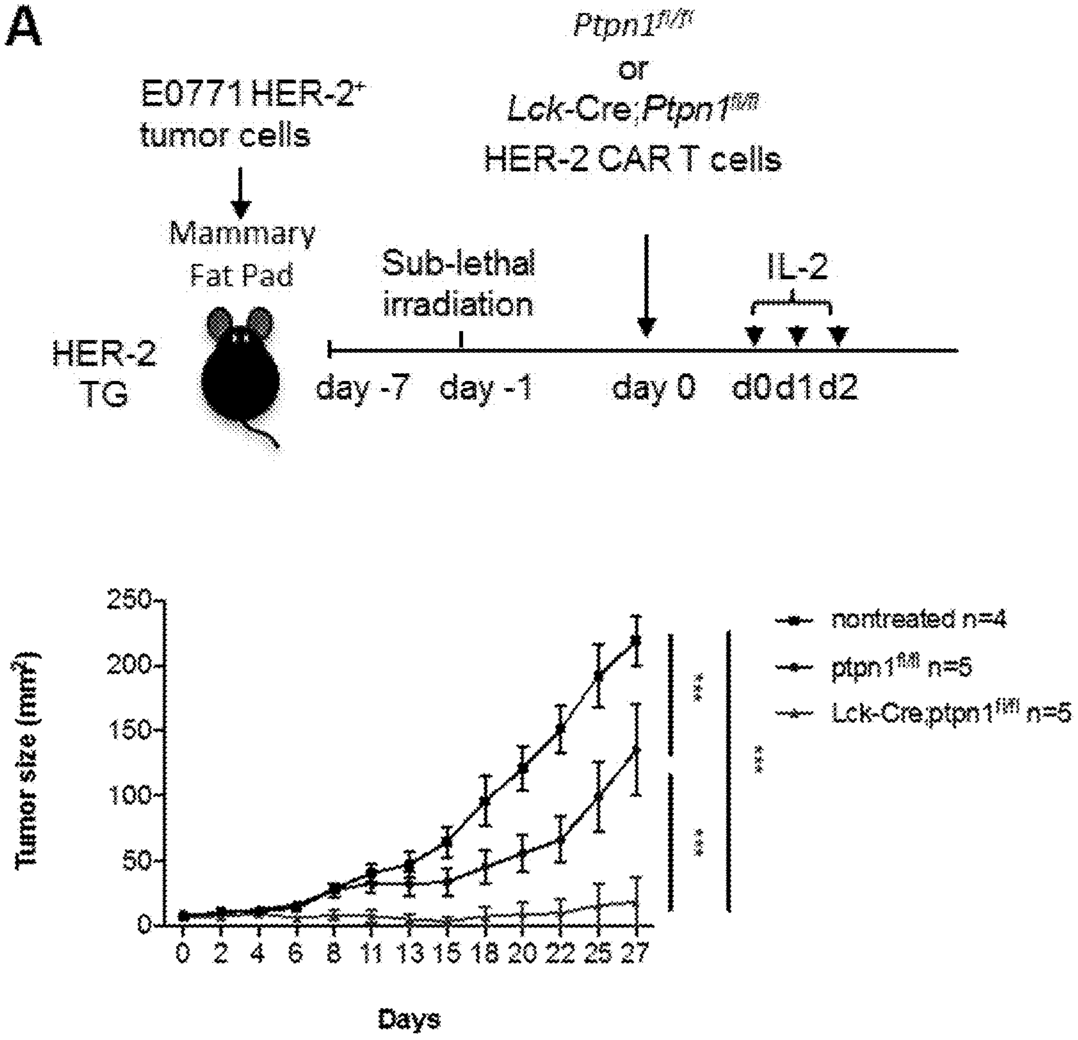
Figure 14:
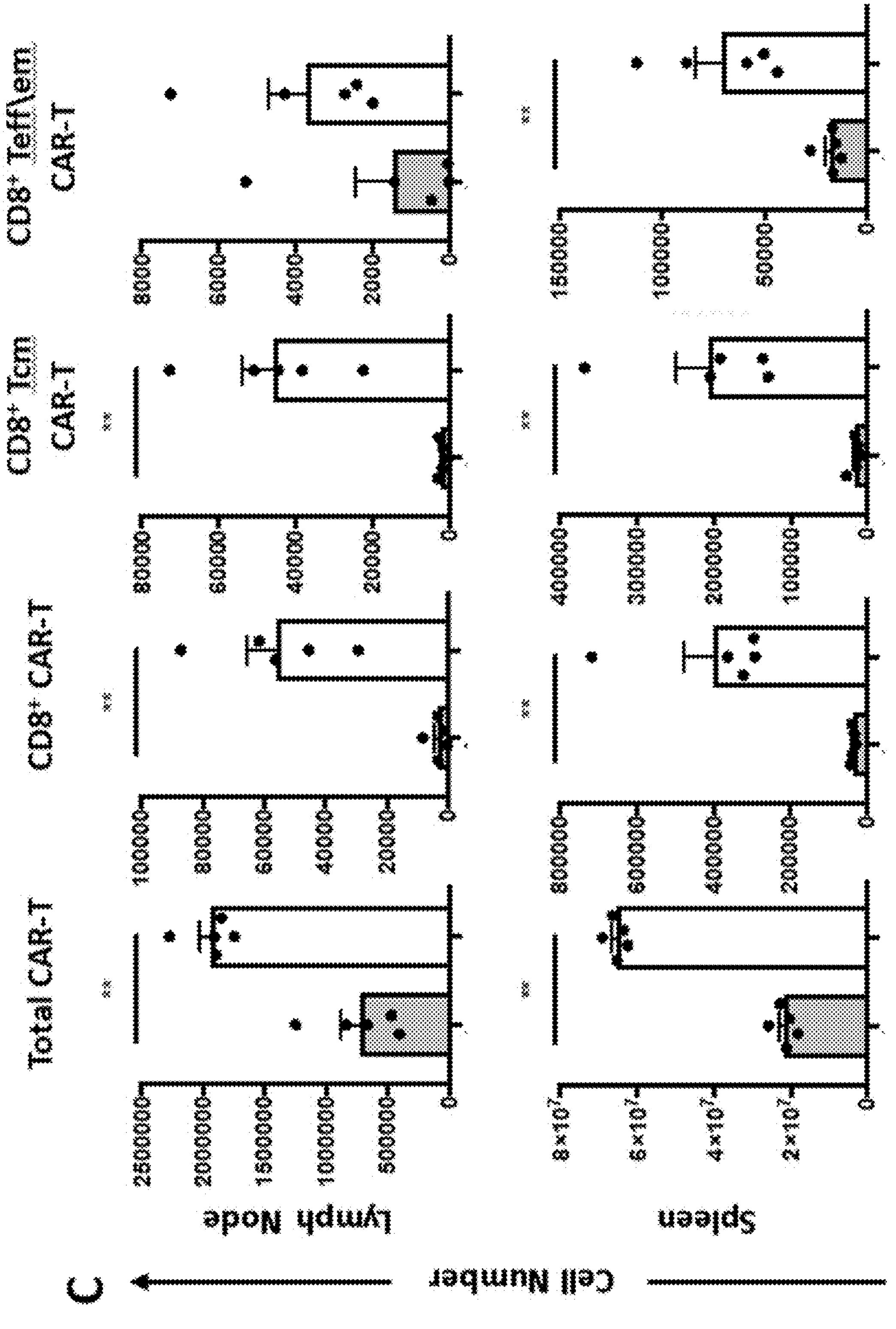
Figure 14:
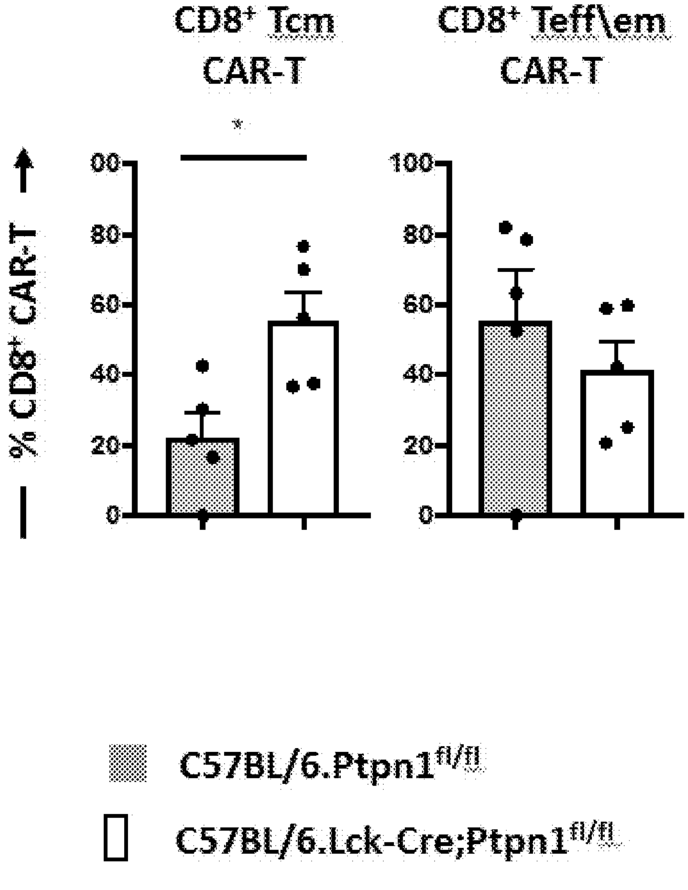

FIG. 14. PTP1B-deficiency augments CAR T cell mediated tumor suppression in vivo. A) $2\times10^5$ HER-2 expressing E0771 cells (E0771:HER-2) were inoculated into the fourth inguinal mammary fat pads of HER-2 transgenic mice. Seven days post tumour injection HER-2 transgenic mice received total body irradiation (4 Gy) followed by the adoptive transfer of $1\times10^7$ CAR T cells (i.v.) together with the co-administration of $2.5\times10^5$ IU human IL-2 (i.p). Tumor growth was monitored and CAR T cells were isolated from draining lymph nodes and spleens at the end point of tumor growth 28 days post tumor inoculation. B) PTP1B-deficient CAR T cells significantly enhanced the suppression of tumor growth (p<0.0001, p<0.0001, p<0.0001). C) PTP1B-deficient total CAR T cells, $CD8^+$ CAR T cells, $CD8^+$ CAR T central/memory and effector/memory cells were significantly increased in the draining lymph nodes (p=0.0079, p=0.0079, p=0.0079) and spleens (p=0.0079, p=0.0079, p=0.0079, p=0.0079) of HER-2 transgenic mice. D) Circulating PTP1B-deficient central/memory $CD8^+$ CAR T cells were increased (p=0.0317) while effector/memory $CD8^+$ CAR T cells showed no differences (p=0.3095). Results shown are means±SEM. Significances were determined using 2-way ANOVA for the assessment of tumor growth and 2-tailed Mann-Whitney U test for CAR T cell phenotyping.

Figure 15:
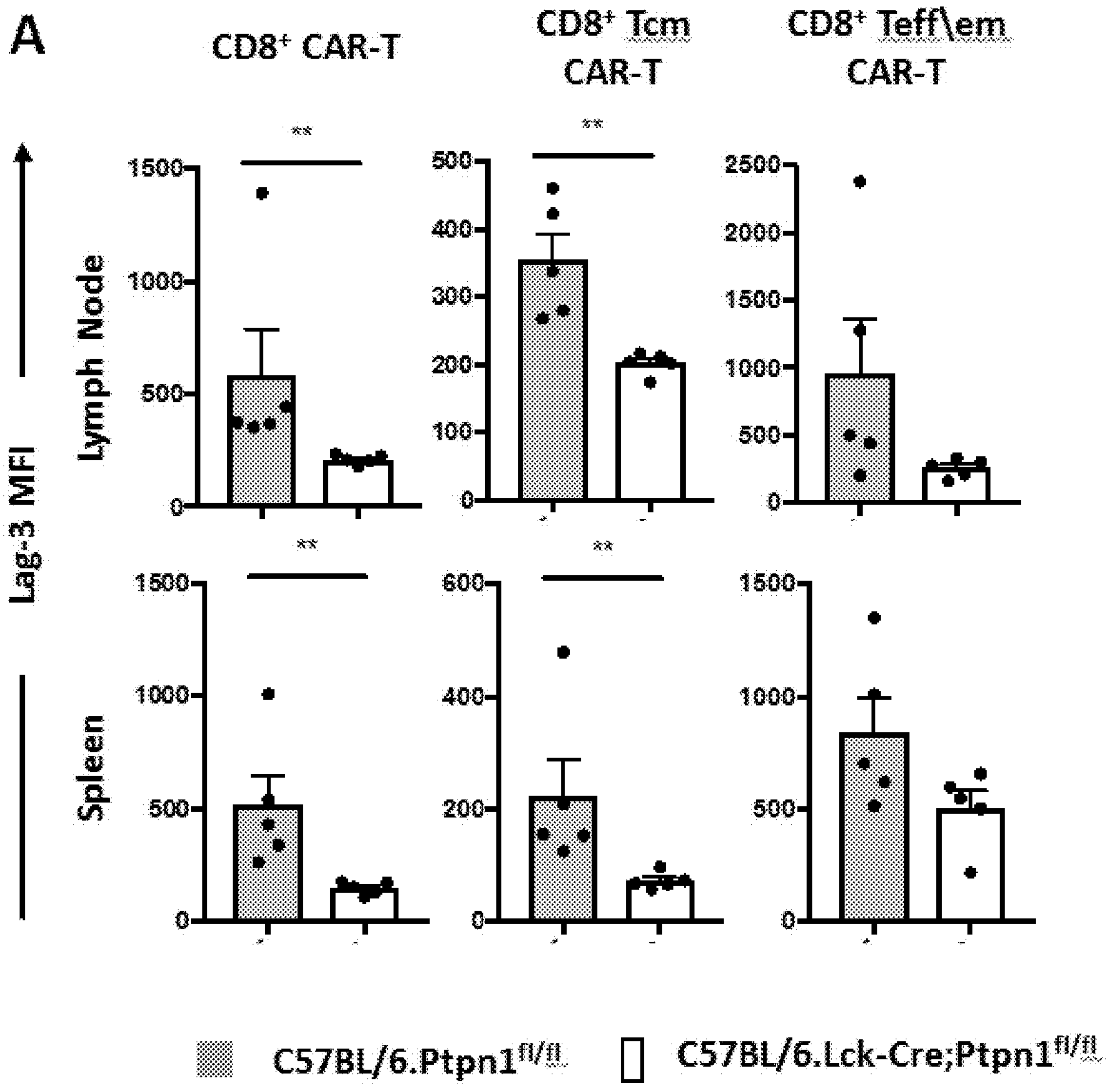
Figure 15:
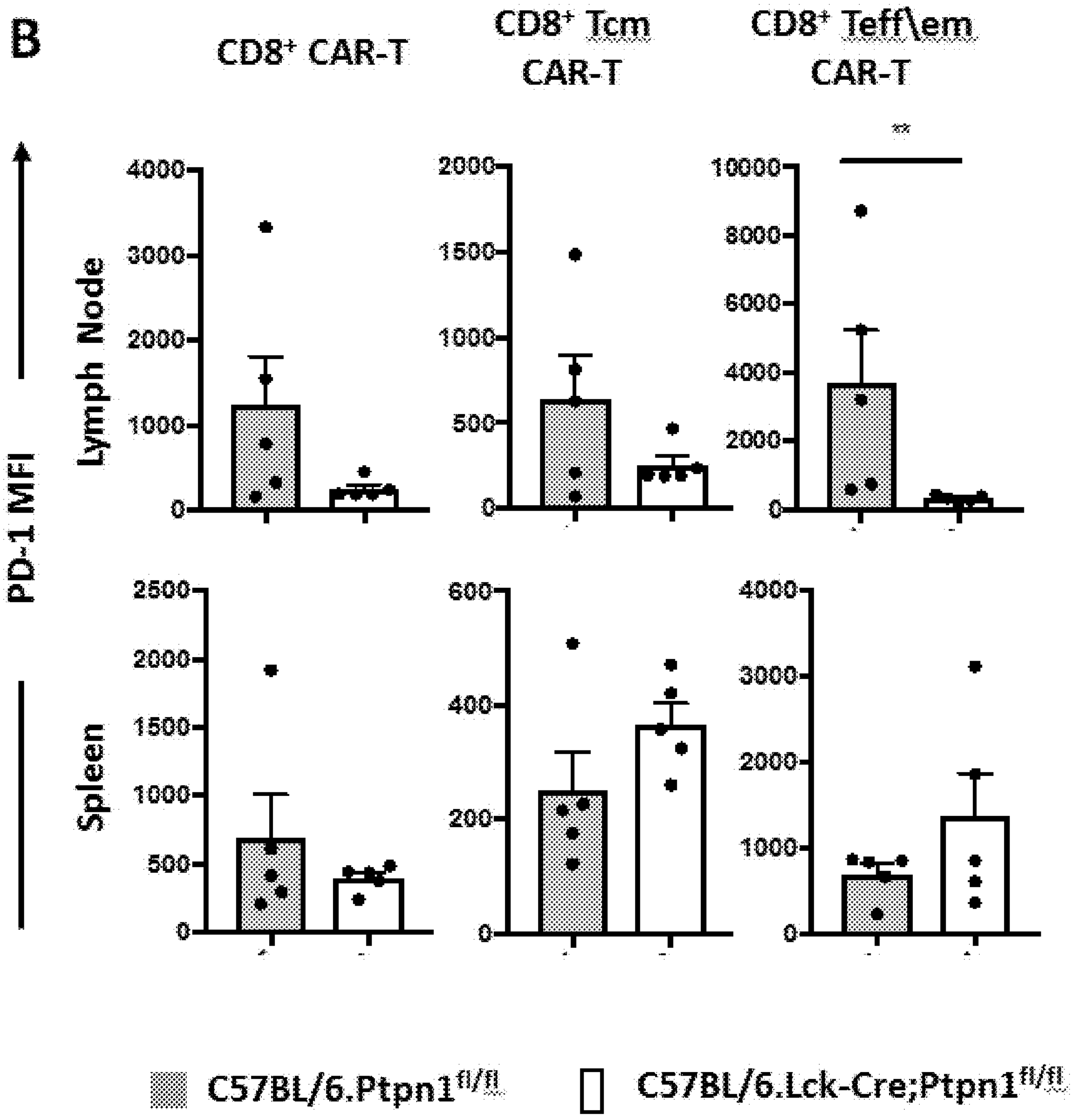

FIG. 15. PTP1B-deficiency results in decreased CAR T cell exhaustion. CAR T cells were isolated from draining lymph nodes and spleens 28 days post adoptive transfer into tumor bearing mice. The expression levels of the exhaustion markers PD-1 and Lag-3 were analyzed by flow cytometry. Lag-3 A) and PD-1B) expression levels in PTP1B-deficient $CD8^+$ total, $CD8^+$ central/memory and $CD8^+$ effector/memory CAR T cells were significantly decreased in draining lymph nodes (Lag-3: p=0.0079, p=0.0079; PD-1: p=0.0079) and spleens (Lag-3: p=0.0079, p=0.0079). Results shown are means±SEM; significances were determined using 2-tailed Mann-Whitney U Test.

Figure 16:
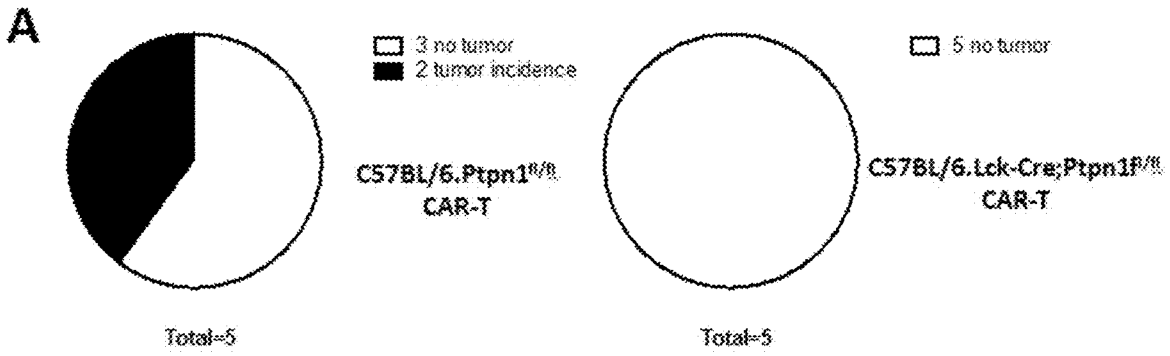
Figure 16:
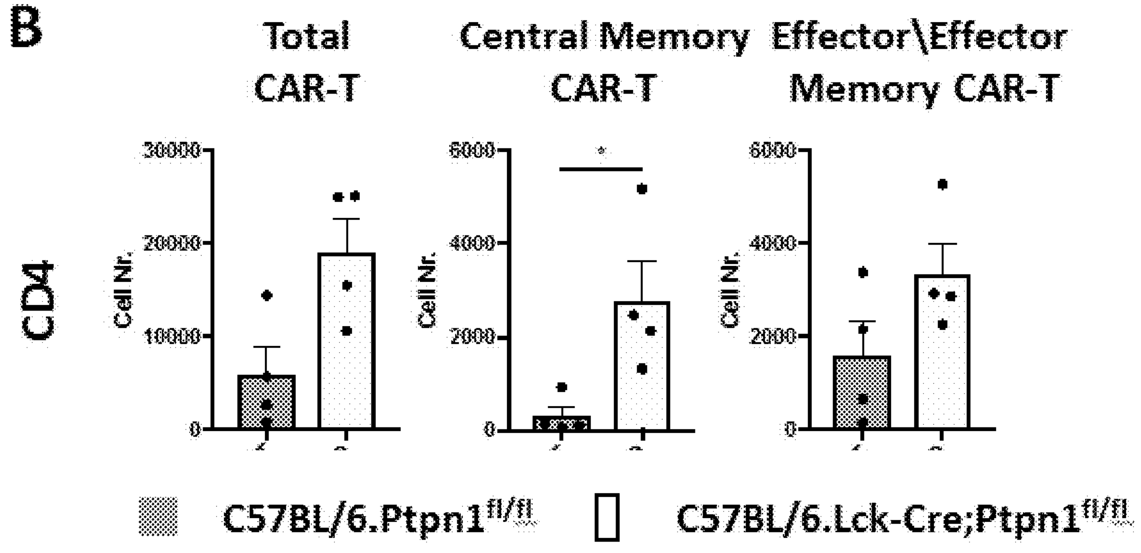
Figure 16:
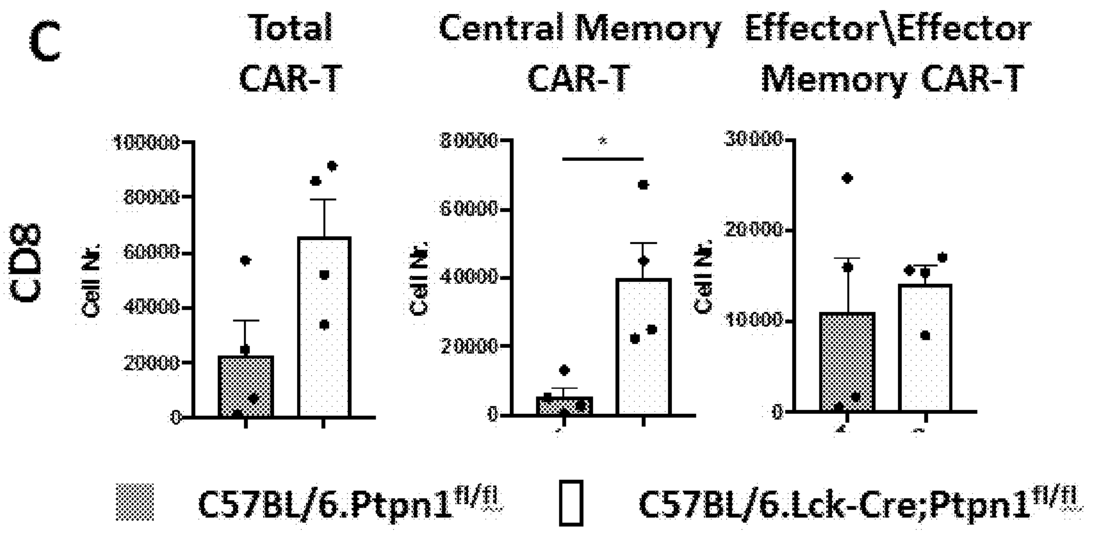
Figure 16:
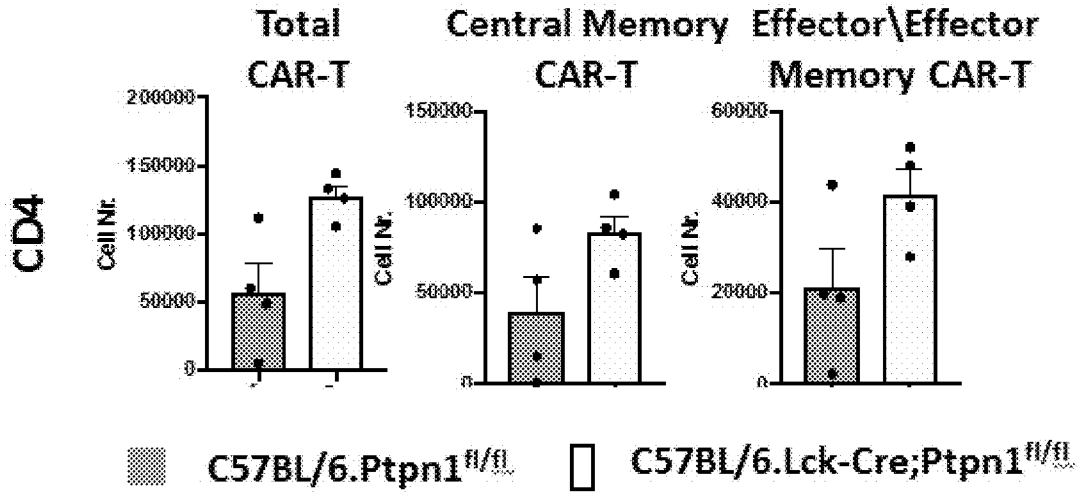
Figure 16:
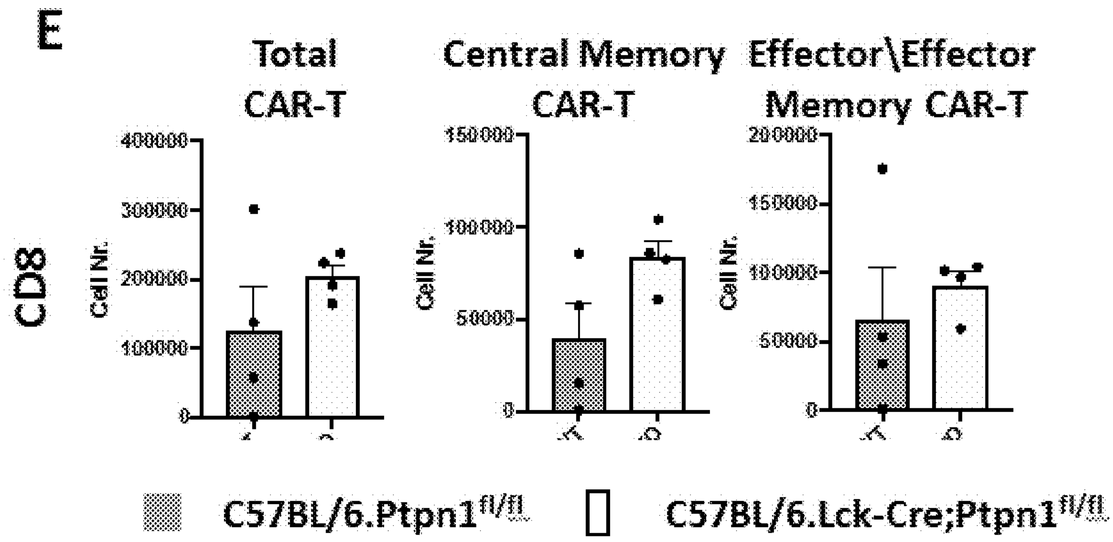

FIG. 16. PTP1B-deficiency enhances $CD8^+$ central memory CAR T cell responses to eradicate tumours beyond that mediated by endogenous immunosurveillance in C57BL/6.Ly5.1 mice. HER-2 overexpressing E0771 breast cancer cells ($2\times10^5$) were injected into the fourth inguinal mammary fat pads of female C57BL/6.Ly5.1 mice. Seven days after tumor injection C57BL/6.Ly5.1 mice received total body irradiation (4 Gy) followed by the adoptive transfer of $1\times10^7$ CAR T cells generated from C57BL/6.Ly5.2 Ptpn1$^{fl/fl}$ and Lck-Cre;Ptpn1$^{fl/fl}$ splenocytes. Mice were injected with IL-2 (50,000 IU/day) on days 0-4 after adoptive CAR T cell transfer. A) 42 days post adoptive transfer 2/5 Ptpn1$^{fl/fl}$ CAR T cells recipients developed tumors whereas 0/5 Lck-Cre;Ptpn1$^{fl/fl}$ CAR T cells recipients stayed tumour-free. Ptpn1$^{fl/fl}$ versus Lck-Cre;Ptpn1$^{fl/fl}$ CAR T cells were isolated from B) lymph nodes or C) spleens and analyzed by flow cytometry. Absolute numbers of total $CD4^+$ or $CD8^+$ T cells and $CD4^+$ versus $CD8^+$ naïve ($CD44^{lo}CD62L^{hi}$) and effector/memory ($CD44^{hi}CD62L^{lo}$; EM) and central/memory ($CD44^{hi}CD62L^{hi}$; CM) T cells were determined. Results shown are means±SEM; significances were determined using two-tailed Mann-Whitney U Test; *p<0.05.

Figure 17:
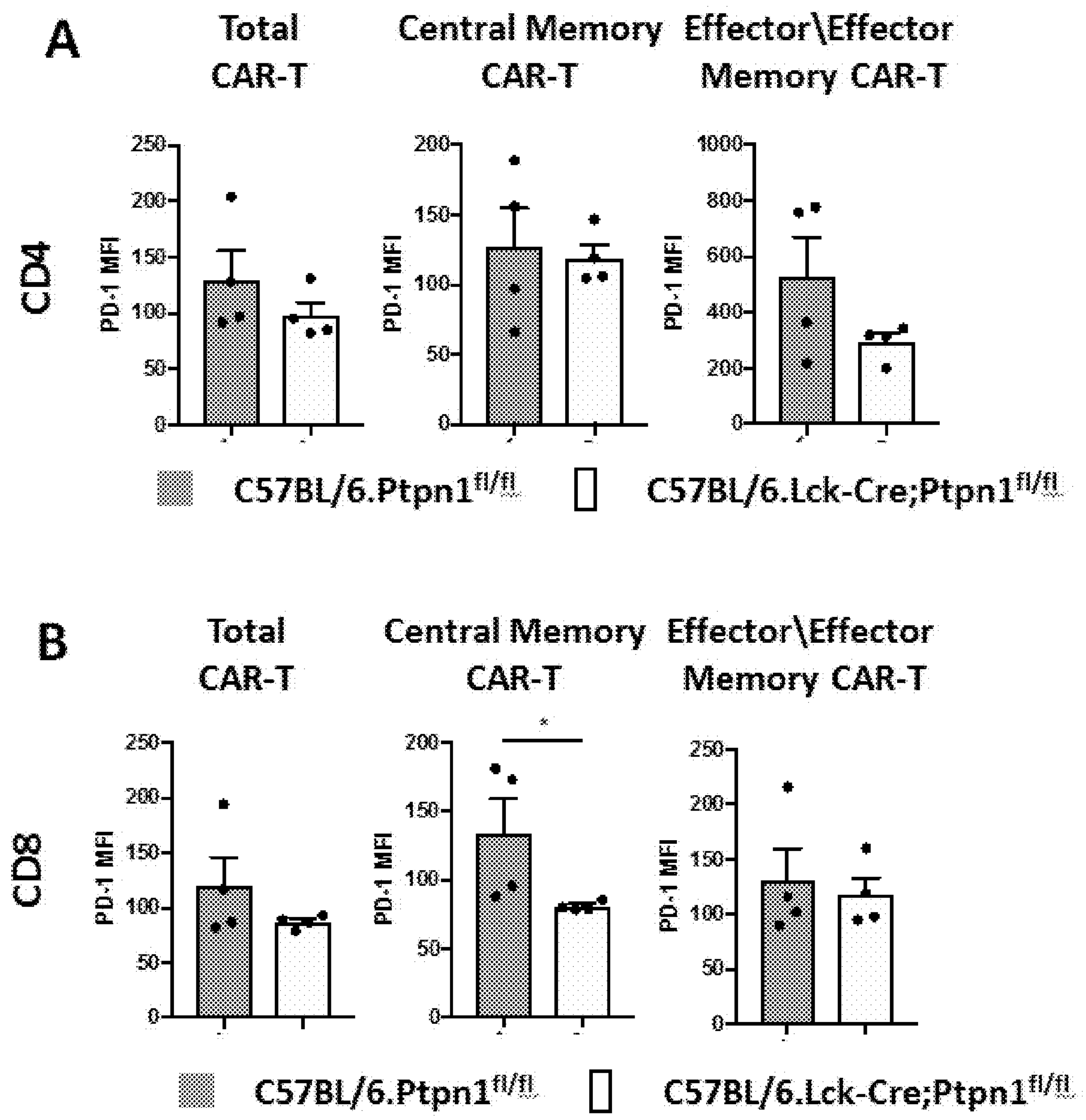
Figure 17:
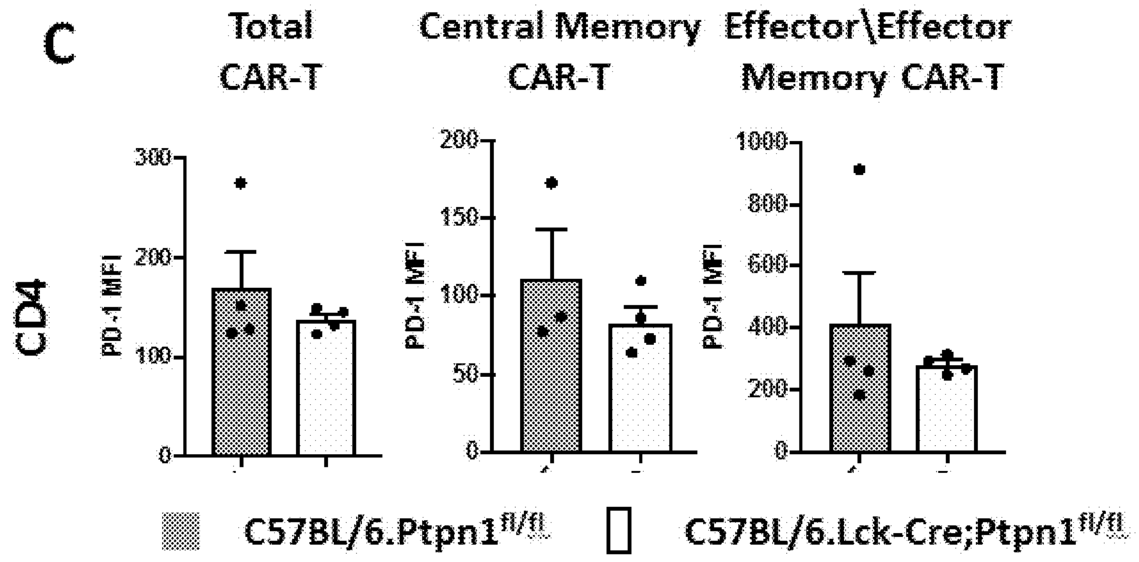
Figure 17:
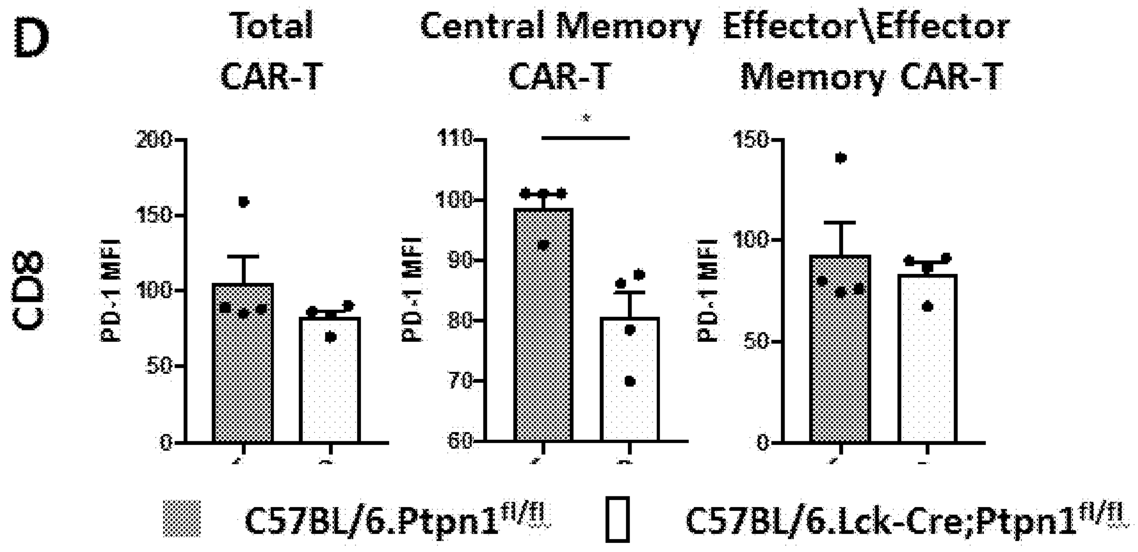

FIG. 17. PTP1B-deficiency represses central/memory CAR T cell exhaustion in C57BL/6.Ly5.1 mice. HER-2 overexpressing E0771 breast cancer cells ($2\times10^5$) were injected into the fourth inguinal mammary fat pads of female C57BL/6.Ly5.1 mice. Seven days after tumour injection C57BL/6.Ly5.1 mice received total body irradiation (4 Gy) followed by the adoptive transfer of $1\times10^7$ CAR T cells generated from Ptpn1$^{fl/fl}$ and Lck-Cre;Ptpn1$^{fl/fl}$ splenocytes. Mice were injected with IL-2 (50,000 IU/day) on days 0-4 after adoptive CAR T cell transfer. HER-2-specific CAR T cells were isolated from the A-B) tumour-draining lymph nodes and c-d) spleens of C57BL/6.Ly5.1 mice 42 days post adoptive transfer and stained for CD4, CD8, CD44, CD62L and PD-1 and PD-1 mean fluorescence intensities (MFI) on $CD4^+$ (A, C) or $CD8^+$ (B, E) central/memory ($CD44^{hi}CD62L^{hi}$) versus effector/memory ($CD44^{hi}CD62L^{lo}$) HER-2-specific CAR T cells were determined by flow cytometry. Representative results (means±SEM) for the indicated numbers of mice and experiments are shown. Significances were determined using 2-tailed Mann-Whitney U Test; *p<0.05.

Figure 18:
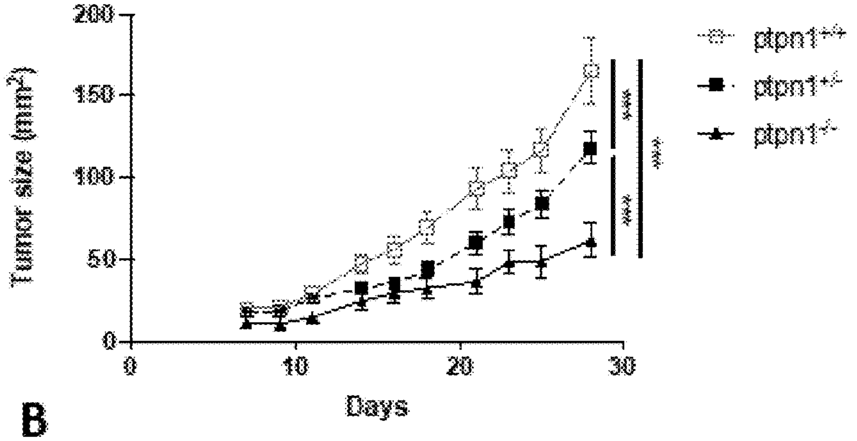
Figure 18:
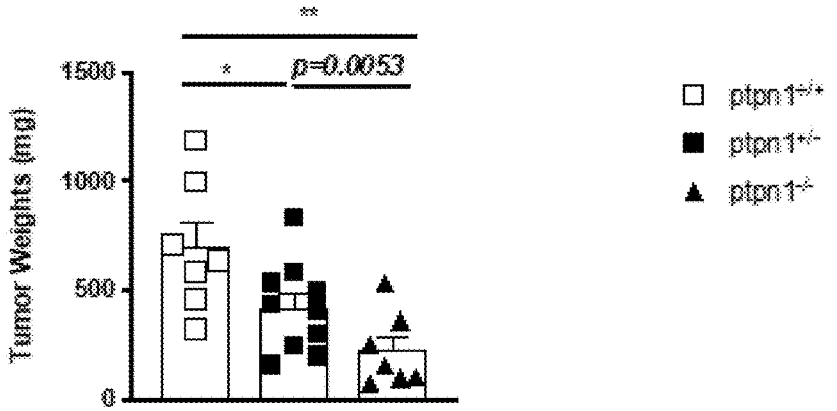
Figure 18:
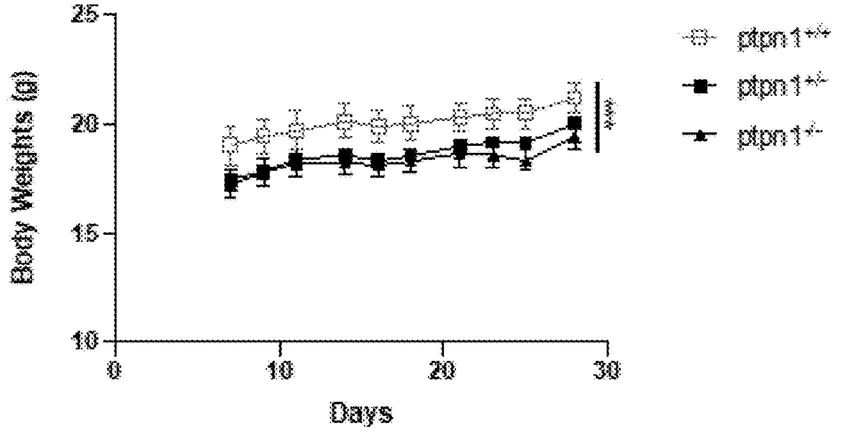
Figure 18:
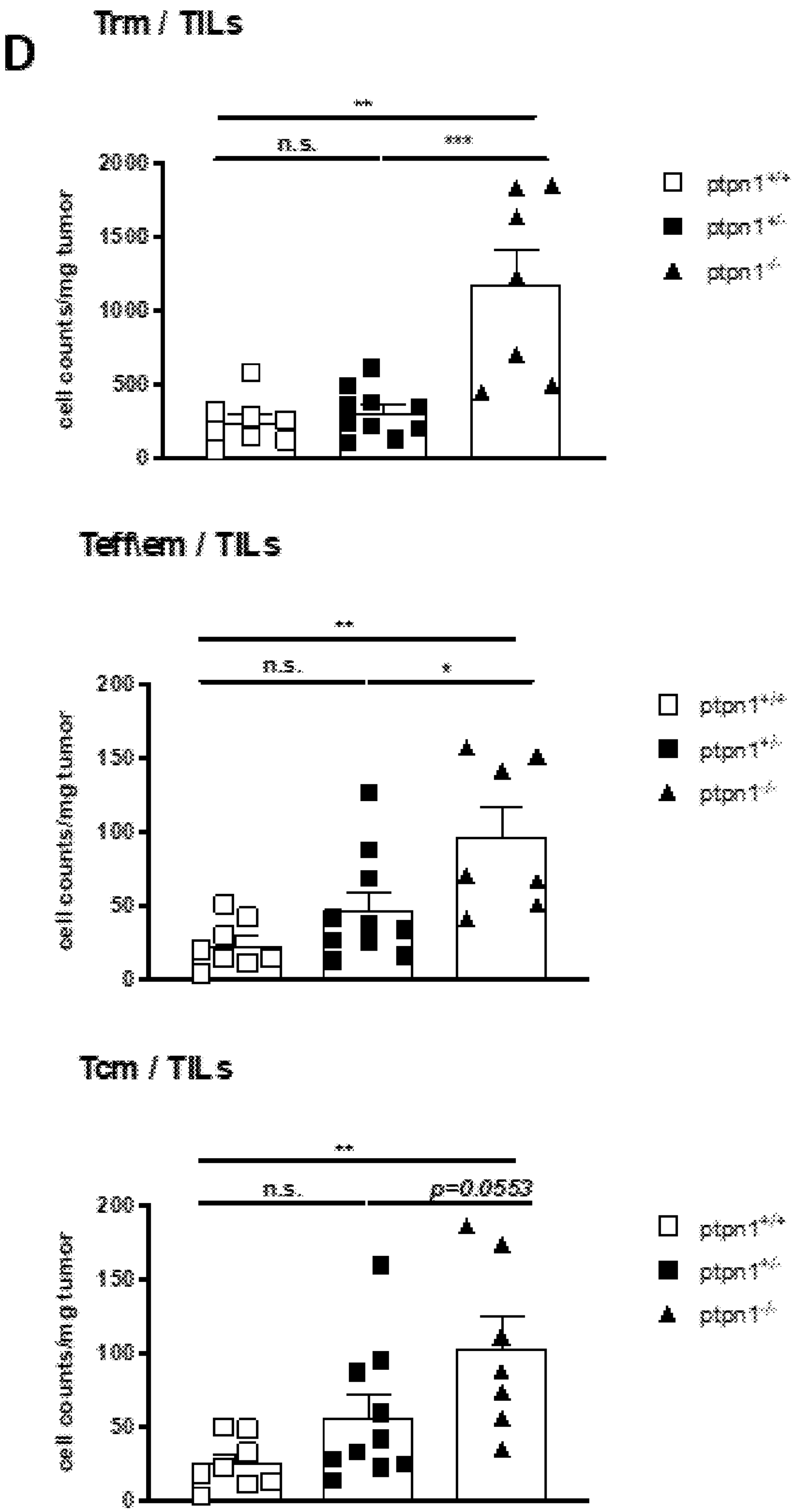
Figure 18:
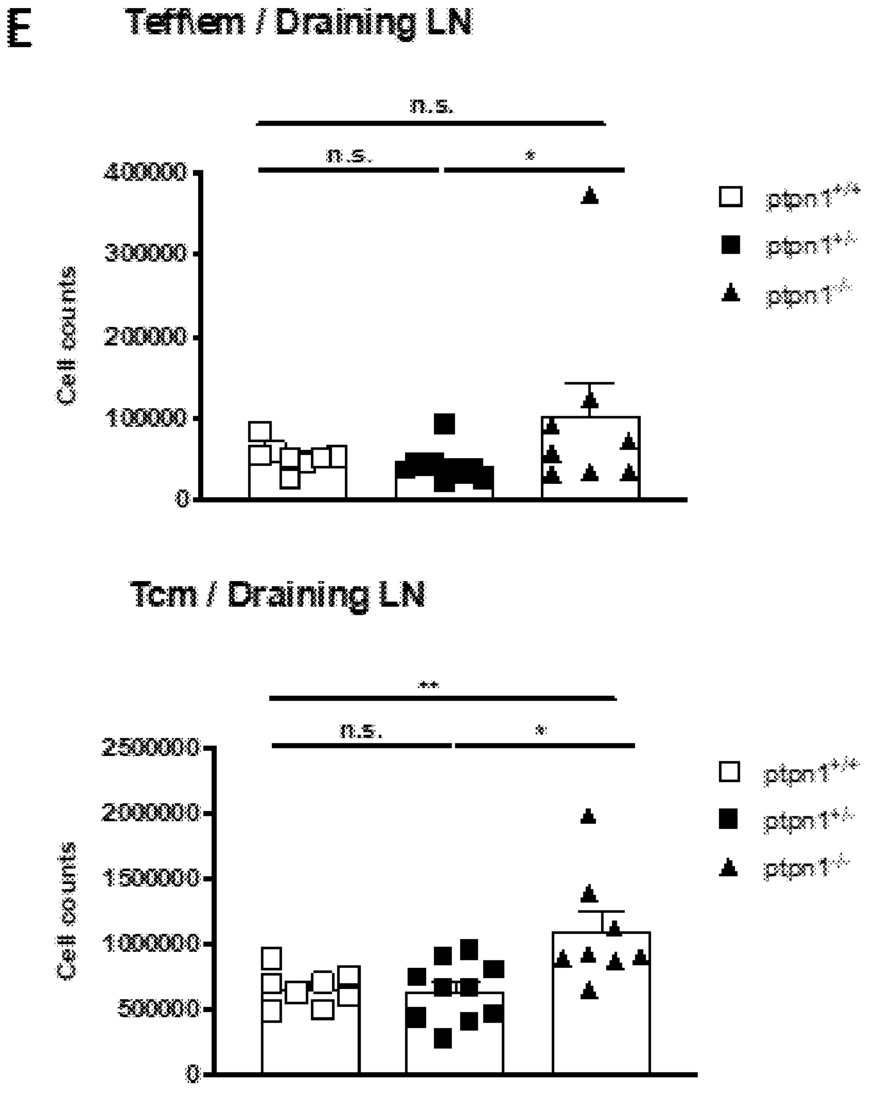

FIG. 18. Repressed syngeneic tumor growth in mice with global PTP1B deficiency. $1\times10^6$ AT-3 OVA breast cancer cells suspended in 20 μl 1×DPBS were transplanted into the mammary fat pads of PTP1B-deficient ($Ptpn1^{-/-}$; n=8), ptp1b-heterozygous ($Ptpn1^{+/+}$; n=10), and PTP1B-competent wild-type ($Ptpn1^{+/+}$; n=8) female mice. A) Tumor growth was monitored for 28 days after the transplantation. PTP1B-deficient mice showed significant suppression of tumor growth in comparison with PTP1B-heterozygous mice (p<0.0001; 2-way ANOVA) and wild-type mice (p<0.0001; 2-way ANOVA). PTP1B-deficient mice also demonstrated enhanced tumor suppression in comparison with PTPB1B-heterozygous mice (p<0.0001; 2-way ANOVA). B) Tumour weight was determined at day 28 post transplantation. The tumor burden from both PTP1B-deficient and PTP1B-heterozygous mice was significantly reduced compared to the tumor burden in wild-type mice (p=0.0041 and p=0.0431). C) Both PTP1B-deficient and PTP1B-heterozygous mice showed significant reduction in body weights in comparison to their wild-type counterpart (p<0.0001 and p<0.0001; 2-way ANOVA). D) Resident memory T cells (Trm), effector/effector memory T cells (Teff/em), and central memory T cells (Tcm) were significantly increased in the PTP1B-deficient mice in comparison to their wild-type counterparts (p=0.0012, p=0.0012, and p=0.0012). E) No significant increase in Teff/em cells (p=0.4418) while Tcm numbers (p=0.003) were significantly increased in the draining lymph nodes. Representative results (means±SEM) for the indicated numbers of mice and experiments are shown. Significances were determined using 2-tailed Mann-Whitney U Test.

Figure 19:
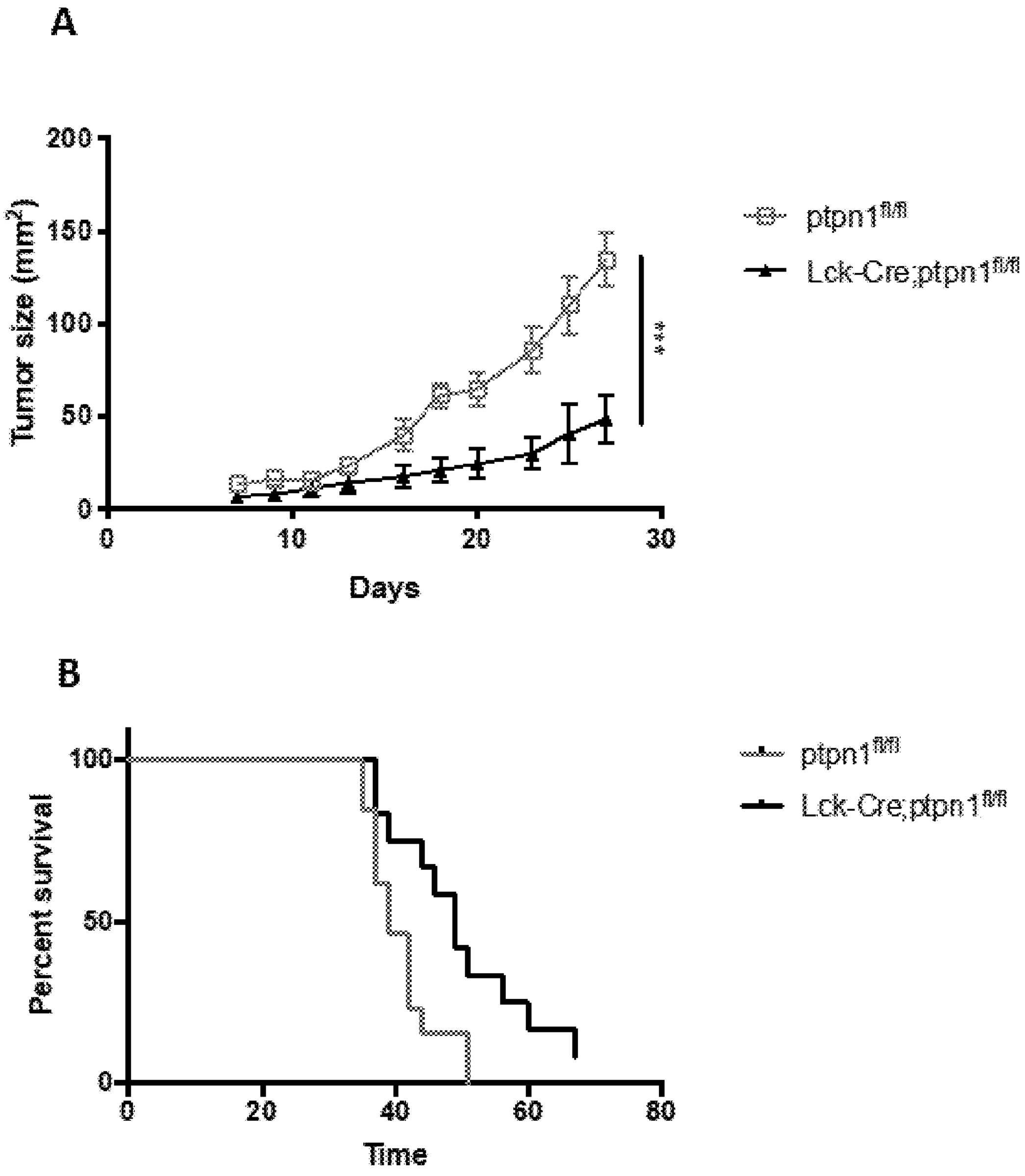
Figure 19:
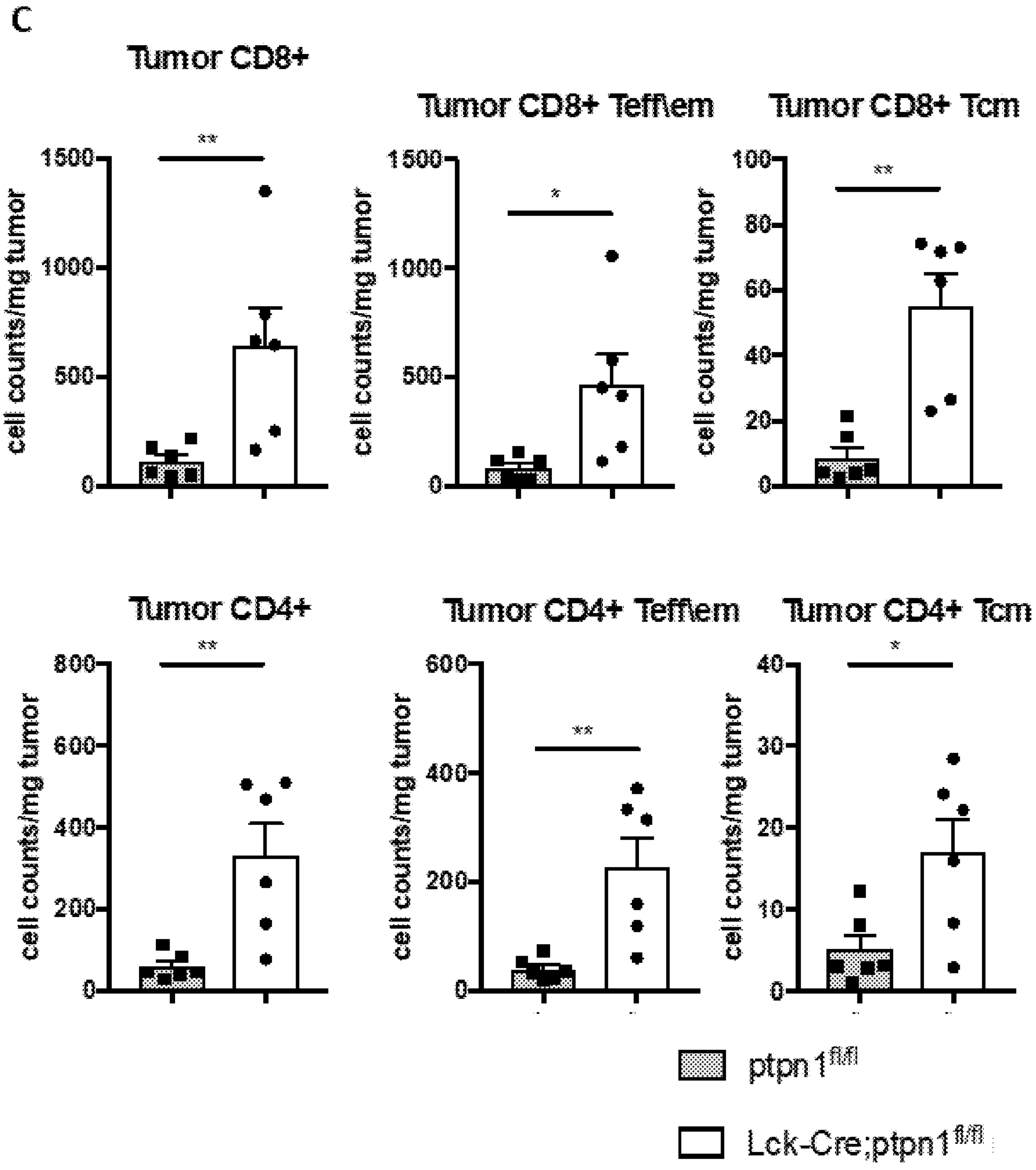

FIG. 19. Repressed syngeneic tumor growth in mice with T cell-specific PTP1B deficiency. $1\times10^6$ AT-3 OVA breast cancer cells suspended in 20 μl 1×DPBS were transplanted into the mammary fat pads of T cell-specific ptp1b-deficient (Lck-Cre;$Ptpn1^{fl/fl}$; n=8) and wild-type ($Ptpn1^{fl/fl}$; n=8) female mice. A) Tumor growth was significantly delayed in mice with T cell-specific PTP1B-deficiency (p<0.0001; 2-way ANOVA). B) Overall survival of tumor bearing mice was significantly improved in Lck-Cre;$Ptpn1^{fl/fl}$ mice (p<0.0001; 2-way ANOVA). C) Tumor infiltrating total $CD8^+$ T cells, $CD8^+$ $T_{eff/em}$ cells, $CD8^+$ $T_{cm}$ cells, total $CD4^+$ T cells, $CD4^+$ $T_{eff/em}$ cells and $CD4^+$ $T_{cm}$ cells were significantly increased in Lck-Cre;$Ptpn1^{fl/fl}$ mice (p=0.0087, p=0.0152, p=0.0022, p=0.0087, p=0.0043 and p=0.0411). Representative results (means±SEM) for the indicated numbers of mice and experiments are shown. Significances were determined using 2-tailed Mann-Whitney U Test.

Figure 20:
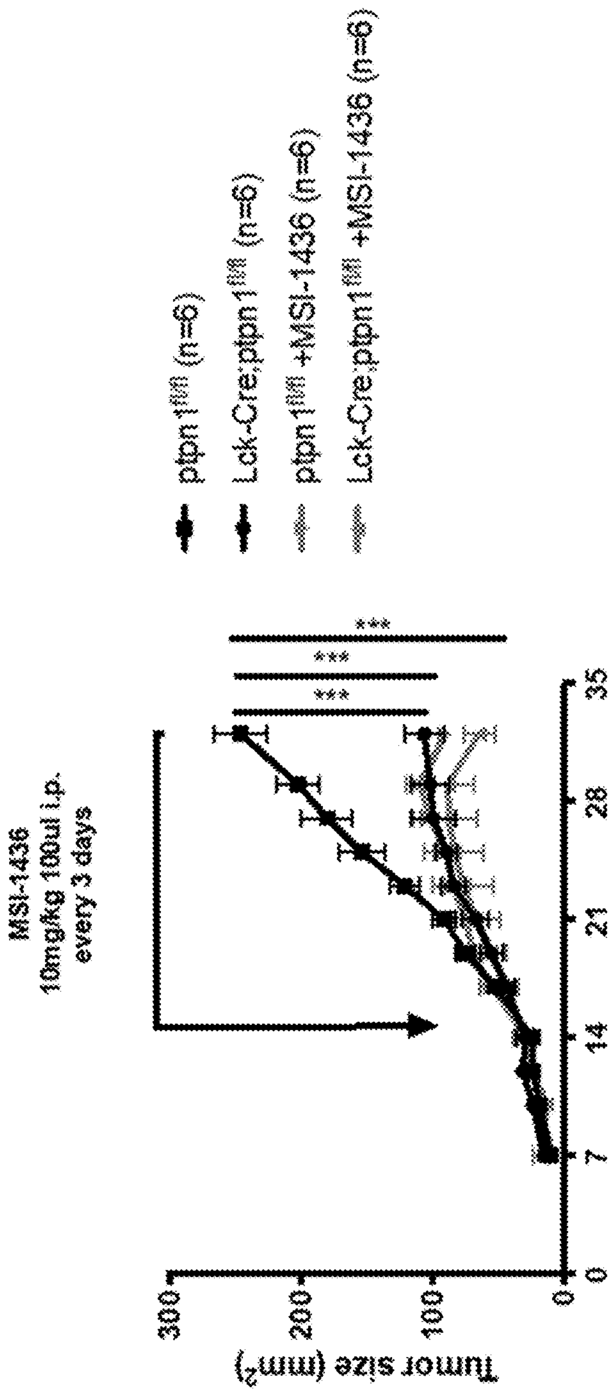
Figure 20:
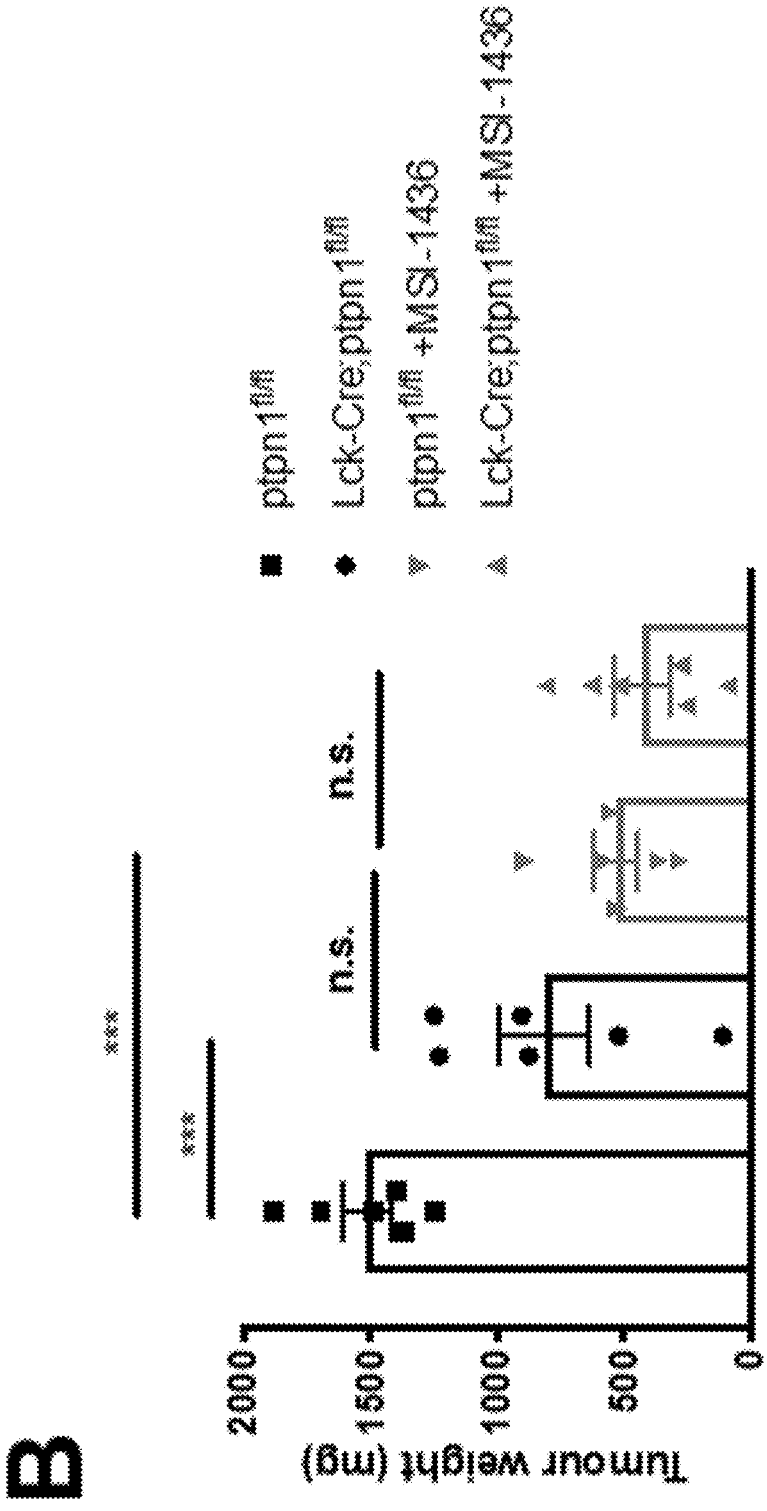
Figure 20:
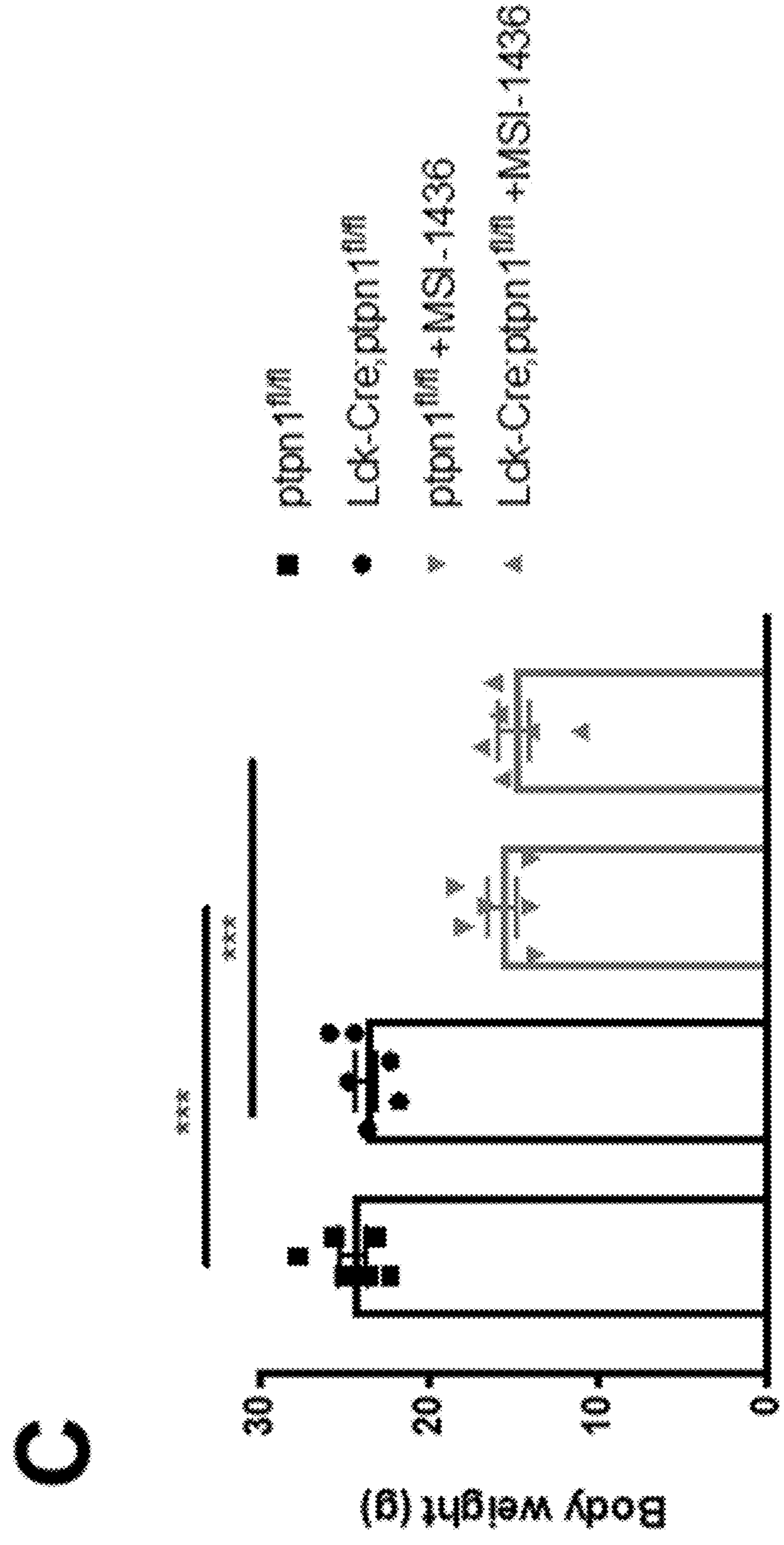

FIG. 20. PTP1B-specific inhibitor MSI-1436 (Trodusquemine) repressed tumor growth. $1\times10^6$ AT-3 OVA breast cancer cells suspended in 20 μl 1×DPBS were transplanted into mammary fat pads of T cell-specific PTP1B-deficient (Lck-Cre;$Ptpn1^{fl/fl}$; n=16) and PTP1B wild-type ($Ptpn1^{fl/fl}$; n=16) female mice. 17 days after the tumor cell transplantation, MSI-1436 was applied to recipient mice through intraperitoneal injection in 100 μl 0.9% (v/v) saline with the concentration of 10 mg per kilogram body weight. 8 out 16 mice from both $Ptpn1^{fl/fl}$ and Lck-Cre;$Ptpn^{fl/fl}$ recipients were treated every three days with MSI-1436 before the start of the dark cycle. A) Tumor growth was significantly suppressed in Lck-Cre;$Ptpn1^{fl/fl}$ mice as well as $Ptpn1^{fl/fl}$ and Lck-Cre;$Ptpn1^{fl/fl}$ mice treated with MSI-1436 in comparison to $Ptpn1^{fl/fl}$ recipients (p<0.0001, p<0.0001 and p<0.0001; 2-way ANOVA). B) T cell-specific PTP1B-deficiency significantly decreased the tumor burden in the Lck-Cre;$Ptpn1^{fl/fl}$ mice in comparison to $Ptpn1^{fl/fl}$ recipients (p=0.0007), MSI-1436-treated $Ptpn1^{fl/fl}$ mice exhibited a significant reduction of tumor burden when compared to the non-treated counterparts (p<0.0001). C) Consistent with previous studies MSI-1436 treatment caused significant weight loss in Lck-Cre;$Ptpn1^{fl/fl}$ or $Ptpn1^{fl/fl}$ mice (p<0.0001 and p<0.0001). This was accompanied by a reduction in food intake and adiposity but no changes in lean mass (data not shown). Representative results (means±SEM) for the indicated numbers of mice and experiments are shown. Significances were determined using 2-tailed Mann-Whitney U Test.

DETAILED DESCRIPTION OF THE EMBODIMENTS

It will be understood that the invention disclosed and defined in this specification extends to all alternative combinations of two or more of the individual features mentioned or evident from the text or drawings. All of these different combinations constitute various alternative aspects of the invention.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described. It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

The inventors have developed a method for the efficient preparation of cells for use in adoptive cell transfer, particularly for cancer immunotherapy. The inventors have surprisingly found that inhibiting the activity of PTP1B in T cells enhances the activation of such cells and their capacity for killing a target cell. Further, an advantage of the present invention is that T cells which are tolerised but would otherwise be useful in adoptive cell transfer (ADC), for example as they are specific for tumour antigens in the case of tumour infiltrating lymphocytes, can be reinvigorated and tolerance reduced.

Still further, the inventors have found that inhibition of PTP1B in T cells substantially reduces the need for concomitant stimulation with cytokines (for example, to enhance expansion of the cells intended for ADC). Without wishing to be bound by theory, the inventors believe that cells for ADC which are also treated to inhibit PTP1B activity are more sensitive to cytokines such as IL-17, IL-15 and IL-2 so that patients treated with the cells may not need concomitant treatment with cytokines. Alternatively, fewer cells can be used for ADC, given the increased responsiveness of T cells to cytokines when PTP1B is inhibited.

Without being bound by any theory or mode of action, it is believed that inhibition of PTP1B activity causes alteration in T cell receptor (TCR) signalling thereby reversing or avoiding tolerance and instead promoting differentiation of T cells down the cytotoxic T cell lineage. For example, isolated CD8+ T cells treated so as to reduce PTP1B activity lead to any one or more of the following functions: develop cytotoxic activity towards cells that bear an antigen to which an enhanced immune response would be desirable, enhanced sustenance and/or antigen-recall responses to presentation of the antigen, or have functional and/or phenotypic characteristics of effector T cells.

Although cancer immunotherapies of ex vivo cultured CD8+ T cells have been demonstrated to exhibit remarkable efficacy, such therapies are not effective in every patient as it is difficult to obtain an effective number of CD8+ T cells that have the ability to target the tumour cells and kill the tumour cell once recognised. The present invention provides a means for producing cells that have an enhanced capacity to kill a target cell, such as a tumour cell.

A further advantage identified by the inventors is that inhibition of PTP1B in T cells increases persistence of central memory and effector memory T cells. This means that in addition to providing for an increase in cytotoxic killing in the period immediately after PTP1B inhibition, the methods of the present invention provide for better adaptation and preparation of the immune system to deal with long term or subsequent exposure to a relevant antigen (for example, upon relapse of the relevant disease or condition).

Anatomic sources of leukocytes, preferably T cells, from a subject include peripheral blood, tumours, malignant effusions, and draining lymph nodes. Lymphocytes used for adoptive transfer can either be derived from the stroma of resected tumours (tumour infiltrating lymphocytes), or from blood and: genetically engineered to express antitumour T cell receptors or chimeric antigen receptors (CARs), enriched with mixed lymphocyte tumour cell cultures (MLTCs) or cloned using autologous antigen presenting cells and tumour derived peptides. The lymphocytes used for infusion can be isolated from an allogenic donor, preferably HLA matched, or from the cancer-bearing subject. In one embodiment, the leukocytes, preferably T cells, from a subject are not obtained or derived from the bone marrow.

In any method of the invention the leukocytes, preferably T cells that have been cultured in the presence of a PTP1B inhibitor can be transferred into the same mammal from which cells were obtained. In other words, the cells used in a method of the invention can be an autologous cell, i.e., can be obtained from the mammal in which the medical condition is treated or prevented. Alternatively, the cell can be allogenically transferred into another subject. Preferably, the cell is autologous to the subject in a method of treating or preventing a medical condition in the subject.

One source of T cells targeted for cancer immunotherapy may be to use artificial chimeric receptors derived, for example, from the antigen binding domain of a monoclonal antibody. When coupled to appropriate intracellular signaling domains, T cells expressing these chimeric antigen receptors (CAR) can kill tumour cell targets. CAR T cells have the advantage of acting in a MHC unrestricted manner, allowing them to target tumour cells in which antigen processing or presentation pathways are disrupted. Moreover, they can be directed to nonpeptide antigens on the cell surface, broadening the range of target structures that can be recognized on malignant cells. Hence, CAR-expressing T cells can complement MHC restricted cytotoxic T cells, and increase the overall effectiveness of this cellular immunotherapy.

When naïve CD8+ and CD4+ T cells engage peptide antigen presented by major histocompatibility complex (MHC) molecules, the T cell receptor signal strength determines whether T cells progress past the $G_1$ restriction point and commit to cellular division, produce interleukin-2 (IL-2) and undergo clonal expansion/proliferation and differentiate and acquire various effector functions. TCR signaling is reliant on tyrosine phosphorylation mediated by the Src family protein tyrosine kinases, Lck and Fyn, and the Syk family PTK ZAP-70. Engagement of the TCR allows for Lck to phosphorylate the immunoreceptor tyrosine-based activation motifs of the TCR that result ZAP-70 recruitment and activation and the phosphorylation of adaptor proteins such as LAT. This in turn allows for the nucleation of signaling complexes and the phosphorylation and activation of multiple effector pathways. Upon TCR engagement, the activation and/or functions of Lck are regulated by the localisation of Lck and its substrates, as well as the abundance, activity and segregation of regulatory molecules within the immunological synapse. Such regulatory molecules include protein tyrosine phosphatases (PTPs) that regulate the phosphorylation of the Lck Y505 inhibitory site, as well as the Lck Y394 activating site.

PTP1B (also known as PTPN1, PTP1B, protein tyrosine phosphatase, non-receptor type 1, Tyrosine-protein phosphatase non-receptor type 1 or protein-tyrosine phosphatase 1B) is a ubiquitous phosphatase anchored in the endoplasmic reticulum by its C-terminal end and has its catalytic regions exposed to the cytosol. PTP1B is known to dephosphorylate a wide variety of phosphoproteins, such as receptors for the growth factors insulin and epidermal growth factor (EGF), c-Src and beta-catenin. PTP1B also dephosphorylates Janus-activated protein kinase 9JAK) family members including Tyk-2 and JAK-2. PTP1B is reported to be a major negative regulator of the insulin receptor and also of leptin signalling. The PTPN1 gene, which encodes PTP1B, is located in 20q13, a genomic region that is linked to insulin resistance and diabetes in human populations from different geographical origins. More than 20 single nucleotide polymorphisms (SNPs) that are associated with increased risk of type 2 diabetes have been identified within the PTPN1 gene. Whole-body deletion of PTP1B in mice results in increased insulin sensitivity and improved glucose tolerance. In addition, PTP1B has been shown to modulate cytokine receptor signalling, including IFN-γ signalling. The role of PTP1B in cancer is unclear, with either increased or reduced expression observed in different cancer types.

In order to determine if the presence of a PTP1B inhibitor has inhibited PTP1B, experiments such as the following could be performed: measure PTP1B activity in PTP1B immunoprecipitates using p-NPP (para-nitrophenylphosphate) and p-tyr-RCML (p-tyr-reduced, carboxyamidomethylated and maleylated lysozyme) as substrates as described previously (Bukczynska P et al. Biochem. J. 2004 Jun. 15; 380(Pt 3):939-49; Tiganis T et al. J. Biol. Chem. 1997 Aug. 22; 272(34):21548-57). Alternatively, analysis of known substrates of PTP1B such as c-Src, insulin receptor, EGF receptor, Tyk-2, JAK-2 and the transcription factor STAT5 for tyrosine-phosphorylation by flow cytometry and immuno-blotting can be performed.

A PTP1B inhibitor useful in the present invention is one that completely or partially reduces one or more functions of PTP1B as described herein. Preferably, a PTP1B inhibitor reduces phosphatase activity of PTP1B (such as a small molecule, peptide or peptidomimetic), reduces the transcriptional activity of the PTP1B gene, or reduces the amount of PTP1B mRNA or protein present in the cell.

In any embodiment of the invention, the inhibition of PTP1B may be inhibition of at least 50%, at least 60%, at least 70%, at least 80%, at least 90% or 100% inhibition. In further embodiments, the inhibition is of PTP1B only, such that there are minimal-to-no off-target effects resulting in inhibition of other targets. Accordingly, in preferred embodiments, the inhibition of targets other than PTP1B is no more than 20%, no more than 10%, no more than 5% inhibition.

As used herein, a PTP1B inhibitor may be any molecule that inhibits the phosphatase activity of PTP1B or reduces the level of PTP1B in a cell. The inhibitor may be a direct inhibitor of the phosphatase active site, may act allosterically to inhibit phosphatase activity, inhibit interaction of PTP1B with its substrate, or may reduce the level of PTP1B by reducing the transcriptional activity of the PTP1B gene, or reducing the amount of PTP1B mRNA or protein present in the cell.

An example of a direct inhibitor of the phosphatase active site, an inhibitor that acts allosterically to inhibit phosphatase activity, or an inhibitor that inhibits interaction of PTP1B with its substrate is a small molecule, for example:

- Claramine (Sigma, 1545; also referred to as (3β,6β)-6-[[3-[[4-[(3-Aminopropyl)amino]butyl]amino]propyl]amino]-cholestan-3-ol) and derivatives thereof;
- Trodusquemine (MSI-1436, produlestan, Trodulamine, troduscemine, CAS No: 186139-09-3, a naturally-occurring cholestane and non-competitive, allosteric inhibitor of PTP1B, trodusquemine selectively targets and inhibits PTP1B, thereby preventing PTP1B-mediated signalling) and derivatives thereof including DPM-1001 (Krishnan et al 2018, JBC, 293:1517-1525);
- 3-(3,5-dibromo-4-hydroxy-benzoyl)-2-ethyl-benzofuran-6-sulfonicacid-(4-(thiazol-2-ylsulfamyl)-phenyl)-amide (also referred to as PTP Inhibitor XXII, CAS no: 765317-72-4, Thermofisher Scientific or Calbiochem) and derivatives thereof;
- 3-Hexadecanoyl-5-hydroxymethyl-tetronic acid calcium salt (RK-682, CAS no: 332131-32-5, Santa Cruz Biotechnology) and derivatives thereof;
- 2-[(Carboxycarbonyl)amino]-4,5,6,7-tetrahydrothieno[2,3-c]pyridine-3-carboxylic acid hydrochloride (TCS-401, CAS no: 243966-09-8, Santa Cruz Biotechnology) and derivatives thereof;
- 6-Methyl-2-(oxalylamino)-4,5,6,7-tetrahydrothieno[2,3-c]pyridine-3-carboxylic acid trifluoroacetic acid salt (BML-267, Santa Cruz Biotechnology) and derivatives thereof;

or a peptide, or peptidomimetic.

An example of an inhibitor that may reduce the amount of PTP1B mRNA or protein present in the cell is an inhibitory or interfering RNA, such as antisense RNA, siRNA, microRNA or shRNA.

An example of an shRNA sequences which may reduce the amount of PTP1B mRNA include:

```
                                    (SEQ ID NO: 1)
AATTGCACC-AGGAAGATAATGACTATATC
```

Exemplary siRNA sequences include:

```
Sense:
                                    (SEQ ID NO: 2)
'5-UAGGUACAGAGACGUCAGUdTdT-3';

Antisense:
                                    (SEQ ID NO: 3)
5'-ACUGACGUCUCUGUACCUAdTdT-3

Sense,
                                    (SEQ ID NO: 4)
5'-UAGGUACAGAGACGUCAGUdTdT-3';

Antisense,
                                    (SEQ ID NO: 5)
5'-ACUGACGUCUCUGUACCUAdTdT-3'

Sense,
                                    (SEQ ID NO: 6)
5-'AAATCAACGGAAGAAGGGTCT-3'

Sense:
                                    (SEQ ID NO: 7)
5'-NNUGACCAUAGUCGGAUUAAA-3'

Sense:
                                    (SEQ ID NO: 8)
5'-UUGAUGUAGUUUAAUCCGACUAUGG-3'

Anti-sense:
                                    (SEQ ID NO: 9)
5'-CCAUAGUCGGAUUAAACUACAUCAA-3'
```

Anti-sense: 5'-CCAUAGUCGGAUUAAACUACAUCAA-3' (SEQ ID NO: 9) The skilled person will also appreciate that it is possible to obtain shRNAs or siRNAs, which can be used to reduce PTP1B mRNA, from a number of commercial sources, including from Dharmacon (Madrid, Spain) and Thermofisher (USA).

Commercially available shRNA targeted to ptp1b can be purchased; for example, from Open Biosystems (Dharmacon) under catalog no. RHS3979-9571385.

Preferably, the siRNA, shRNA target is (GenBank NCBI Reference Sequences referred to):

- exon 2, preferably starting at position 291 of NM_001278618.1;
- exon 3, preferably starting at position 382 of NM_002827.3;
- exons 3 and 4, preferably starting at position 466 of NM_001278618.1;
- exons 4 and 5, preferably starting at position 557 of NM_002827.3; or
- exons 2 and 3, preferably starting at position 360 of NM_002827.3.

Preferably, the shRNA has a sequence of at least 50%, 60%, 70%, 80%, 90%, 91%, 92%, 93%, 94%, 95%, 96%, 97%, 98% or 99% identity to any sequence described herein provided the shRNA still retains the ability to reduce PTP1B levels in a cell.

Further, the inhibition of PTP1B may also include genome editing to delete or modify all or part of a sequence encoding PTP1B. An exemplary genome editing technique is the CRISPR/Cas9 system (Jinek, M., et al. (2012) Science, 337, 816-821; Cong L., et al. (2013) Science, 339, 819-823; and Qi, L. S., et al. (2013) Cell, 152, 1173-1183). As such, in accordance with the present invention, the PTP1B inhibitor may include a gRNA (including an sgRNA) for use in CRISPR-Cas9 genome editing to inhibit or delete PTP1B activity. More specifically, the present invention contemplates the use of CRISPR-Cas9 to delete Ptp1b in human CAR T cells. Moreover, use of CRISPR-Cas9 enables the inhibition to be of PTP1B alone (i.e., wherein only PTP1B is inhibited). In certain embodiments, the inhibition of only PTP1B may be complete inhibition (i.e., knock-out) of PTP1B function, or a reduction in PTP1B activity/expression (i.e., knock-down or partial knock-out).

The skilled person will be able to purchase or design gRNAs or crRNAs which target a variety of PTP1B sequences. Examples of such gRNA target sequences include:

```
                                    (SEQ ID NO: 10)
TTCGAGCAGATCGACAAGTC

                                    (SEQ ID NO: 11)
GATGTAGTTTAATCCGACTA

                                    (SEQ ID NO: 12)
GAGCTGGGCGGCCATTTACC

                                    (SEQ ID NO: 13)
TGACGTCTCTGTACCTATTT

                                    (SEQ ID NO: 14)
CAAAAGTGACCGCATGTGTT

                                    (SEQ ID NO: 15)
GTCTTTCAGTTGACCATAGT
```

The miRNA, siRNA or shRNA can be delivered to the relevant T cell by using a viral vector. There are a large number of available viral vectors that are suitable for use with the present invention, including those identified for human gene therapy applications. Suitable viral vectors include vectors based on RNA viruses, such as retrovirus-derived vectors, e.g., Moloney murine leukemia virus (MLV)-derived vectors, and include more complex retrovirus-derived vectors, e.g., Lentivirus-derived vectors. Human Immunodeficiency virus (HIN-I)-derived vectors belong to this category. Other examples include lentivirus vectors derived from HIN-2, feline immunodeficiency virus (FIN), equine infectious anaemia virus, simian immunodeficiency virus (SIV) and Maedi-Visna virus.

Preferably a modified retrovirus, even more preferably a modified lentivirus, is used to deliver the specific miRNA, siRNA or shRNA. This virus may also include sequences that encode the chimeric antigen T cell receptor for targeting the specific cell to be killed. The polynucleotide and any associated genetic elements are thus integrated into the genome of the host cell as a provirus. The modified retrovirus is preferably produced in a packaging cell from a viral vector that includes the sequences necessary for production of the virus as well as the miRNA, siRNA or shRNA and/or CAR. The viral vector may also include genetic elements that facilitate expression of the miRNA, siRNA or shRNA, such as promoter and enhancer sequences. In order to prevent replication in the target cell, endogenous viral genes required for replication may be removed.

The skilled person will be familiar with methods for virally introducing Cas9 and guide RNAs (gRNAs) into cells for the purpose of targeting PTP1B (for example, utilising lentiviral methods). In addition, the present invention contemplates the use of Cas9 ribonucleoprotein (RNP)-mediated gene-editing to delete PTP1B (for example using GeneArt™ Platinum™ Cas9 Nuclease pre-loaded with synthesized crRNA:tracrRNA (Dharmacon) targeting human PTP1B using the Neon Transfection system).

The skilled person will be able to determine whether PTP1B mRNA levels have been reduced using standard quantitative PCR methods. For example, the Taqman gene expression assay to determine Ptpn1 expression can be used (Mm00448427_m1, Thermofisher Scientific). The skilled person will understand that such assays can be used to confirm PTP1B mRNA reduction resulting from siRNA or shRNA targeting or alternatively as the result of gRNA-derived CRISPR-Cas9 genome editing to reduce PTP1B activity.

A composition comprising the CD8+ T cells and the PTP1B inhibitor may further include the cancer specific antigen and/or one or more cytokines to enhance cell killing (such as IL-2 or IFNγ). When the antigen is present in the composition comprising the isolated, enriched or purified CD8+ T cells, the antigen may be present as an independent entity, or in any context by which the antigen can interact with the T cell receptor or CAR present on the CD8+ T cells. When the antigen can interact with the TCR of the CD8+ T cells the CD8+ T cells can become activated. Examples of various embodiments by which the antigen can be provided in the composition such that it can be recognized by the CD8+ TCR include but are not limited to it the antigen being present in association with MHC-I (or the equivalent presentation in an animal model) on the surface of antigen presenting cells, such as dendritic cells, macrophages or certain activated epithelial cells. Alternatively, the antigen could be in physical association with any other natural or synthesized molecule or other compound, complex, entity, substrate, etc., that would facilitate the recognition of the antigen by the TCR on the CD8+ T cells. For example, the antigen could be complexed to a MHC-1 or other suitable molecule for presenting the antigen to the CD8+ TCR, and the MHC-I or other suitable molecule could be in physical association with a substrate, such as a latex bead, plastic surface of any plate, or any other suitable substrate, to facilitate appropriate access of the antigen to the CD8+ T cell TCR such that the antigen is recognized by the CD8+ T cell.

CD8+ T cells may be obtained using routine cell sorting techniques that discriminate and segregate T cells based on T cell surface markers can be used to obtain an isolated population CD8+ T cells for use in the compositions and methods of the invention. For example, a biological sample including blood and/or peripheral blood lymphocytes can be obtained from an individual and CD8+ T cells isolated from the sample using commercially available devices and reagents, thereby obtaining an isolated population of CD8+ T cells. Murine CD8+ T cells may be further characterized and/or isolated on a phenotypic basis via the use of additional cell surface markers such as CD44, L-selectin (CD62L), CD25, CD49d, CD122, CD27, CD43, CD69, KLRG-1, CXCR3, CCR7, IL-7Rα and KLRG-1. CD8+ T cells may be initially enriched by negatively selecting CD4+, NK1.1+, B220+, CD11b+, TER119+, Gr-1+, CD11c+ and CD19+ cells. Naive CD8+ T cells are characterized as CD44 low, CD62L high, CCR7 high, CD25 low, CD43 low, CD49d low, CD69 low, IL-7Rα high and CD122 low, whereas antigen experienced memory T cells are CD44 high, CD49d high, CD122 high, CD27 high, CD43 high and CXCR3 high. Memory CD8+CD44 high T cells can be further sub-divided into lymphoid-tissue residing Central Memory T cells (CD62L high, CCR7 high) and non-lymphoid tissue residing Effector Memory T cells (CD62L low, CCR7 low) (Klonowski et al. Immunity 2004, 20:551-562). The isolated population of CD8+ T cells can be mixed with the PTP1B and/or antigen in any suitable container, device, cell culture media, system, etc., and can be cultured in vitro and/or exposed to the one or more antigens, and any other reagent, or cell culture media, in order to expand and/or mature and/or differentiate the T cells to have any of various desired cytotoxic T cell characteristics.

Human CD8+ T-cell types and/or populations can be identified using the phenotypic cell-surface markers CD62L, CCR7, CD27, CD28 and CD45RA or CD45RO (Sallusto F et al. Nature 1999, 401:708-712). As used herein, CD8+ T-cell types and/or populations have the following characteristics or pattern of expression of cell surface markers: Naive T cells are characterized as CD45RA+, CD27+, CD28+, CD62L+ and CCR7+; CD45RO+ Central Memory T cells are CD45RA−, CD27+, CD28+, CD62L+ and CCR7+; CD45RO+ Effector Memory T cells are defined by the lack of expression of these five markers (CD45RA−, CD27−, CD28−, CD62L− and CCR7−); and terminally differentiated Effector Memory CD45RA+ T cells are characterized as CD45RO+, CCR7−, CD27−, CD28−, CD62L−. Terminally differentiated Effector Memory cells further upregulate markers such as CD57, KLRG1, CX3CR1 and exhibit strong cytotoxic properties characterized by their ability to produce high levels of Granzyme A and B, Perforin and IFNγ. Therefore, various populations of T cells can be separated from other cells and/or from each other based on their expression or lack of expression of these markers. In this manner, the invention provides methods of separating different populations of CD8+ T cells and also separated or isolated populations of CD8+ T cells. The CD8+ T cell types described herein may also be isolated by any other suitable method known in the art; for example, if a particular antigen or antigens are used to produce antigen-specific CD8+ T cells, those cells can be separated or isolated from other cells by affinity purification using that antigen or antigens; appropriate protocols are known in the art.

Different CD8+ T cell types can also exhibit particular functions, including, for example: secretion of IFN-γ; secretion of IL-2; production of Granzyme B; expression of FasL and expression of CD 107. However, while the expression pattern of cell surface markers is considered diagnostic of each particular CD8+ T cell type and/or population as described herein, the functional attributes of each cell type and/or population may vary depending on the amount of stimulation the cell(s) has or have received.

Effector functions or properties of T cells can be determined by the effector molecules that they release in response to specific binding of their T-cell receptor with antigen:MHC complex on the target cell, or in the case of CAR T-cells interaction of the chimeric antigen receptor, e.g. scFv, with the antigen expressed on the target cell. Cytotoxic effector molecules that can be released by cytotoxic CD8+ T cells include perforin, granzymes A and B, granulysin and Fas ligand. Generally, upon degranulation, perforin inserts itself into the target cell's plasma membrane, forming a pore, granzymes are serine proteases which can trigger apoptosis (a form of cell death), granulysin induces apoptosis in target cells, and Fas ligand can also induce apoptosis. Typically, these cytotoxic effector molecules are stored in lytic granules in the cell prior to release. Other effector molecules that can be released by cytotoxic T cells include IFN-γ, TNF-β and TNF-α. IFN-γ can inhibit viral replication and activate macrophages, while TNF-β and TNF-α can participate in macrophage activation and in killing target cells. In any method of the invention, before administration or reintroduction of the cells contacted with a PTP1B inhibitor, those cells will be assessed for their cytotoxic activity by flow cytometry using fluorochrome-conjugated antibodies against surface and intracellular markers that specify cytotoxic effector T cells including Granzyme A and B, Perforin and IFNγ.

An activated T cell is a cell that is no longer in GO phase, and begins to produce one or more cytotoxins, cytokines and/or other membrane-associated markers characteristic of the cell type (e.g., CD8+) as described herein and is capable of recognizing and binding any target cell that displays the particular peptide:MHC complex or antigen alone on its surface and releasing its effector molecules.

The methods of the invention that promote the differentiation of T cells into a population of cytotoxic T cells lead to a statistically significant increase in the population of cytotoxic T cells. A population is increased when the cells are present in an amount which is at least 10%, 20%, 30%, 40%, 50%, 60%, 70%, 80%, 90%, 95%, or 100% higher in comparison to an appropriate control such as, for example, the size of the population prior to treatment with a method of the invention. The cytotoxic CD8+ T cell effector function is increased when cells have a function which is at least 10%, 20%, 30%, 40%, 50%, 60%, 70%, 80%, 90%, 95%, or 100% higher, than an appropriate control, such as, for example, the performance of a sample of cells in a particular assay in the absence of a particular event or condition. Where appropriate, in vivo function or the presence of a cell population in vivo may be measured using cells isolated from a subject in in vitro assays.

An "enriched" or "purified" population of cells is an increase in the ratio of particular cells to other cells, for example, in comparison to the cells as found in a subject's body, or in comparison to the ratio prior to exposure to a PTP1B inhibitor. In some embodiments, in an enriched or purified population of cells, the particular cells include at least 20%, 30%, 40%, 50%, 60%, 70%, 75%, 80%, 90%, 95% or 99% of the total cell population. A population of cells may be defined by one or more cell surface markers and/or properties.

CD8+ T cells exposed to, or contacted with, a PTP1B inhibitor that exhibit at least one property of a cytotoxic T cell as described herein, upon administration to the subject, elicit a cytotoxic T cell response to a tumour cell. Preferably, that CTL response to a tumour cell is effective in causing cell death, such as lysis, of tumour cells having the targeted antigen.

CD8+ T cells exposed to, or contacted with, a PTP1B inhibitor can be administered to the subject by any method including, for example, injection, infusion, deposition, implantation, oral ingestion, or topical administration, or any combination thereof. Injections can be, e.g., intravenous, intramuscular, intradermal, subcutaneous or intraperitoneal. Single or multiple doses can be administered over a given time period, depending upon the cancer, the severity thereof and the overall health of the subject, as can be determined by one skilled in the art without undue experimentation. The injections can be given at multiple locations. Administration of the CD8+ T cells can be alone or in combination with other therapeutic agents. Each dose can include about $10\times10^3$ CD8+ T cells, $20\times10^3$ cells, $50\times10^3$ cells, $100\times10^3$ cells, $200\times10^3$ cells, $500\times10^3$ cells, $1\times10^6$ cells, $2\times10^6$ cells, $20\times10^6$ cells, $50\times10^6$ cells, $100\times10^6$ cells, $200\times10^6$, $500\times10^6$, $1\times10^9$ cells, $2\times10^9$ cells, $5\times10^9$ cells, $10\times10^9$ cells, and the like. Administration frequency can be, for example, once per week, twice per week, once every two weeks, once every three weeks, once every four weeks, once per month, once every two months, once every three months, once every four months, once every five months, once every six months, and so on. The total number of days where administration occurs can be one day, on 2 days, or on 3, 4, 5, 6, 7, 8, 9, 10, 11, 12, 13, 14, 15, 16, 17, 18, 19, or 20 days, and so on. It is understood that any given administration might involve two or more injections on the same day. For administration, at least 20%, at least 30%, at least 40%, at least 50%, at least 60%, at least 70%, at least 80%, at least 90%, at least 95%, at least 99%, of the CD8+ T cells that are administered exhibit at least one property of a cytotoxic T cell.

In one illustrative embodiment, when the cells have been treated with a PTP1B inhibitor (such as a small molecule inhibitor, an inhibitor RNA or including an inhibitor in the form of CRISPR/Cas9 system for inhibiting PTP1B, a composition comprising the CD8+ T cells can be prepared and administered to the patient. In one embodiment, culture media that lacks any animal products, such as bovine serum, can be used to culture the CD8+ T cells. In another embodiment, tissue culture conditions typically used by the skilled artisan to avoid contamination with bacteria, fungi and *mycoplasma* can be used. In an exemplary embodiment, prior to being administered to a patient, the CD8+T (e.g. CAR-T cells) are pelleted, washed, and are resuspended in a pharmaceutically acceptable carrier or diluent. Exemplary compositions comprising CAR-expressing T lymphocytes (e.g., cytotoxic T lymphocytes) include compositions comprising the cells in sterile 290 mOsm saline, in infusible cryomedia (containing Plasma-Lyte A, dextrose, sodium chloride injection, human serum albumin and DMSO), in 0.9% NaCl with 2% human serum albumin, or in any other sterile 290 mOsm infusible materials. Alternatively, in another embodiment, depending on the identity of the culture medium, the CAR-T cells can be administered in the culture media as the composition, or concentrated and resuspended in the culture medium before administration. In various embodiments, the CAR-T cell composition, can be administered to the patient via any suitable means, such as parenteral administration, e.g., intradermally, subcutaneously, intramuscularly, intraperitoneally, intravenously, or intrathecally.

In further embodiments, the present application includes administration of a PTP1B inhibitor directly to an individual who is receiving or has received a treatment with CD8+ T cells. The CD8+ T cells may have been contacted with a PTP1B inhibitor prior to administration to an subject requiring treatment, according to any method described herein. Alternatively, the CD8+ T cells are administered to the subject, without receiving prior exposure or contact with a PTP1B inhibitor, and instead, the PTP1B inhibitor is administered directly to the subject.

The PTP1B inhibitor may be administered prior to, at the same time as, or after the subject receives treatment with the CD8+ T cells. Where the PTP1B inhibitor and CD8+ T cells are administered to the subject at the same time, they can be administered via the same route of administration (including in a single composition), or alternatively via different routes of administration. For example, the CD8+ T cells may be administered by injection into the blood stream of the subject, while the PTP1B inhibitor may be administered orally, or via another route of administration such as intramuscularly, intradermally, subcutaneously or intraperitoneally.

In a particularly preferred embodiment, the PTP1B inhibitor is directly administered to the subject following administration of CAR-T cells to the subject, for the purpose of enhancing the efficacy of the CAR-T treatment. The inhibitor can be subsequently administered once every two weeks, or once or twice weekly, or more, to facilitate CAR-T cell expansion and the formation of memory CAR-T cells.

In particularly preferred embodiments, the PTP1B inhibitor is trodusquemine, administered by injection, or a derivative (for example DPM-1001) administered orally before, during or after intravenous administration of CAR-T cells.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals. Therefore, the general term “subject” or “subject to be/being treated” is understood to include all animals (such as humans, apes, dogs, cats, horses, and cows) that require an enhanced immune response, for example subjects having cancer.

As used herein, the term “ex vivo” or “ex vivo therapy” refers to a therapy where cells are obtained from a patient or a suitable alternate source, such as, a suitable allogenic donor, and are modified, such that the modified cells can be used to treat a disease which will be improved by the therapeutic benefit produced by the modified cells.

Treatment includes the administration or re-introduction of the modified cells into the patient. A benefit of ex vivo therapy is the ability to provide the patient the benefit of the treatment, without exposing the patient to undesired collateral effects from the treatment.

The term “administered” means administration of a therapeutically effective dose of the aforementioned composition including the respective cells to an individual. By “therapeutically effective amount” is meant a dose that produces the effects for which it is administered. The exact dose will depend on the purpose of the treatment, and will be ascertainable by one skilled in the art using known techniques. As is known in the art and described above, adjustments for systemic versus localized delivery, age, body weight, general health, sex, diet, time of administration, drug interaction and the severity of the condition may be necessary, and will be ascertainable with routine experimentation by those skilled in the art.

Subjects requiring treatment include those already having a benign, pre-cancerous, or non-metastatic tumour as well as those in which the occurrence or recurrence of cancer is to be prevented. Subjects may have metastatic cells, including metastatic cells present in the ascites fluid and/or lymph node.

The objective or outcome of treatment may be to reduce the number of cancer cells; reduce the primary tumour size; inhibit (i.e., slow to some extent and preferably stop) cancer cell infiltration into peripheral organs; inhibit (i.e., slow to some extent and preferably stop) tumour metastasis; inhibit, to some extent, tumour growth; and/or relieve to some extent one or more of the symptoms associated with the disorder.

Efficacy of treatment can be measured by assessing the duration of survival, time to disease progression, the response rates (RR), duration of response, and/or quality of life.

The method is particularly useful for extending time to disease progression.

The method is particularly useful for extending survival of the human, including overall survival as well as progression free survival.

The method is particularly useful for providing a complete response to therapy whereby all signs of cancer in response to treatment have disappeared. This does not always mean the cancer has been cured.

The method is particularly useful for providing a partial response to therapy whereby there has been a decrease in the size of one or more tumours or lesions, or in the extent of cancer in the body, in response to treatment.

The objective or outcome of treatment may be any one or more of the following:

to reduce the number of cancer cells;

reduce the primary tumour size;

inhibit (i.e., slow to some extent and preferably stop) cancer cell infiltration into peripheral organs;

inhibit (i.e., slow to some extent and preferably stop) tumour metastasis;

inhibit, to some extent, tumour growth;

relieve to some extent one or more of the symptoms associated with the disorder.

In one embodiment, animals requiring treatment include those having a benign, pre-cancerous, non-metastatic tumour.

In one embodiment, the cancer is pre-cancerous or pre-neoplastic.

In one embodiment, the cancer is a secondary cancer or metastases. The secondary cancer may be located in any organ or tissue, and particularly those organs or tissues having relatively higher hemodynamic pressures, such as lung, liver, kidney, pancreas, bowel and brain. The secondary cancer may be detected in the ascites fluid and/or lymph nodes.

In one embodiment, the cancer may be substantially undetectable.

"Pre-cancerous" or "pre-neoplasia" generally refers to a condition or a growth that typically precedes or develops into a cancer. A "pre-cancerous" growth may have cells that are characterized by abnormal cell cycle regulation, proliferation, or differentiation, which can be determined by markers of cell cycle.

In one embodiment, the cancer is pre-cancerous or pre-neoplastic.

In one embodiment, the cancer is a secondary cancer or metastases. The secondary cancer may be located in any organ or tissue, and particularly those organs or tissues having relatively higher hemodynamic pressures, such as lung, liver, kidney, pancreas, bowel and brain.

In one embodiment, the cancer expresses the cell surface tumour antigen Her-2.

An example of a cancer that expresses the cell surface tumour antigen Her-2 is a sarcoma.

Other examples of cancer include blastoma (including medulloblastoma and retinoblastoma), sarcoma (including liposarcoma and synovial cell sarcoma), neuroendocrine tumours (including carcinoid tumours, gastrinoma, and islet cell cancer), mesothelioma, schwannoma (including acoustic neuroma), meningioma, adenocarcinoma, melanoma, leukemia or lymphoid malignancies, lung cancer including small-cell lung cancer (SCLC), non-small cell lung cancer (NSCLC), adenocarcinoma of the lung and squamous carcinoma of the lung, epidermoid lung cancer, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer (including metastatic breast cancer), colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, testicular cancer, esophagael cancer, tumours of the biliary tract, as well as head and neck cancer.

Pre-neoplastic, neoplastic and metastatic diseases are particular examples to which the methods of the invention may be applied. Broad examples include breast tumours, colorectal tumours, adenocarcinomas, mesothelioma, bladder tumours, prostate tumours, germ cell tumour, hepatoma/cholangio, carcinoma, neuroendocrine tumours, pituitary neoplasm, small round cell tumour, squamous cell cancer, melanoma, atypical fibroxanthoma, seminomas, nonseminomas, stromal leydig cell tumours, Sertoli cell tumours, skin tumours, kidney tumours, testicular tumours, brain tumours, ovarian tumours, stomach tumours, oral tumours, bladder tumours, bone tumours, cervical tumours, esophageal tumours, laryngeal tumours, liver tumours, lung tumours, vaginal tumours and Wilms' tumour.

Examples of particular cancers include but are not limited to adenocarcinoma, adenoma, adenofibroma, adenolymphoma, adontoma, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, ameloblastoma, angiokeratoma, angiolymphoid hyperplasia with eosinophilia, angioma sclerosing, angiomatosis, apudoma, anal cancer, angiosarcoma, aplastic anaemia, astrocytoma, ataxia-telangiectasia, basal cell carcinoma (skin), bladder cancer, bone cancers, bowel cancer, brain stem glioma, brain and CNS tumours, breast cancer, branchioma, CNS tumours, carcinoid tumours, cervical cancer, childhood brain tumours, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, carcinoma (e.g. Walker, basal cell, basosquamous, Brown-Pearce, ductal, Ehrlich tumour, Krebs 2, Merkel cell, mucinous, non-small cell lung, oat cell, papillary, scirrhous, bronchiolar, bronchogenic, squamous cell, and transitional cell), carcinosarcoma, cervical dysplasia, cystosarcoma phyllodes, cementoma, chordoma, choristoma, chondrosarcoma, chondroblastoma, craniopharyngioma, cholangioma, cholesteatoma, cylindroma, cystadenocarcinoma, cystadenoma, dermatofibrosarcoma-protuberans, desmoplastic-small-round-cell-tumour, ductal carcinoma, dysgerminoam, endocrine cancers, endometrial cancer, ependymoma, esophageal cancer, Ewing's sarcoma, extra-hepatic bile duct cancer, eye cancer, eye: melanoma, retinoblastoma, fallopian tube cancer, fanconi anaemia, fibroma, fibrosarcoma, gall bladder cancer, gastric cancer, gastrointestinal cancers, gastrointestinal-carcinoid-tumour, genitourinary cancers, germ cell tumours, gestationaltrophoblastic-disease, glioma, gynaecological cancers, giant cell tumours, ganglioneuroma, glioma, glomangioma, granulosa cell tumour, gynandroblastoma, haematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, hamartoma, hemangioendothelioma, hemangioma, hemangiopericytoma, hemangiosarcoma, hemangiosarcoma, histiocytic disorders, histiocytosis malignant, histiocytoma, hepatoma, hidradenoma, hondrosarcoma, immunoproliferative small, opoma, ontraocular melanoma, islet cell cancer, Kaposi's sarcoma, kidney cancer, langerhan's cell-histiocytosis, laryngeal cancer, leiomyosarcoma, leukemia, li-fraumeni syndrome, lip cancer, liposarcoma, liver cancer, lung cancer, lymphedema, lymphoma, Hodgkin's lymphoma, non-Hodgkin's lymphoma, leiomyosarcoma, leukemia (e.g. B-cell, mixed cell, null-cell, T-cell, T-cell chronic, HTLV-II associated, lymphangiosarcoma, lymphocytic acute, lymphocytic chronic, mast-cell and myeloid), leukosarcoma, leydig cell tumour, leiomyoma, lymphangioma, lymphangiocytoma, lymphangioma, lymphangiomyoma, lymphangiosarcoma, male breast cancer, malignant-rhabdoid-tumour-of-kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, malignant carcinoid syndrome carcinoid heart disease, meningioma, melanoma, mesenchymoma, mesonephroma, myoblastoma, myoma, myosarcoma, myxoma, myxosarcoma, nasal cancer, nasopharyngeal cancer, nephroblastoma, rieuroblastoma, neurofibromatosis, Nijmegen breakage syndrome, non-melanoma skin cancer, non-small-cell-lung-cancer-(nscic), neurilemmoma, neuroblastoma, neuroepithelioma, neurofibromatosis, neurofibroma, neuroma, neoplasms (e.g. bone, breast, digestive system, colorectal, liver), ocular cancers, oesophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal-tumours, pituitary cancer, polycythemia vera, prostate cancer, osteoma, osteosarcoma, ovarian carcinoma, papilloma, paraganglioma, paraganglioma nonchromaffin, pinealoma, plasmacytoma, protooncogene, rare-cancers-and-associated-disorders, renal cell carcinoma, retinoblastoma, rhabdomyosarcoma, Rothmund-Thomson syndrome, reticuloendotheliosis, rhabdomyoma, salivary gland cancer, sarcoma, schwannoma, Sezary syndrome, skin cancer, small cell lung cancer (sclc), small intestine cancer, soft tissue sarcoma, spinal cord tumours, squamous-cell-carcinoma-(skin), stomach cancer, synovial sarcoma, sarcoma (e.g. Ewing's experimental, Kaposi's and mast-cell sarcomas), Sertoli cell tumour, synovioma, testicular cancer, thymus cancer, thyroid cancer, transitional-cell-cancer-(bladder), transitional-cell-cancer-(renal-pelvis-/-ureter), trophoblastic cancer, teratoma, theca cell tumour, thymoma, trophoblastic tumour, urethral cancer, urinary system cancer, uroplakins, uterine sarcoma, uterus cancer, vaginal cancer, vulva cancer, Waldenstrom's macroglobulinemia and Wilms' tumour.

It will be understood that the invention disclosed and defined in this specification extends to all alternative combinations of two or more of the individual features mentioned or evident from the text or drawings. All of these different combinations constitute various alternative aspects of the invention.

EXAMPLES

Example 1: Loss of Ptp1b Increases Overall Cellularity of T Cells without Affecting CD4/CD8 T Cells Development in Thymus Ptpn1$^{fl/fl}$ mice have previously been described previously (Bence et al., 2006 Nature Medicine 12, 917-24). To delete PTP1B in T cells we crossed Ptp1b$^{fl/fl}$ mice Lck-Cre transgenic to generate Lck-Cre;Ptpn1$^{fl/fl}$ mice.

Lck-Cre;Ptpn1$^{fl/fl}$ mice (n=8) and wild-type counter parts (n=8) were sacrificed at age of 8 weeks old. Single cells from thymus and various lymphoid organs were isolated for FACS analysis.

Figure 1:
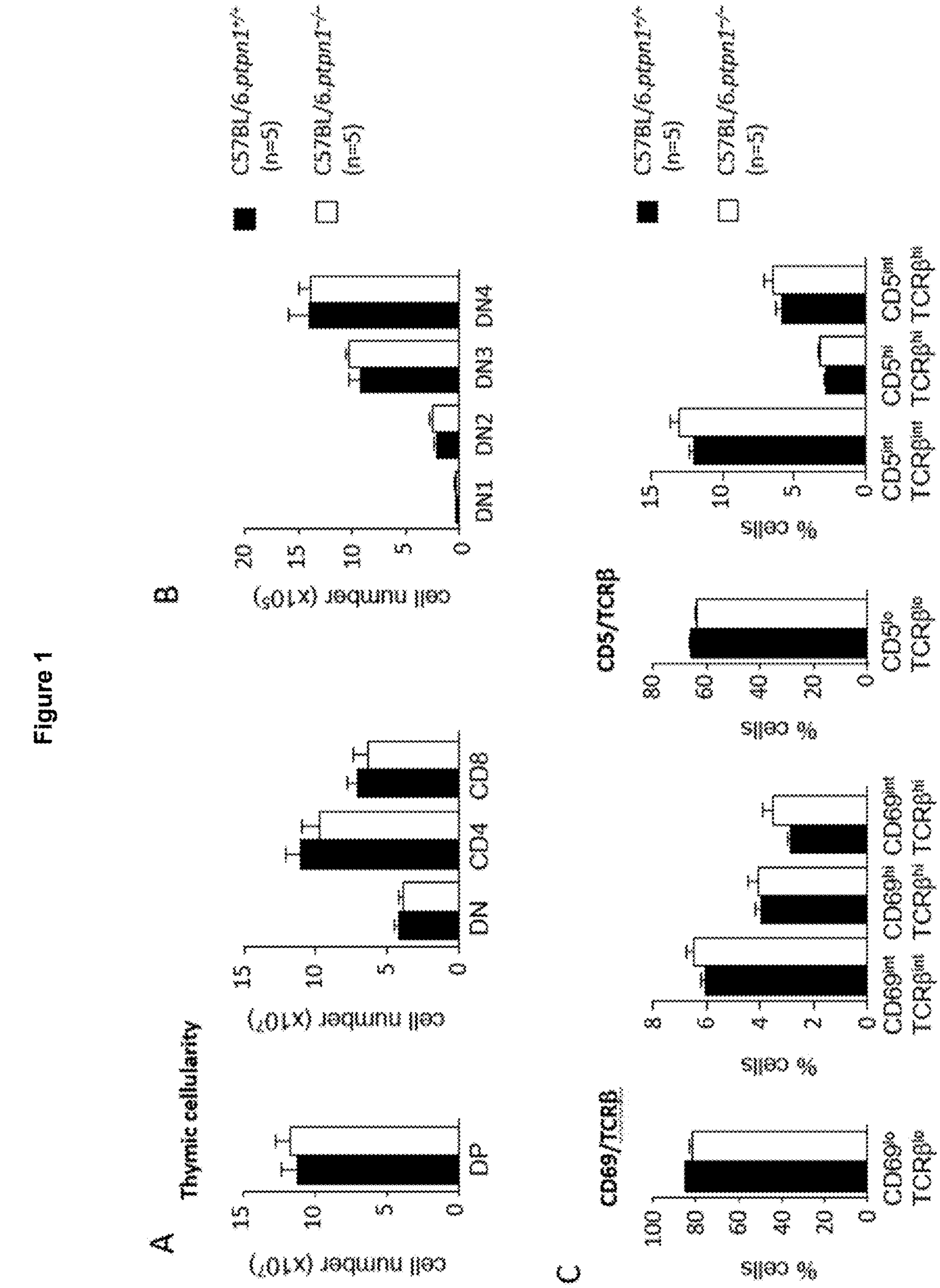
FIG. 1. Thymocyte development in C57BL/6.Ptpn1$^{-/-}$ mice. C57BL/6.Ptpn1$^{+/+}$ and C57BL/6.Ptpn1$^{-/-}$ thymocytes from 7 week old mice were stained with fluorochrome-conjugated antibodies against A) CD4 and CD8, B) Lineage markers (CD4, CD8, CD3, Gr-1, B220, CD19, CD11b, CD11c, NK1.1, TER119), CD25, CD44 and c-KIT, and C) TCRP, CD69 and CD5 and analysed by flow cytometry. A) Cells were gated for CD4$^{+}$, CD8$^{+}$, CD4$^{+}$/CD8$^{+}$ (DP) and CD4$^{-}$/CD8$^{-}$ (DN) thymocyte subsets and absolute numbers determined. B) Cells were gated for. Lineage-CD25$^{lo}$CD44$^{hi}$KIT$^{hi}$ (DN1), Lineage-CD25$^{hi}$CD44$^{hi}$KIT$^{hi}$ (DN2), Lineage-CD25$^{hi}$CD44$^{lo}$KIT$^{lo}$ (DN3), Lineage-CD25$^{lo}$CD44$^{lo}$KIT$^{lo}$ (DN4) and absolute numbers determined. C) Cells were gated for the different developmental stages (labelled 1-4) according to the expression of the positive selection markers CD69, CD5 and TCRβ and percentages were determined. Results in (A-C) are means±SEM from the indicated number of mice.
Figure 2:
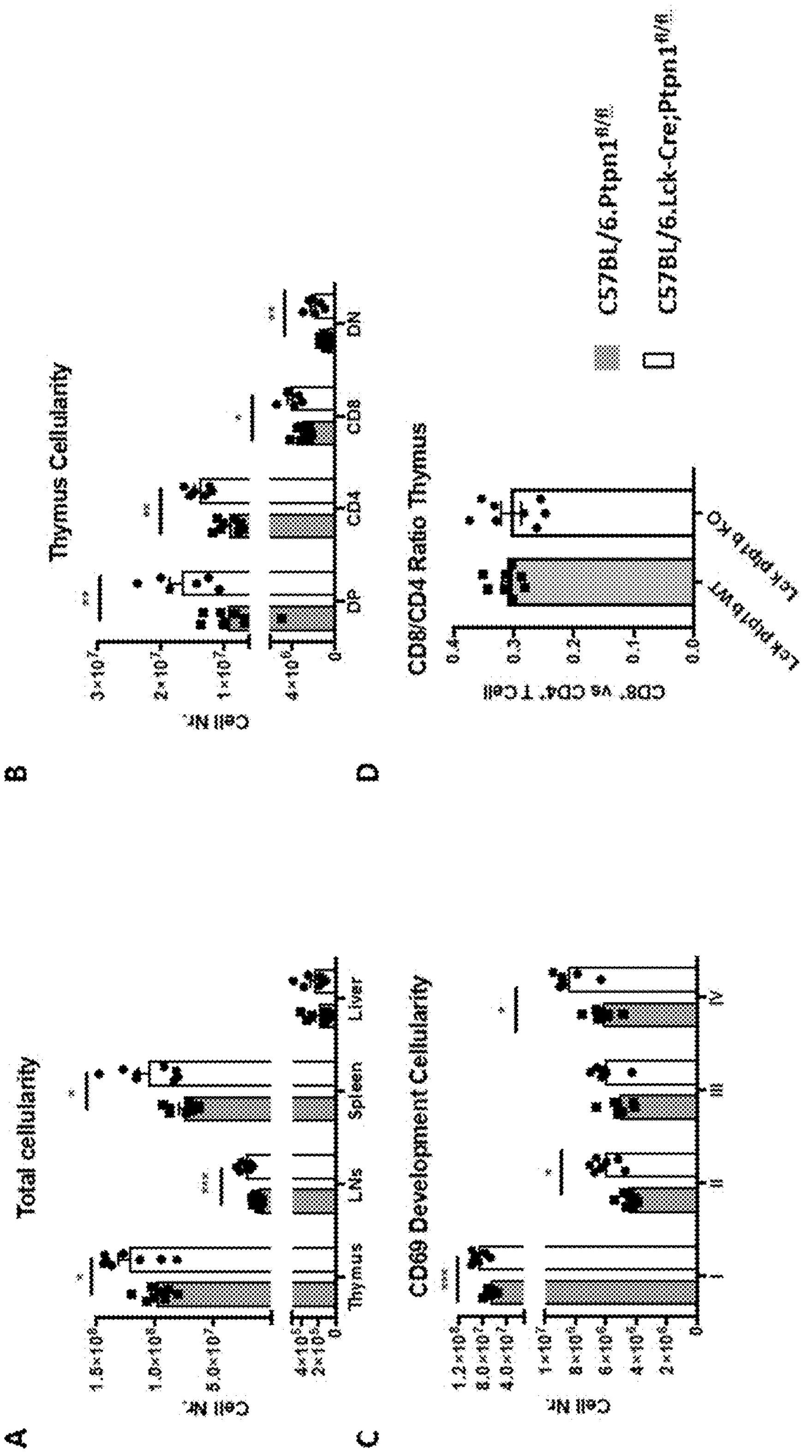
FIG. 2. T cell-specific PTP1B-deletion increases thymic cellularity without developmental impact on CD4/CD8 lineage commitment. Single cell suspensions from 8 week old C57BL/6.Lck-Cre;Ptpn1$^{fl/fl}$ mice (n=8) and C57BL/6.Ptpn1$^{fl/fl}$ (n=8) mice were prepared from thymus, lymph nodes (LNs), spleens, and livers. Cells were stained with fluorochrome-conjugated antibodies in FACS buffer (D-PBS containing 2% fetal bovine serum) for 30 minutes at room temperature. Cells were washed twice with FACS buffer and analyzed by flow cytometry. A) Total cellularity was increased in thymus (p=0.0499), lymph nodes (p=0.0003), and spleen (p=0.0207) of C57BL/6.Lck-Cre;Ptpn1$^{fl/fl}$ mice. B) Cellularity was increased in C57BL/6.Lck-Cre;Ptpn1$^{fl/fl}$ double-positive (DP) thymocytes (p=0.008), double-negative (DN) thymocytes (p=0.008), CD4$^{+}$ thymocytes (p=0.0013), and CD8$^{+}$ thymocytes (p=0.0293). C) Cellularity was increased at various stages of thymocyte development (p=0.002, p=0.001, p=0.053, p=0.001) in C57BL/6.Lck-Cre;Ptpn1$^{fl/fl}$ mice. D) CD8$^{+}$/CD4$^{+}$ thymocyte ratio was not altered in C57BL/6.Lck-Cre;Ptpn1$^{fl/fl}$ mice (p=0.7984). Results shown are means±SEM and are representative of two independent experiments; significances were determined using 2-tailed Mann-Whitney U Test.
Figure 3:
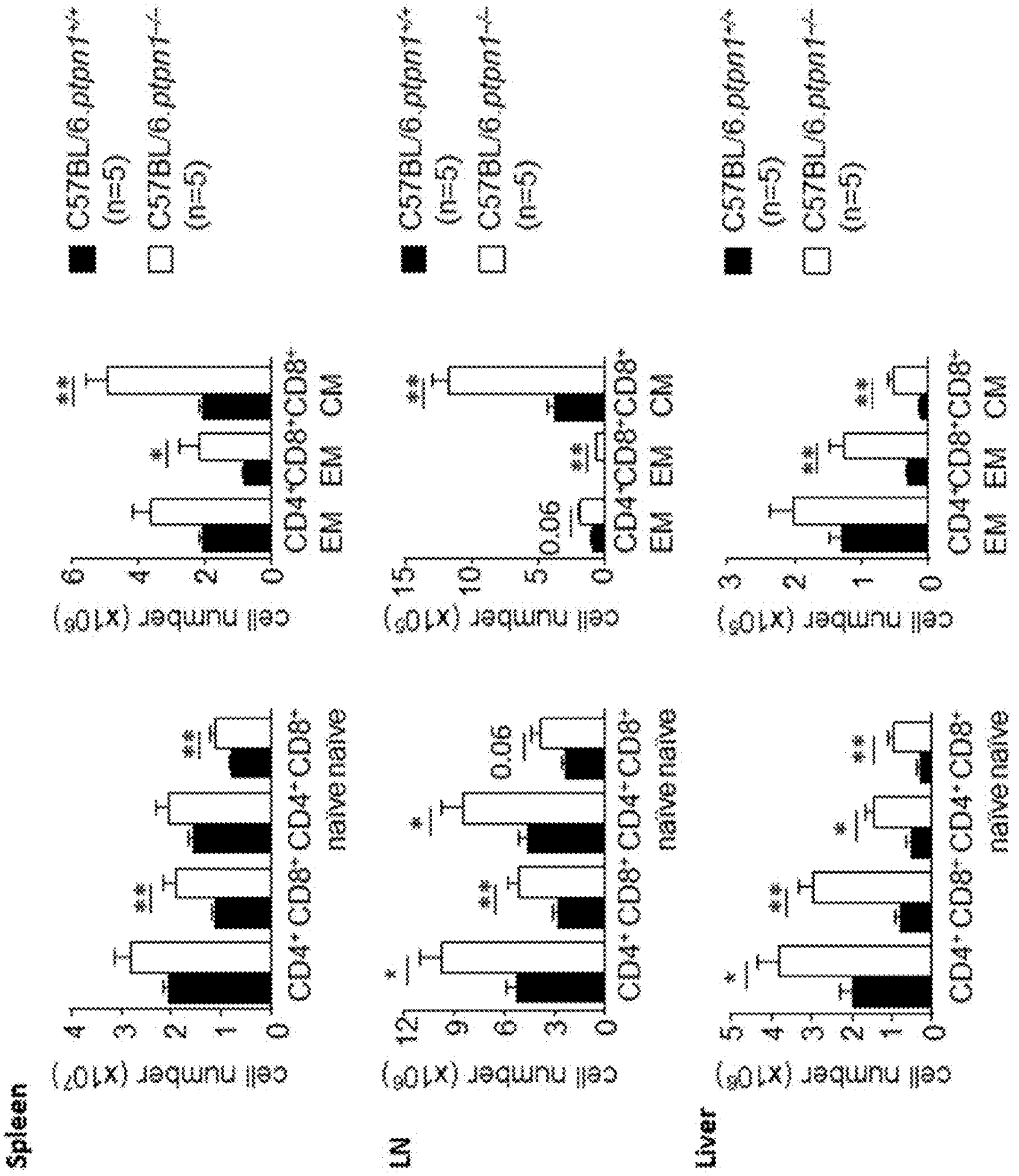
FIG. 3. T cell subsets in C57BL/6.Ptpn1$^{-/-}$ mice. C57BL/6.Ptpn1$^{+/-}$ and C57BL/6.Ptpn1$^{-/-}$ lymphocytes isolated from spleen, lymph nodes and liver of 7 week old mice were stained with fluorochrome-conjugated antibodies against CD4, CD8, CD44 and CD62L and analyzed by flow cytometry. Absolute numbers of total CD4$^{+}$ or CD8$^{+}$ T cells and CD4$^{+}$ versus CD8$^{+}$ naïve (CD44$^{lo}$CD62L$^{hi}$) and effector/memory-like (CD44$^{hi}$CD62L$^{lo}$; EM) and central/memory-like (CD44$^{hi}$CD62L$^{hi}$; CM) T cells were determined. Results shown are means±SEM; significance determined using 2-tailed Mann-Whitney U Test; *p<0.05, **p<0.01.

FIG. 2(A) shows that the total cellularity were increased in thymus (p=0.0499), lymph nodes (p=0.0003), and spleen (p=0.0207). Cellularity was increased in double-positive (DP) thymocytes (p=0.008), double-negative (DN) thymocytes (p=0.008), CD4+ thymocytes (p=0.0013), and CD8+ thymocytes (p=0.0293) (FIG. 2B).

Meanwhile, increased cellularity was also discovered among various stages of development (p=0.002, p=0.001, p=0.053, p=0.001) (FIG. 2C). However, the ratio between CD4$^{+}$ and CD8+ T cells remains similar (p=0.7984). (FIG. 2D).

Statistics was performed with Mann-Whitney test. Charts were representative from two independent experiments.

Example 2: Loss of Ptp1b Increases Cellularity of Various T Cell Subpopulations in Periphery Lck-Cre;Ptpn1$^{fl/fl}$ mice (n=8) and wild-type counter parts (n=8) were sacrificed at age of 8 weeks. Single cells from thymus and various lymphoid organs were isolated as for Example 1.

Figure 4:
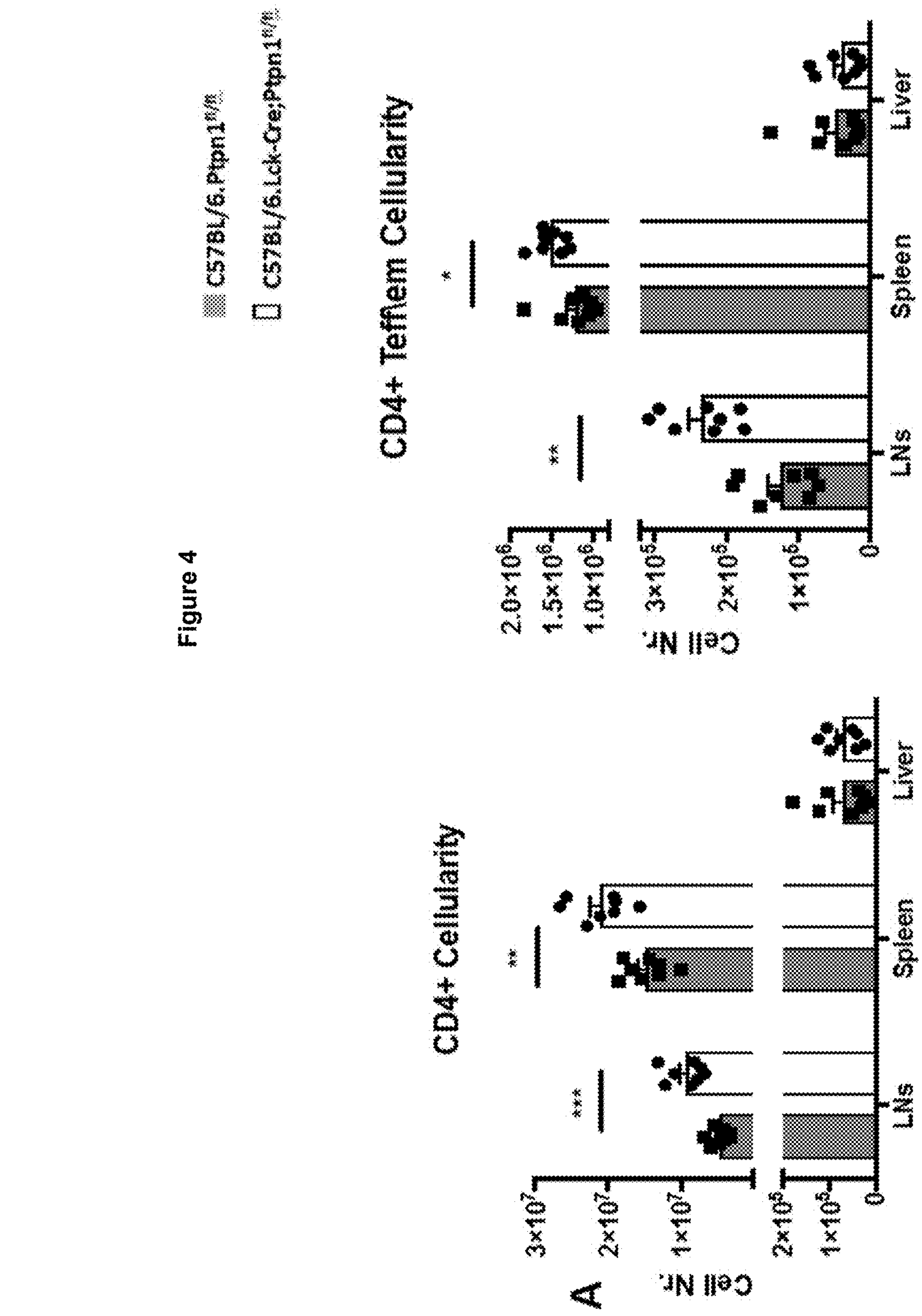
FIG. 4. T cell specific PTP1B-deficiency increases cellularity of memory T cell populations in periphery. Single cell suspensions from 8 week old C57BL/6.Lck-Cre;Ptpn1$^{fl/fl}$ mice (n=8) and C57BL/6.Ptpn1$^{fl/fl}$ (n=8) mice were prepared from thymus, lymph nodes, spleens and livers. Cells were stained with fluorochrome-conjugated antibodies FACS buffer for 30 minutes at room temperature. Cells were washed twice with FACS buffer and analyzed by flow cytometry. A-B) Total CD4$^{+}$ and CD8$^{+}$ T cells including naïve, effector/memory and central/memory T cells were significantly increased in lymph nodes and spleens from C57BL/6.Lck-Cre;Ptpn1$^{fl/fl}$ mice. C) CD4$^{+}$ CD185$^{+}$GL-7$^{+}$ germinal center follicular helper T cells were significantly increased in lymph nodes (p=0.0047) and spleens (p=0.0379) of C57BL/6.Lck-Cre;Ptpn1$^{fl/fl}$ mice. B cell numbers were significantly increased in lymph nodes (p=0.0011) and spleens (p=0.0006) from C57BL/6.Lck-Cre;Ptpn1$^{fl/fl}$ mice. D) CD4$^{+}$ CD25$^{+}$FoxP3$^{+}$ regulatory T cells were significantly increased in lymph nodes (p=0.0002), spleen (p=0.0019), and thymus (p=0.0281) from C57BL/6.Lck-Cre;Ptpn1$^{fl/fl}$ mice. Results shown are means±SEM and are representative of two independent experiments; significances were determined using 2-tailed Mann-Whitney U Test.
Figure 4:
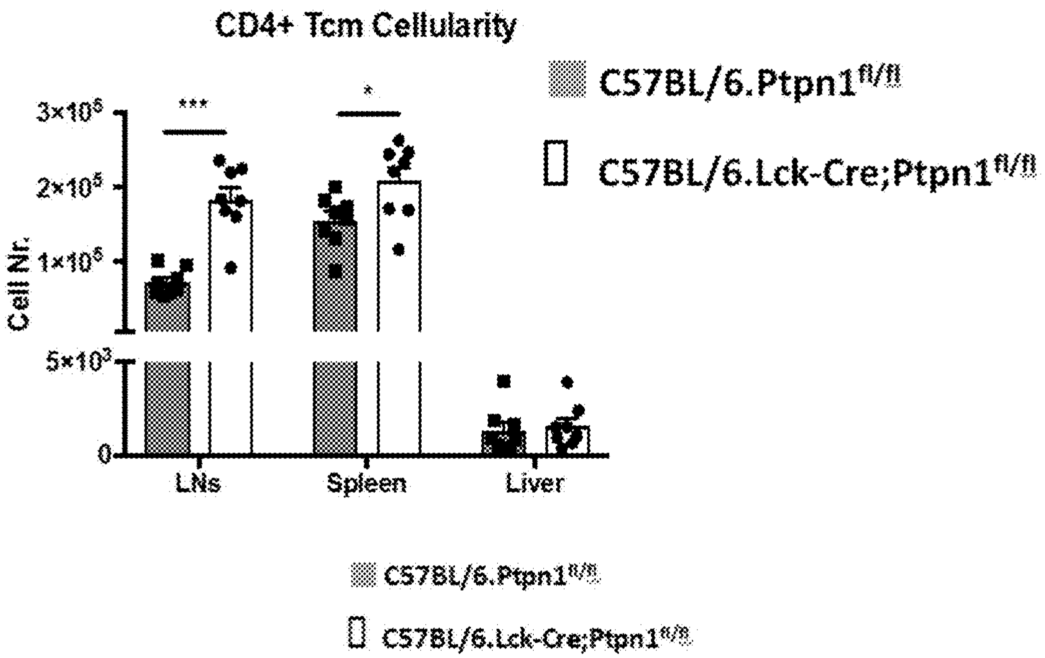
Figure 4:
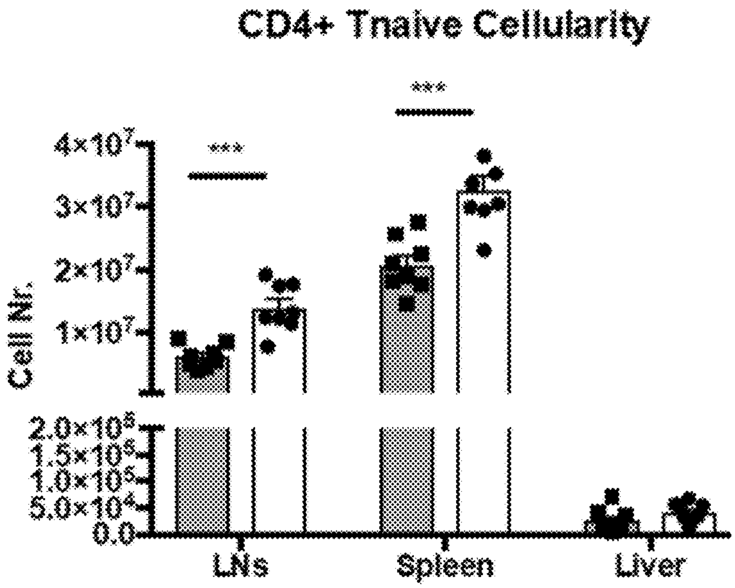
Figure 4:
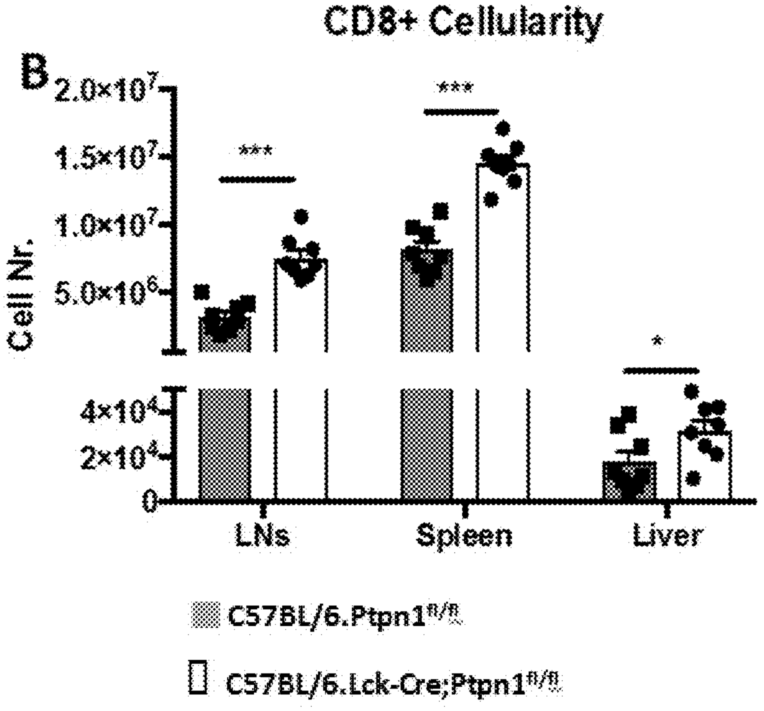
Figure 4:
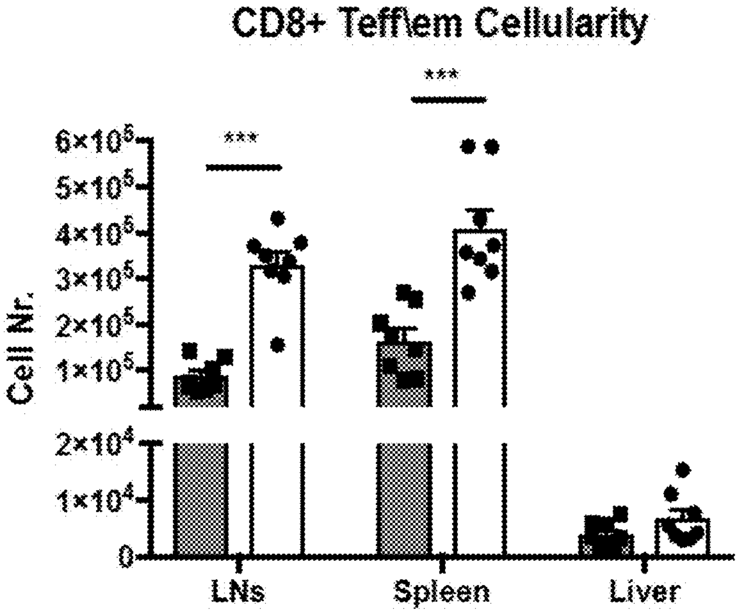
Figure 4:
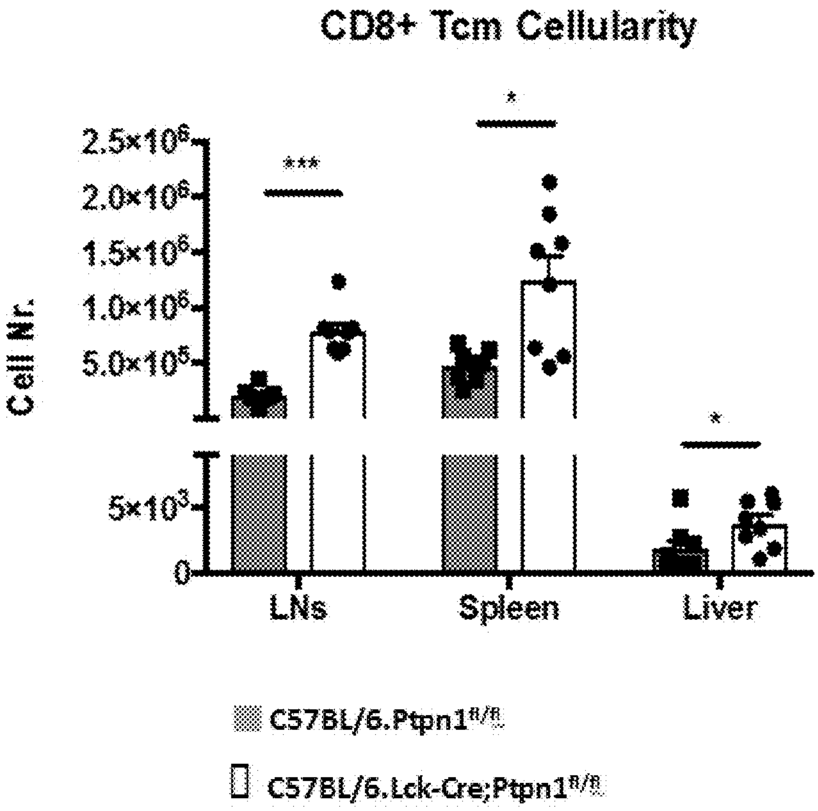
Figure 4:
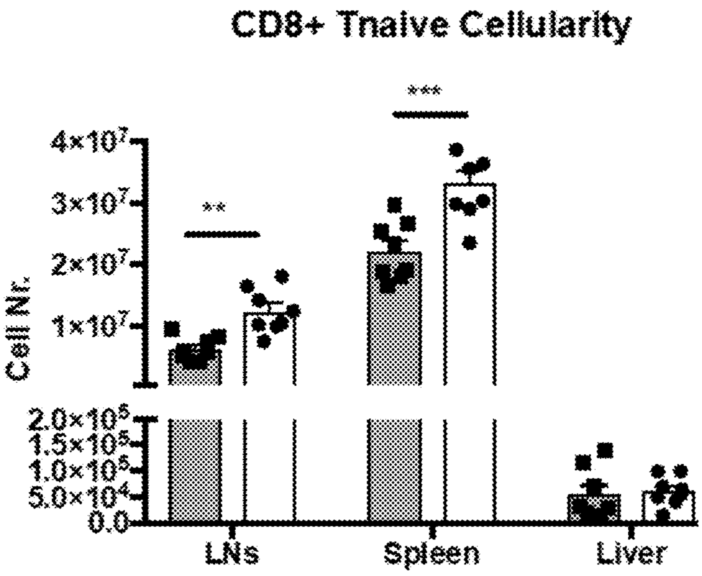
Figure 4:
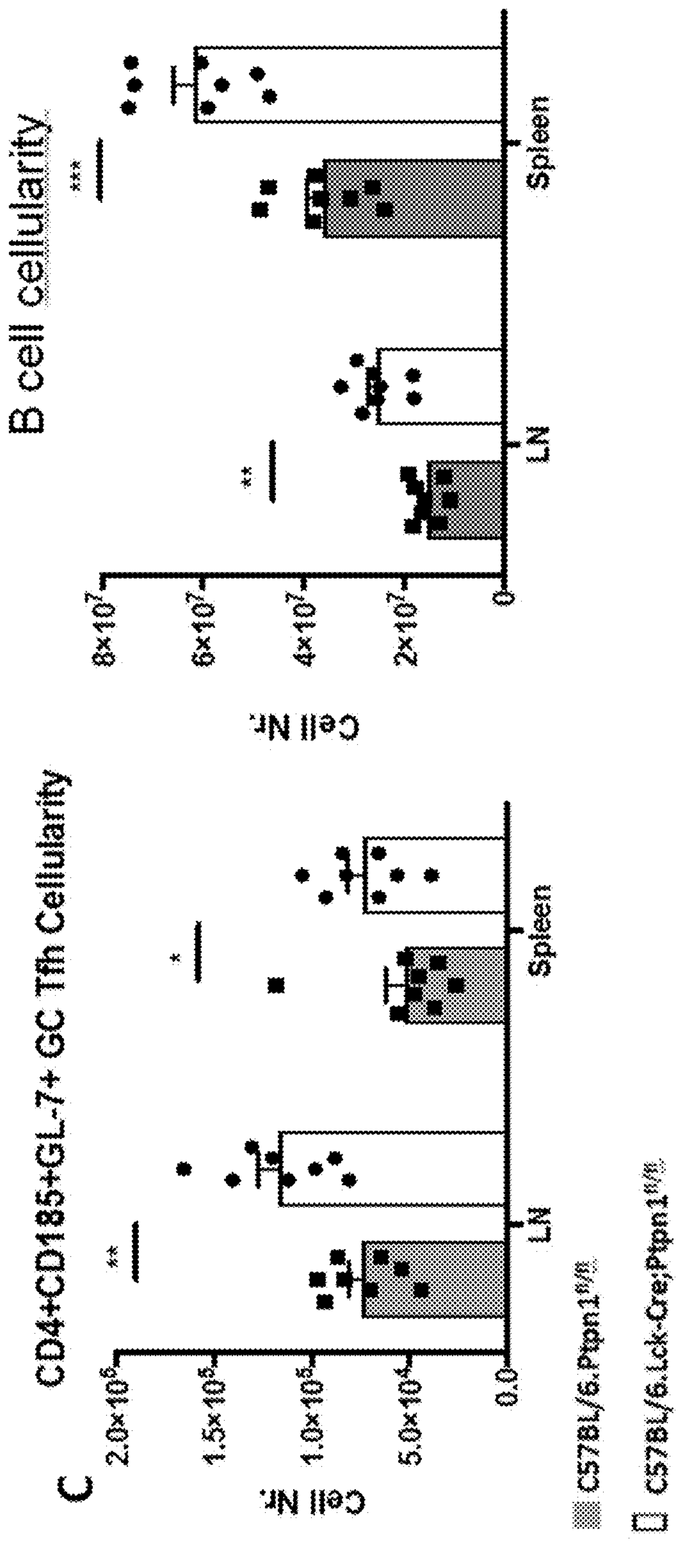
Figure 4:
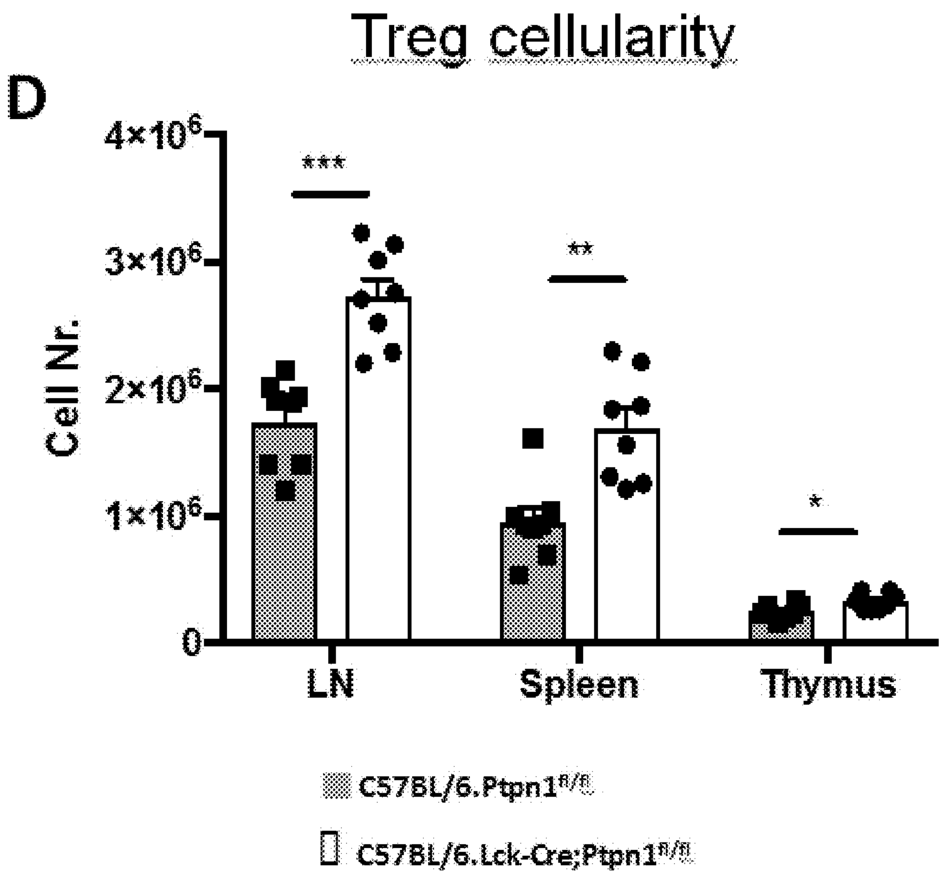
Figure 5:
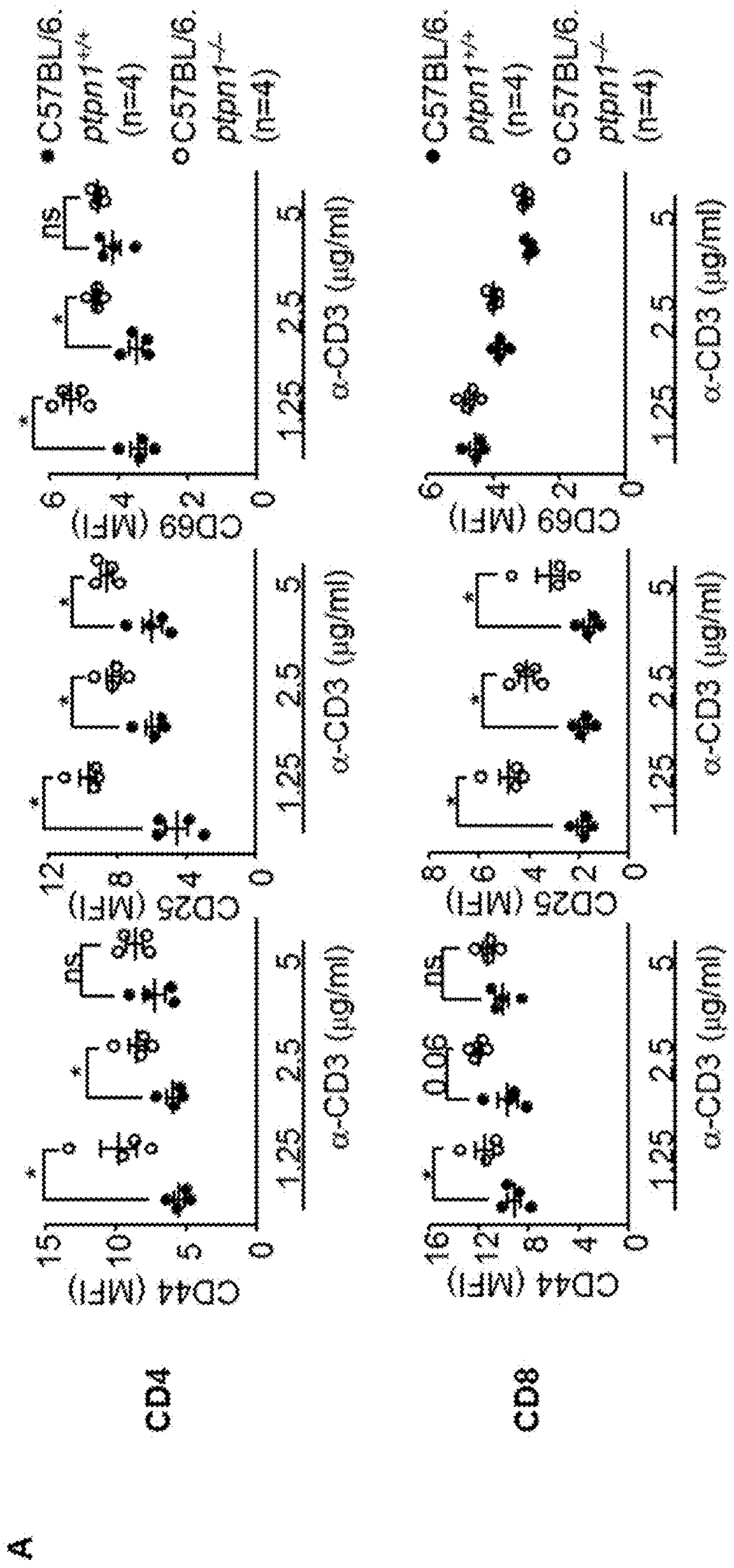
FIG. 5. PTP1B-deficiency enhances TCR mediated activation. A) FACS-purified CD8$^{+}$ naïve (CD44$^{lo}$CD62L$^{hi}$) and CD4$^{+}$ naïve (CD25$^{lo}$CD44$^{lo}$CD62L$^{hi}$) splenic T cells (2×10$^{5}$) from 7 week old C57BL/6.Ptpn1$^{+/+}$ and C57BL/6.Ptpn1$^{-/-}$ mice were stimulated with plate bound α-CD3ε and α-CD28 (1.25 μg/ml) for 48 h. Cells harvested and stained with fluorochrome-conjugated antibodies against CD44, CD25, CD62L and CD69. Cells were analyzed by flow cytometry and the indicated mean fluorescence intensities (MFI) determined; units shown are arbitrary (AU). B) FACS-purified CD8$^{+}$ naïve (CD44$^{lo}$CD62L$^{hi}$) and CD4$^{+}$ naïve (CD25$^{lo}$CD44$^{lo}$CD62L$^{hi}$) splenic T cells (2×10$^{5}$) from 7 week old C57BL/6.Lck-Cre;Ptpn1$^{fl/fl}$ mice (n=5) and C57BL/6.Ptpn1$^{fl/fl}$ mice (n=5) were isolated and stimulated with α-CD3 (1.25 μg/ml) and α-CD28 (1.25 μg/ml) antibodies for 48 hours. Activation markers CD25, CD44, and CD69 were significantly increased on C57BL/6.Lck-Cre;Ptpn1$^{fl/fl}$ CD4$^{+}$ (p<0.0001; p<0.0001; p<0.0001) and CD8$^{+}$ T cells (p<0.0001; p<0.0001; p<0.0001). Results shown are means±SEM and are representative of two independent experiments; significances were determined using 2-tailed Mann-Whitney U Test; *p<0.05.
Figure 5:
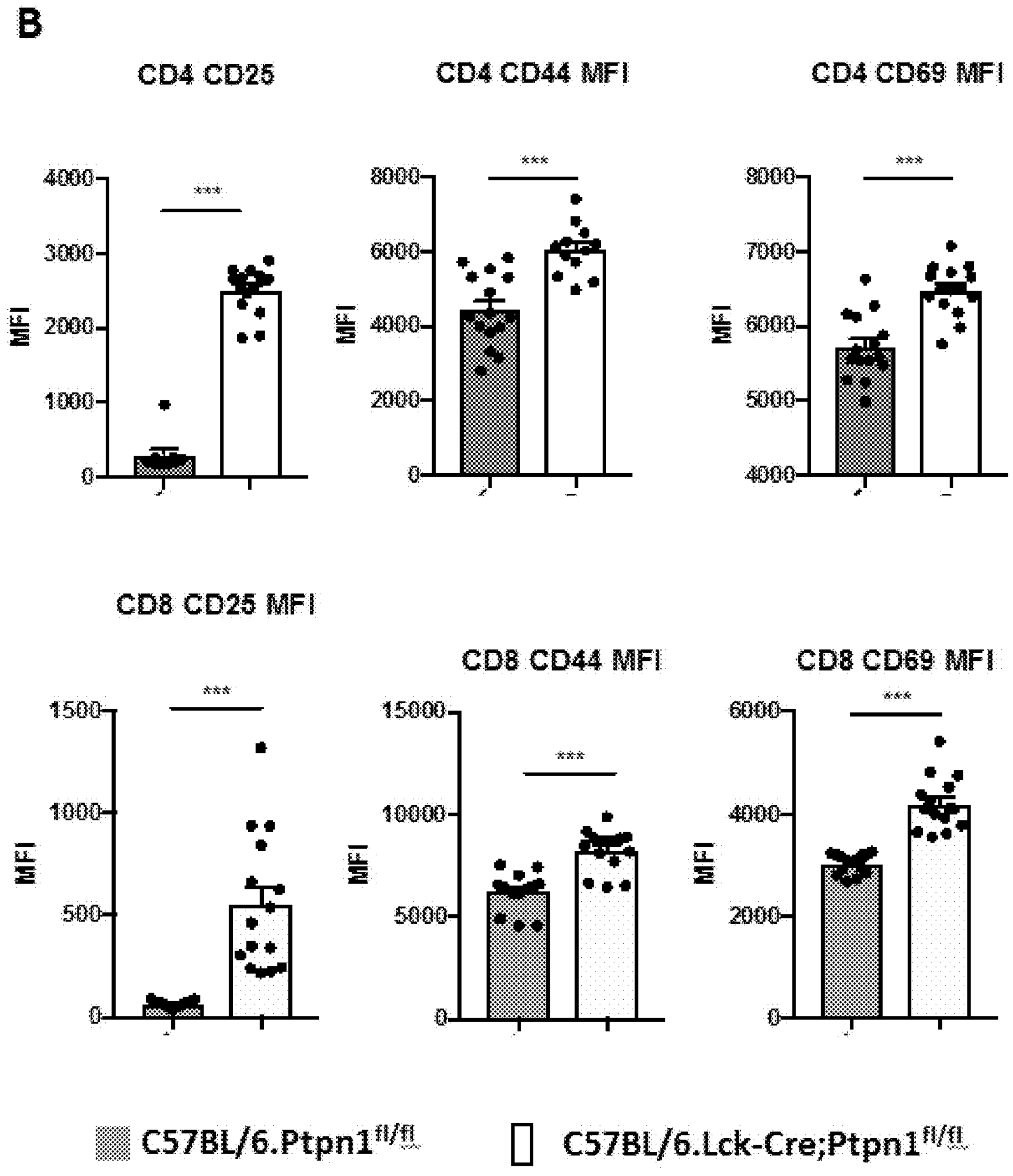

FIG. 4 (A-B) shows the cellularity of both total CD4$^{+}$ and CD8+ T cells, along with either effector\effector memory or central memory subpopulations within, was increased in lymph nodes and spleens. FIG. 4C shows cell number of germinal center follicular helper T cells were increased in lymph nodes (p=0.0047) and spleens (p=0.0379). Meanwhile the number of B cells also increased in lymph nodes (p=0.0011) and spleens (p=0.0006).

In addition, γδT cells was increased in spleen (p=0.003). CD4$^{+}$ CD25$^{+}$FoxP3$^{+}$ regulatory T cells were increased in number in lymph nodes (p=0.0002), spleen (p=0.0019), and thymus (p=0.0281). (FIG. 4D).

Statistics was performed with Mann-Whitney test. Charts were representative from two independent experiments.

Example 3: Loss of Ptp1b Enhances TCR Signaling and Activation of T Cells

Lymphoid cells from Lck-Cre;Ptpn1$^{fl/fl}$ mice (n=5) and wild-type counter parts (n=5) were isolated and stimulated with anti-CD3 (1.25 ug/ml) and anti-CD28 (1.25 ug/ml) antibodies for 48 hours.

Activation markers CD25, CD44, and CD69 were all significantly up-regulated among Lck-Cre;Ptpn1$^{fl/fl}$ CD4$^{+}$ or CD8$^{+}$ T cells. CD62L was on the other way round significantly decreased.

When stimulated with anti-CD3 (1 μg/ml) antibodies, phosphorylation of ERK was significantly enhanced in CD4$^{+}$ T cells but not CD8$^{+}$ T cells.

Statistics was performed with Mann-Whitney test for activation markers and with 2-way ANOVA analysis for phosphorylation. Charts were representative from two independent experiments.

Example 4: Loss of Ptp1b Enhances Cytokine Signaling in T Cells

Figure 12:
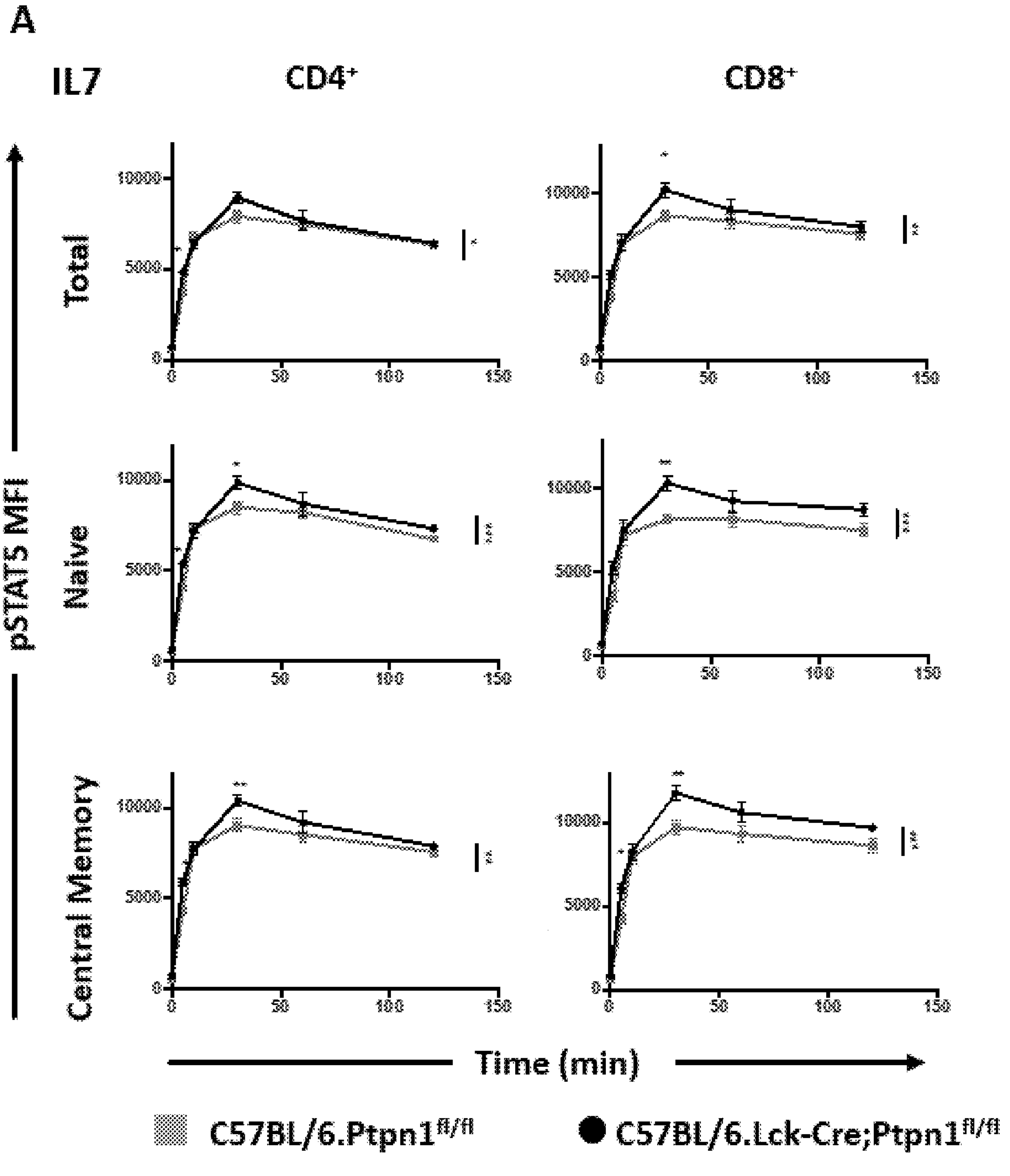
FIG. 12. PTP1B-deficiency enhances cytokine signaling in T cells. CD4$^{+}$ and CD8$^{+}$ naïve (CD44$^{lo}$CD62L$^{hi}$) or central memory ($CD44^{hi}CD44^{hi}$) lymph node T cells ($2\times10^5$) from 7 week old C57BL/6.Lck-Cre;Ptpn1$^{fl/fl}$ (n=5) and C57BL/6.Ptpn1$^{fl/fl}$ (n=5) mice were incubated with A) 5 ng/ml IL-7 and B) 5 ng/ml IL-15 for indicated time points at 37° C. A) IL-7 mediated Stat5 phosphorylation was enhanced in PTP1B-deficient $CD4^+$ and $CD8^+$ T cells and $CD4^+$ or $CD8^+$ naïve and central memory T cells (CD4 subpopulations: Total: p=0.0219, naïve: p=0.0007, central/memory: p=0.0005); (CD8 subpopulations: Total: p=0.0022, naïve: p<0.0001, central/memory: p<0.0001). B) IL-15 mediated Stat5 phosphorylation was enhanced in PTP1B-deficient $CD4^+$ and $CD8^+$ T cells and $CD4^+$ or $CD8^+$ naïve and central memory T cells (CD4 subpopulations: Total: p<0.0001, naïve: p<0.0001, central/memory: p<0.0001); (CD8 subpopulations: Total: p<0.0001, naïve: p<0.0001, central/memory: p<0.0001). Results shown are means±SEM and are representative of two independent experiments. Significance was determined using 2-way ANOVA test.
Figure 12:
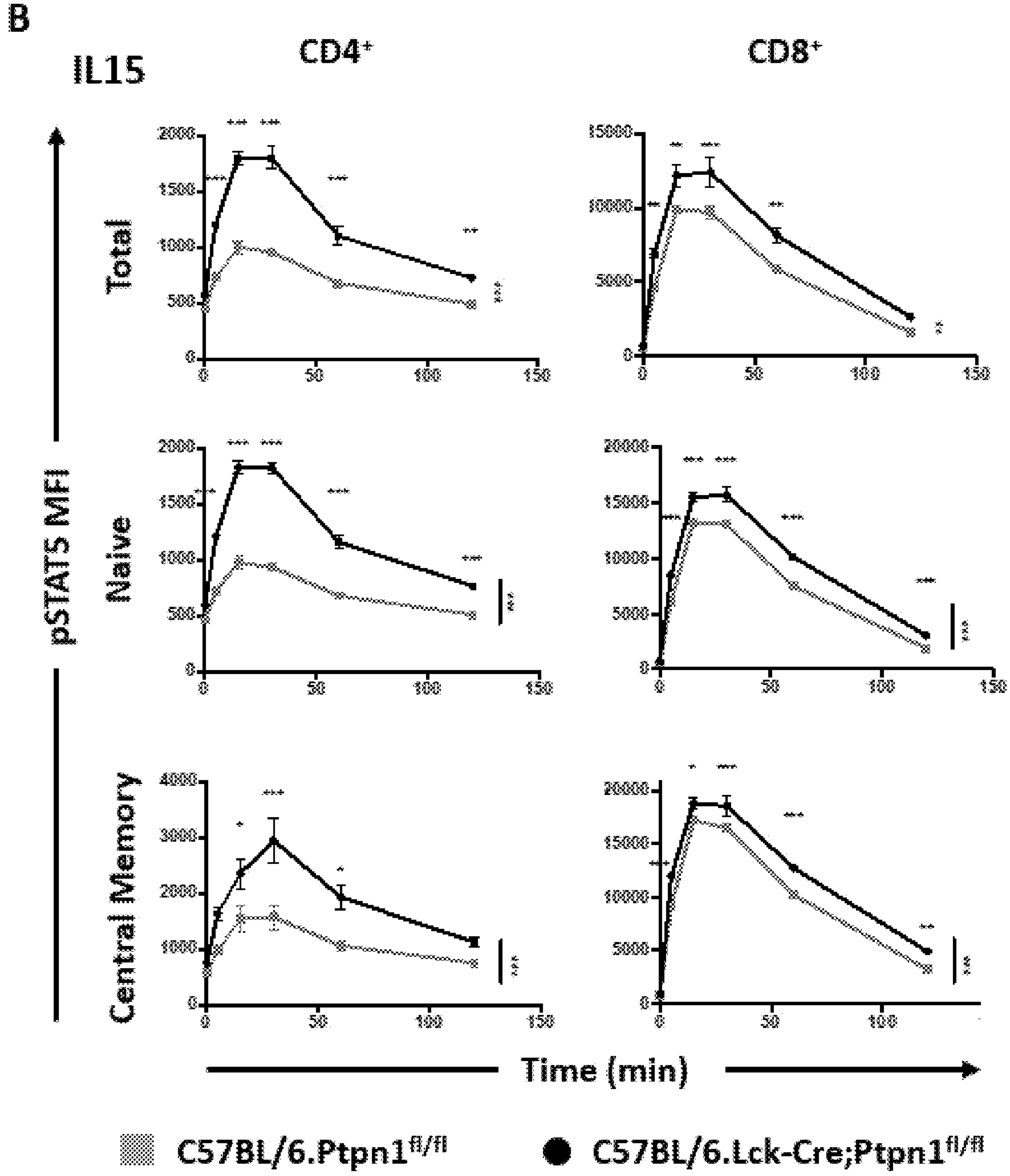

Lymphoid cells from Lck-Cre;Ptpn1$^{fl/fl}$ mice (n=5) and wild-type counter parts (n=5) were isolated and stimulated with either IL-7 (FIG. 12A) or IL-15 (FIG. 12B).

Phosphorylation of STAT5 was enhanced among overall CD4$^{+}$ and CD8+ T cells or naïve and central memory subpopulations. Statistics was performed with 2-way ANOVA analysis. Charts were representative from two independent experiments.

Example 5: Loss of Ptp1b Enhances Proliferation of T Cells

Figure 6:
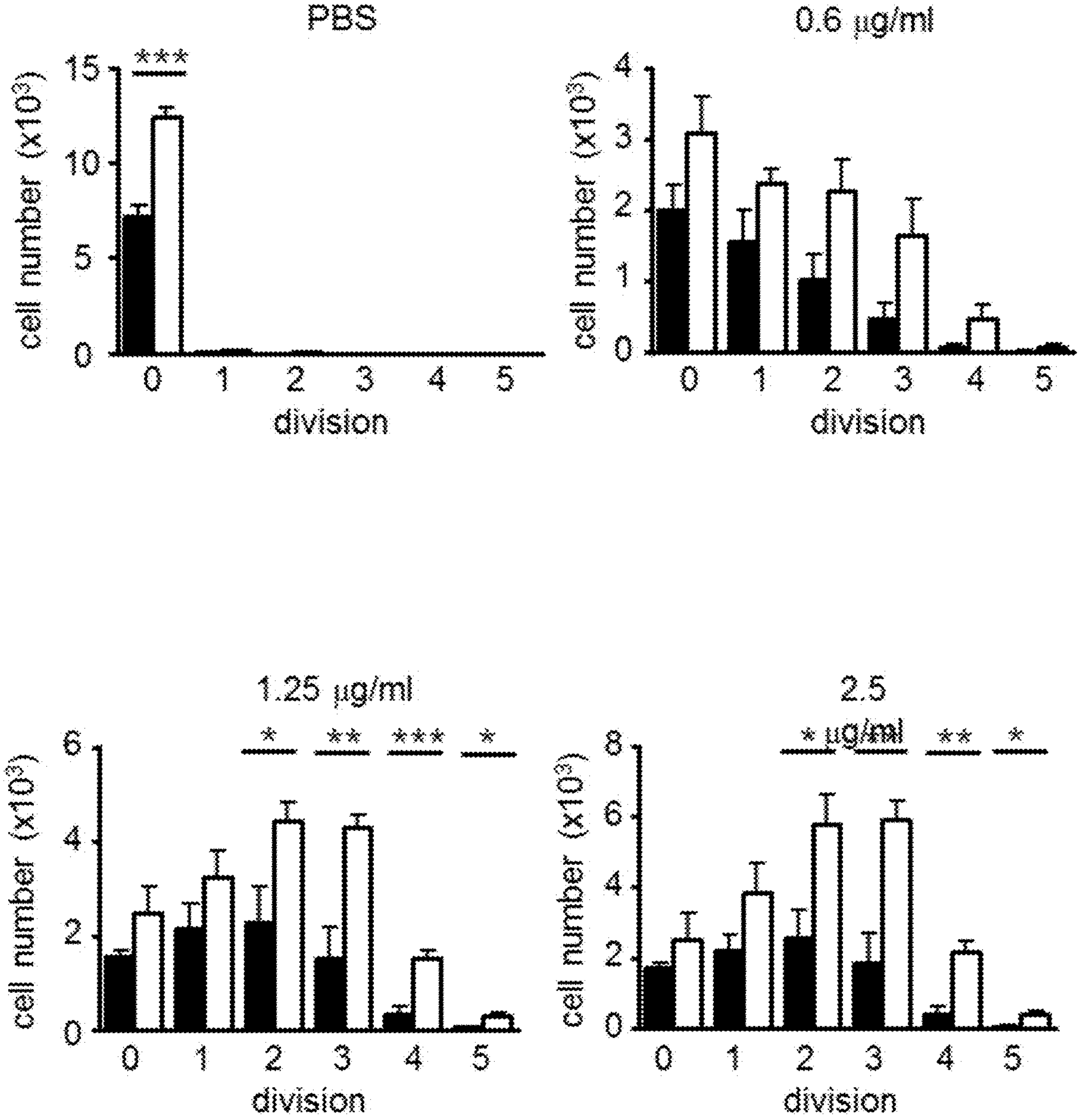
FIG. 6. PTP1B-deficiency enhances TCR-mediated CD4$^{+}$ naïve T cell proliferation in vitro. FACS-purified CD4$^{+}$ naïve (CD25$^{lo}$CD44$^{lo}$CD62L$^{hi}$) lymph node T cells from 7 week old C57BL/6.Ptpn1$^{+/+}$ and C57BL/6.Ptpn1$^{-/-}$ mice were stained with 2 μM Cell Tracker Violet (CTV) and stimulated with the indicated concentrations of plate bound α-CD3ε for 72 h and analysed by flow cytometry. Representative histogram overlays and quantified results for the indicated numbers of mice from two independent experiments are shown. Results shown are means±SEM; significances were determined using unpaired Student's t-test; *p<0.05, p<0.01, *p<0.001.
Figure 6:
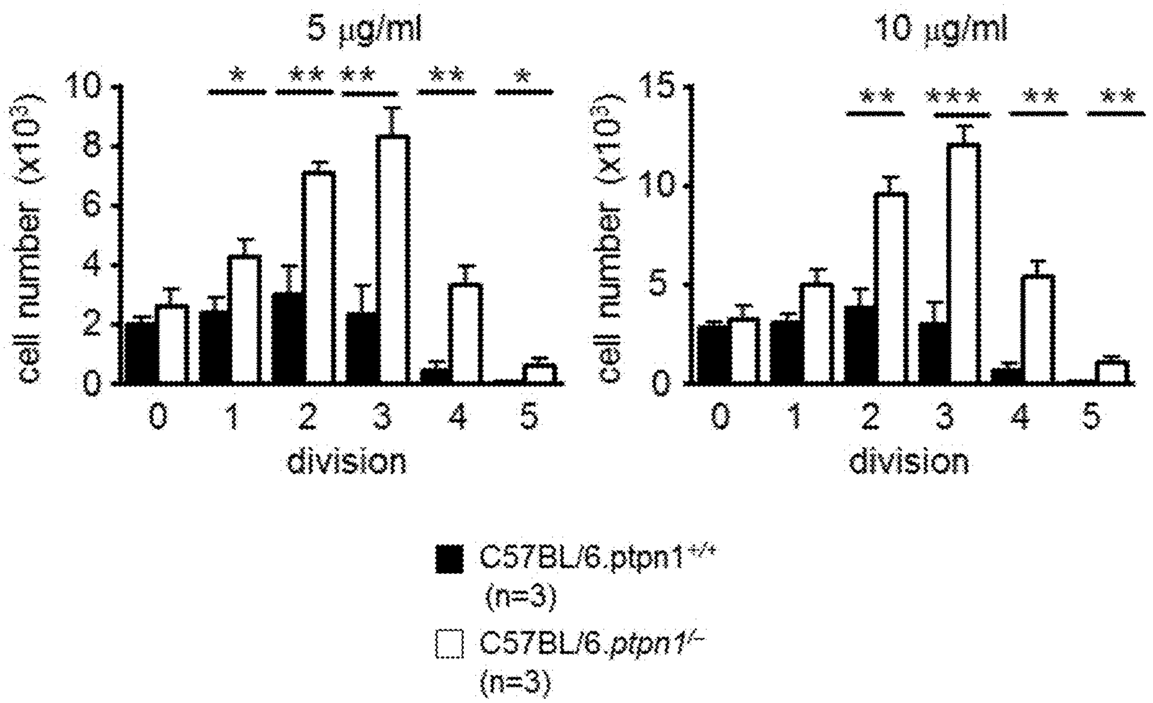
Figure 6:
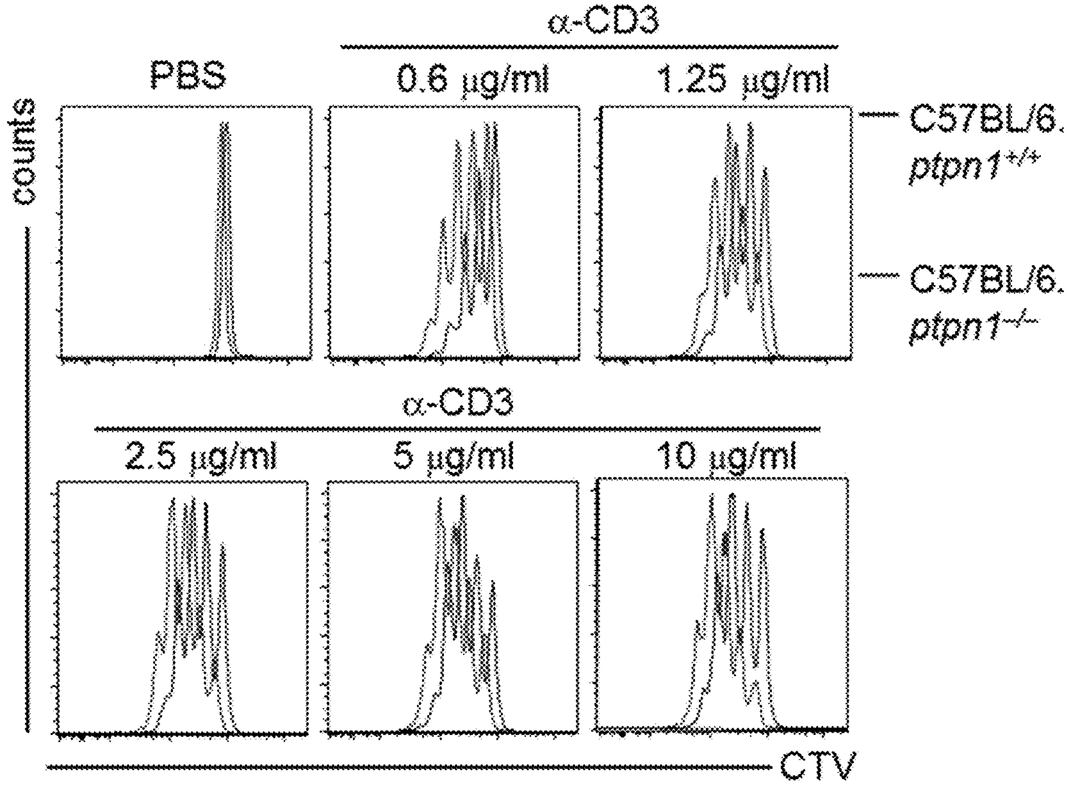
Figure 7:
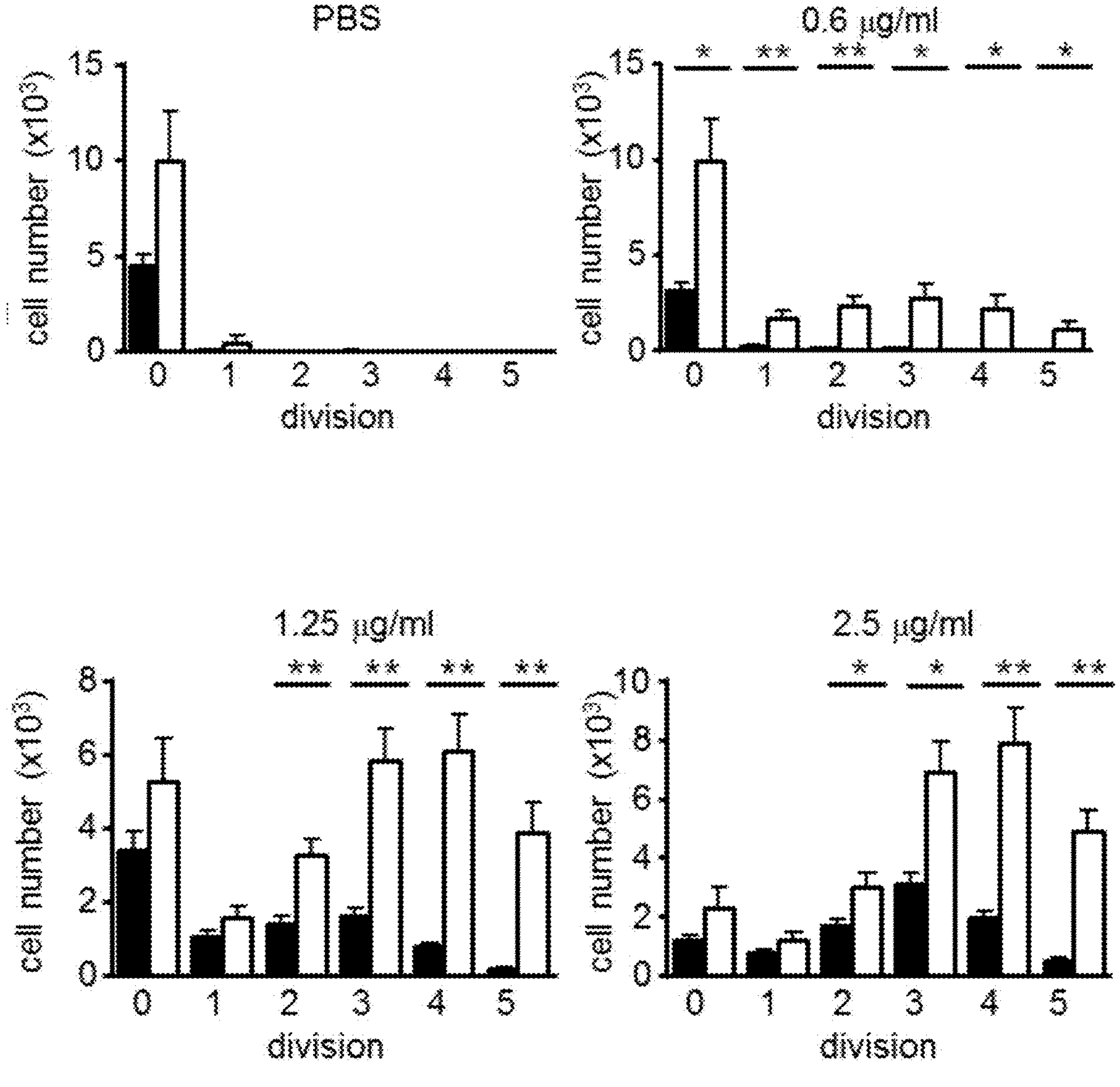
FIG. 7. PTP1B-deficiency enhances TCR-mediated CD8$^{+}$ naïve T cell proliferation in vitro. FACS-purified CD8$^{+}$ naïve (CD44$^{lo}$CD62L$^{hi}$) lymph node T cells (2××10$^{5}$) from 7 week old C57BL/6.Ptpn1$^{+/+}$ and C57BL/6.Ptpn1$^{-/-}$ mice were stained with 2 μM Cell Tracker Violet (CTV) and stimulated with the indicated concentrations of plate-bound α-CD3ε for 72 h and analysed by flow cytometry. Representative histogram overlays and quantified results for the indicated numbers of mice from two independent experiments are shown. Results shown are means±SEM; significances were determined using unpaired Student's t-test; *p<0.05, **p<0.01.
Figure 7:
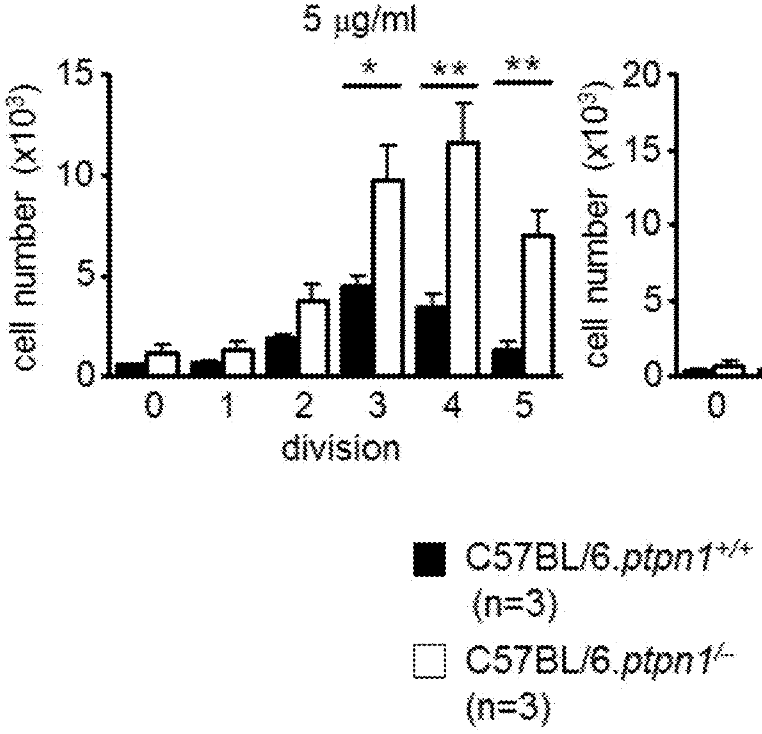
Figure 7:
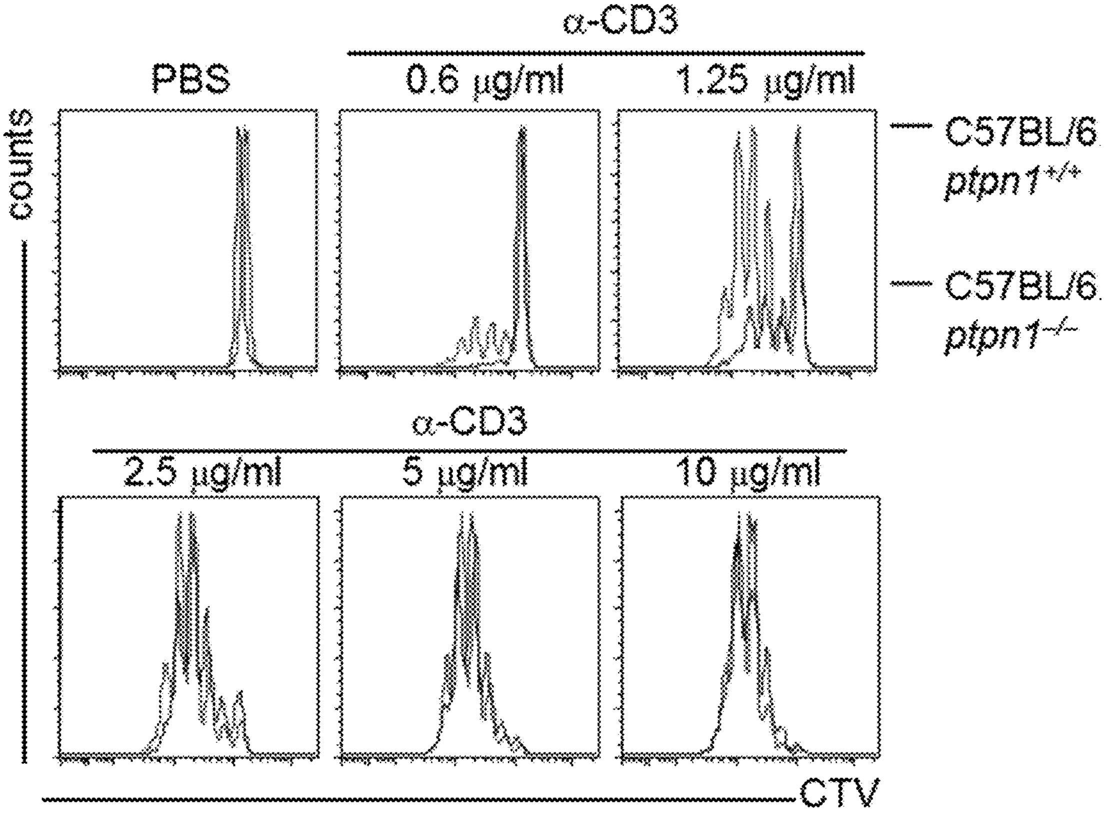
Figure 8:
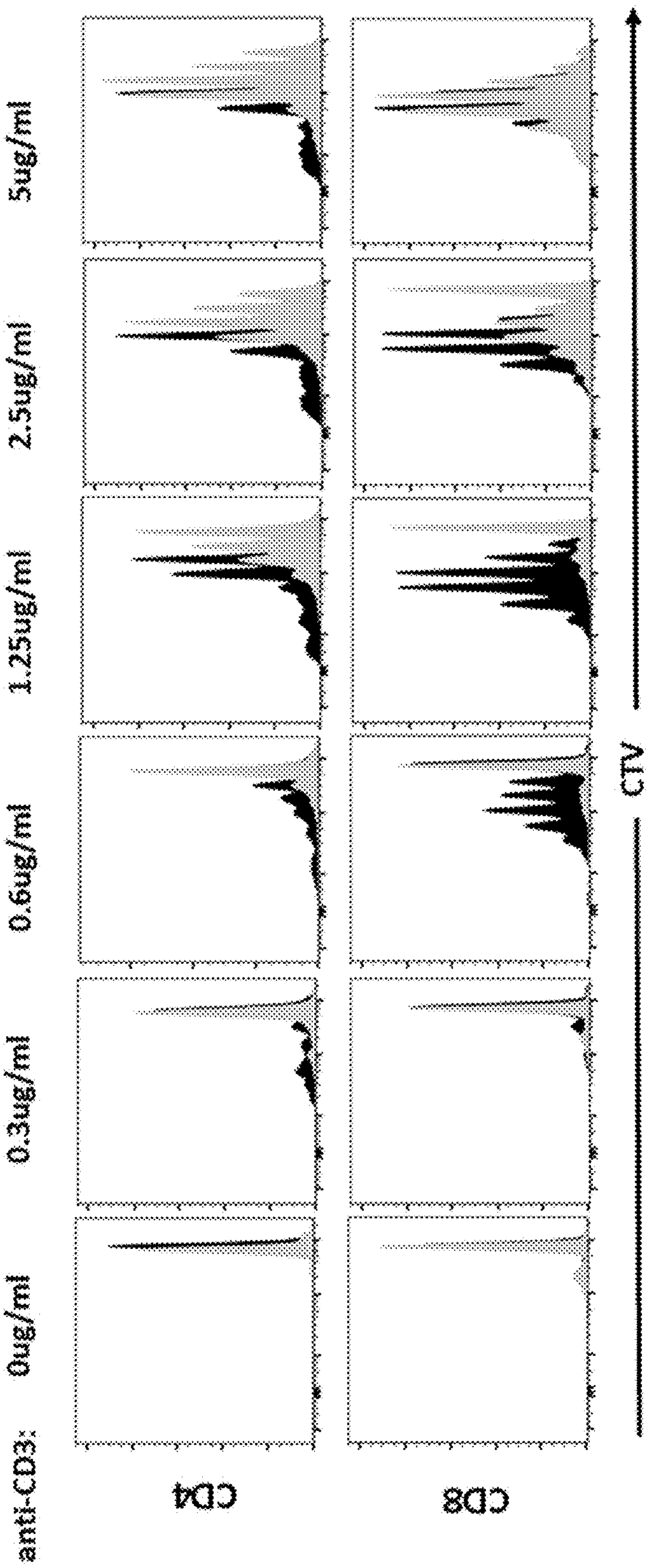
FIG. 8. T cell-specific PTP1B-deficiency enhances TCR-mediated proliferation. FACS-purified CD8$^{+}$ naïve (CD44$^{lo}$CD62L$^{hi}$) lymph lymph node T cells from C57BL/6.Lck-Cre;Ptpn1$^{fl/fl}$ (n=5) and C57BL/6.Ptpn1$^{fl/fl}$ mice (n=5) were stained with 2 μM CTV. Cells were stimulated with plate-bound α-CD3ε in serial 2-fold dilutions from 5 μg/ml to 0.3 μg/ml in the presence of 1.25 μg/ml soluble α-CD28 for 72 h and analyzed by flow cytometry. The numbers of proliferating C57BL/6.Lck-Cre;Ptpn1$^{fl/fl}$ CD4$^{+}$ (from 1.25 μg/ml to 5 μg/ml; p=0.369, p<0.0001, p<0.0001) or C57BL/6.Lck-Cre;Ptpn1$^{fl/fl}$ CD8$^{+}$ (from 1.25 μg/ml to 5 μg/ml; p=0.0005, p<0.0001, p<0.0001) T cells were significantly increased at various α-CD3 concentrations. Results shown are means±SEM and are representative of two independent experiments; significances were determined using 2-tailed Mann-Whitney U Test.
Figure 8:
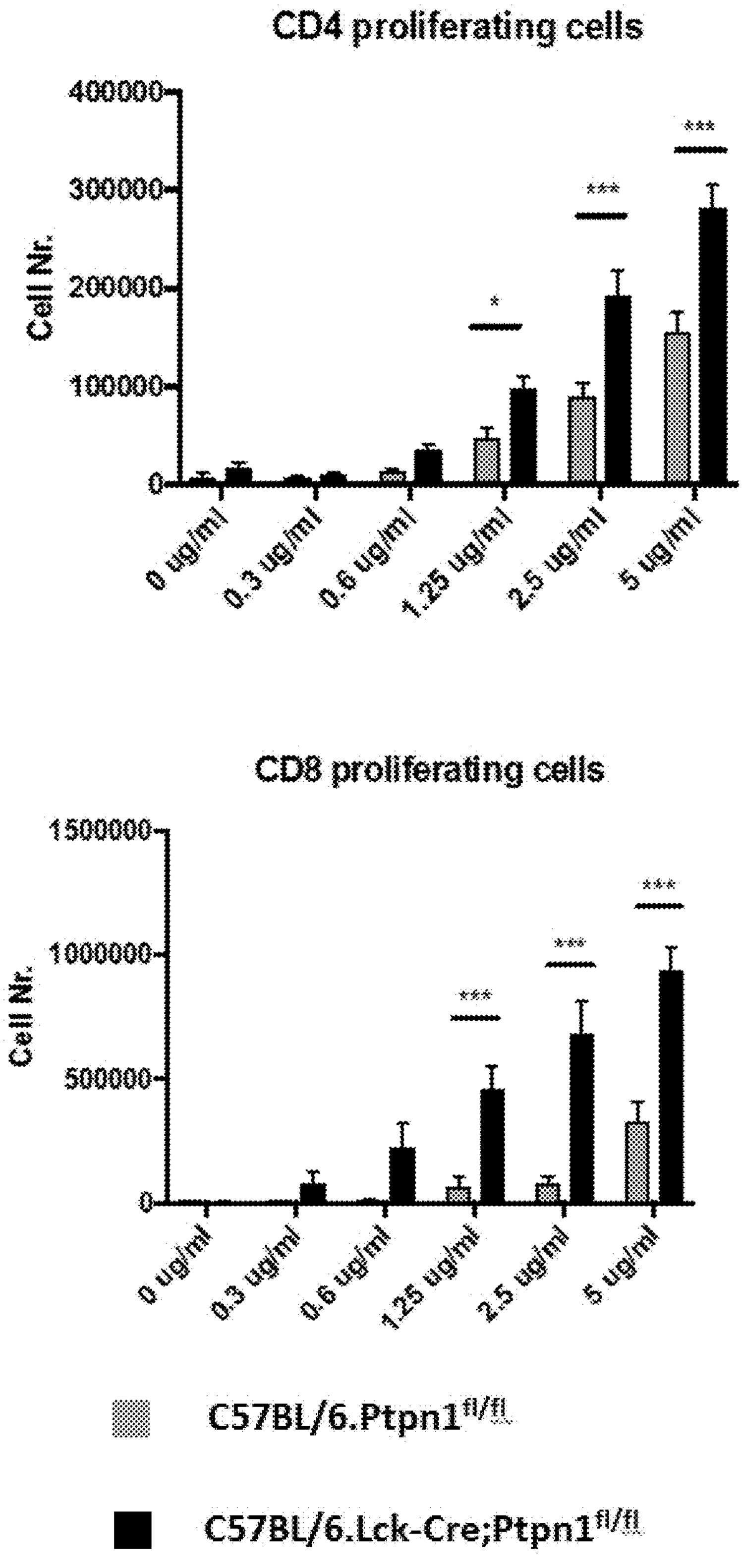
Figure 9:
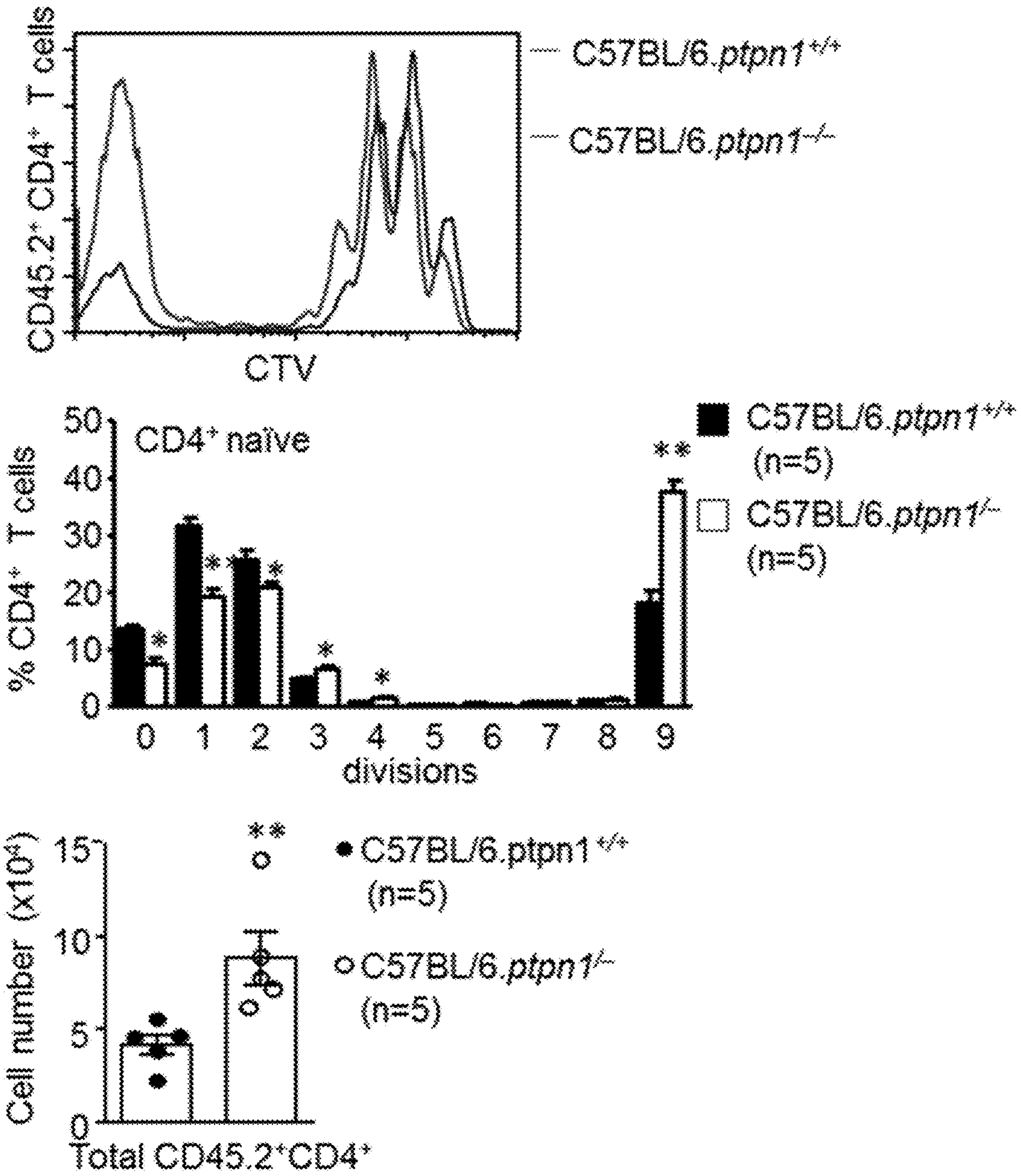
FIG. 9. PTP1B-deficiency enhances lymphopenia-induced proliferation in vivo. Naïve CD4$^{+}$ CD45.2$^{+}$ or CD8$^{+}$ CD45.2$^{+}$ lymph node T cells isolated from C57BL/6.Ptpn1$^{+/+}$ and C57BL/6.Ptpn1$^{-/-}$ mice were stained with CTV and transferred into sub-lethally irradiated (650 Gy) C57BL/6.Ly5.1/CD45.1+ hosts. At day 8 post adoptive transfer splenic T cells were stained with fluorochrome-conjugated antibodies against CD45.2, CD4 and CD8 and analyzed by flow cytometry. Representative CTV histogram overlays of CD45.2$^{+}$ CD8$^{+}$ donor T cells and quantified results (means±SEM) for the indicated numbers of mice from two independent experiments are shown. Significances was determined using 2-tailed Mann-Whitney U test; *P<0.05, **P<0.01.
Figure 9:
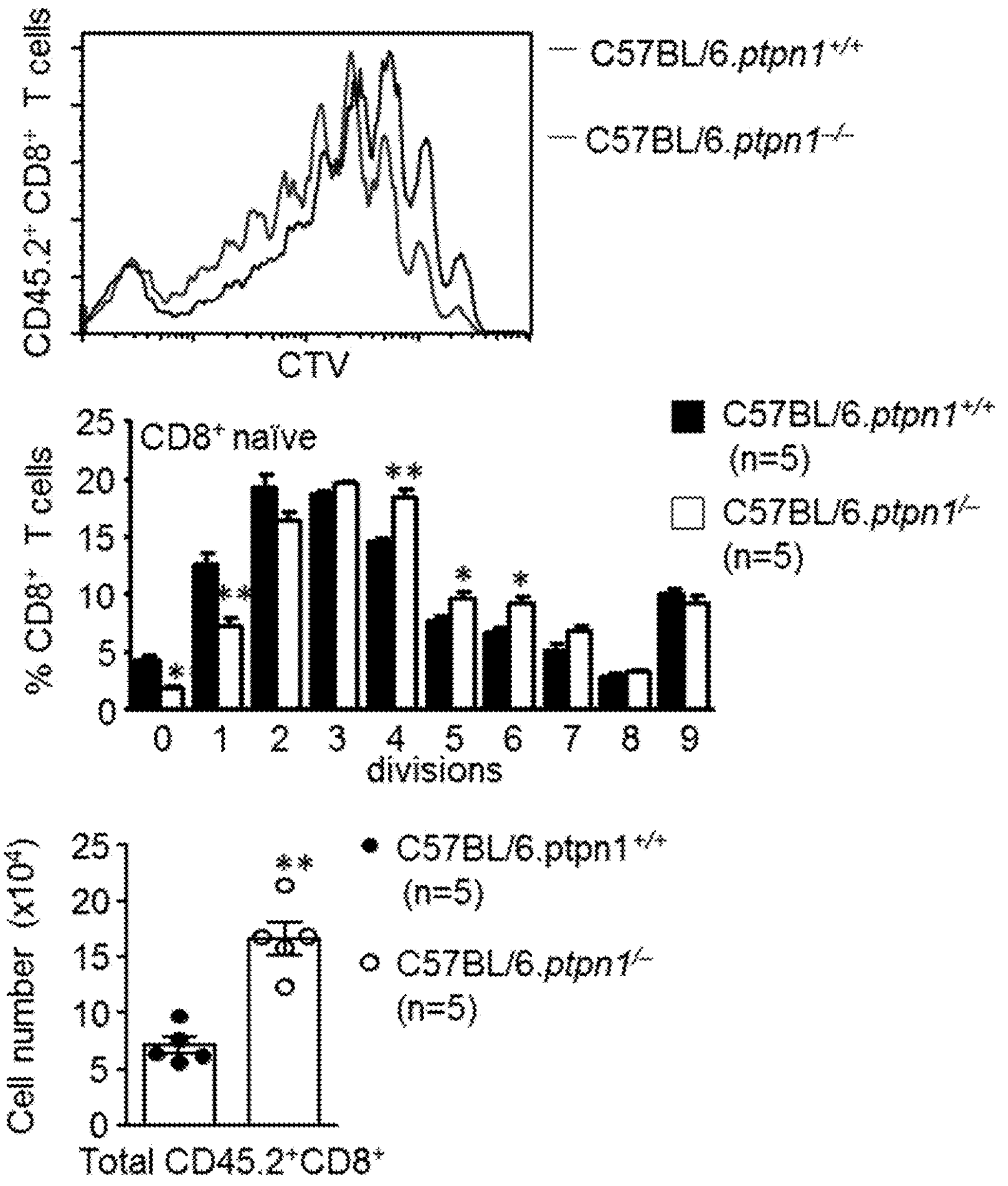
Figure 10:
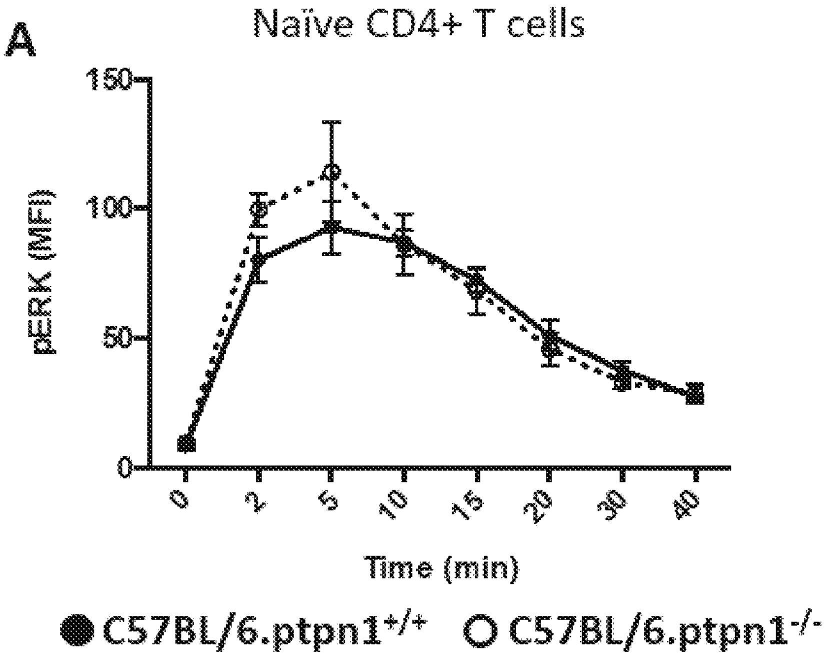
FIG. 10. PTP1B is not required for CD3-induced phosphorylation of ERK in naïve CD4$^{+}$ and CD8$^{+}$ T cells in vitro. CD4$^{+}$ A-B) and CD8$^{+}$ C-D) naïve (CD44$^{lo}$) and memory (CD44$^{hi}$) lymph node T cells (2×10$^{5}$) from 7 week old C57BL/6.Ptpn1$^{+/+}$ (n=4) and C57BL/6.Ptpn1$^{-/-}$ (n=4) mice were stained with 1 μg/ml soluble α-CD3ε for 30 minutes on ice and then incubated at 37° C. for the indicated time points. ERK phosphorylation was determined by flow cytometry and presented as mean fluorescence intensity (MFI). Results shown are means±SEM and are representative of two independent experiments.
Figure 10:
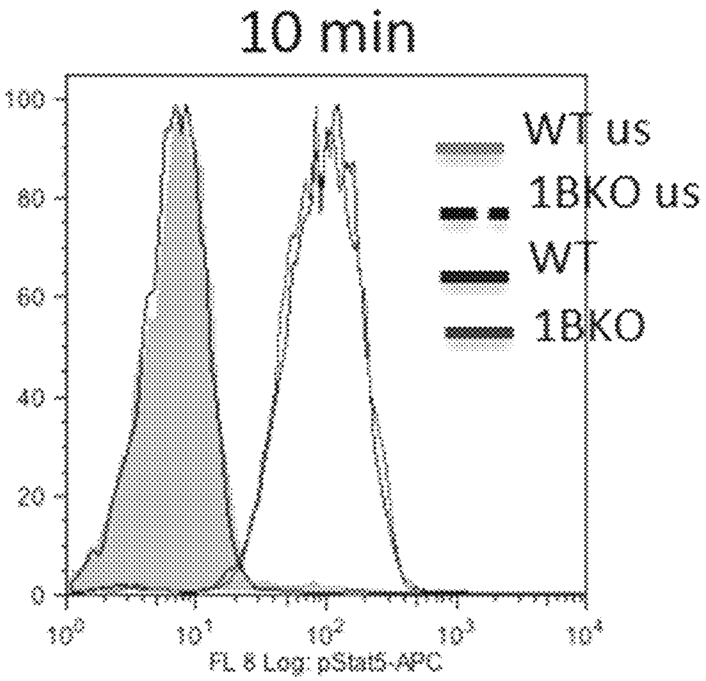
Figure 10:
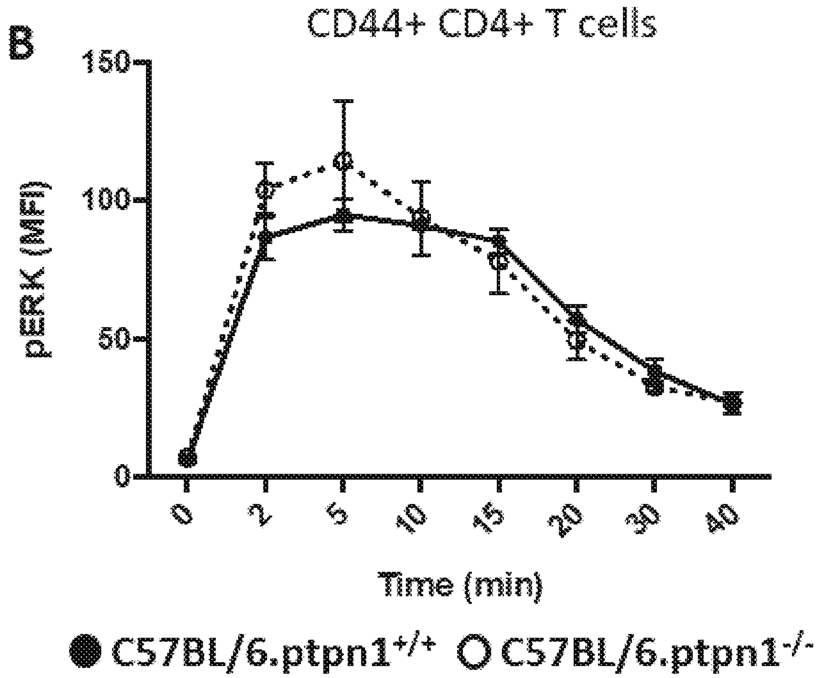
Figure 10:
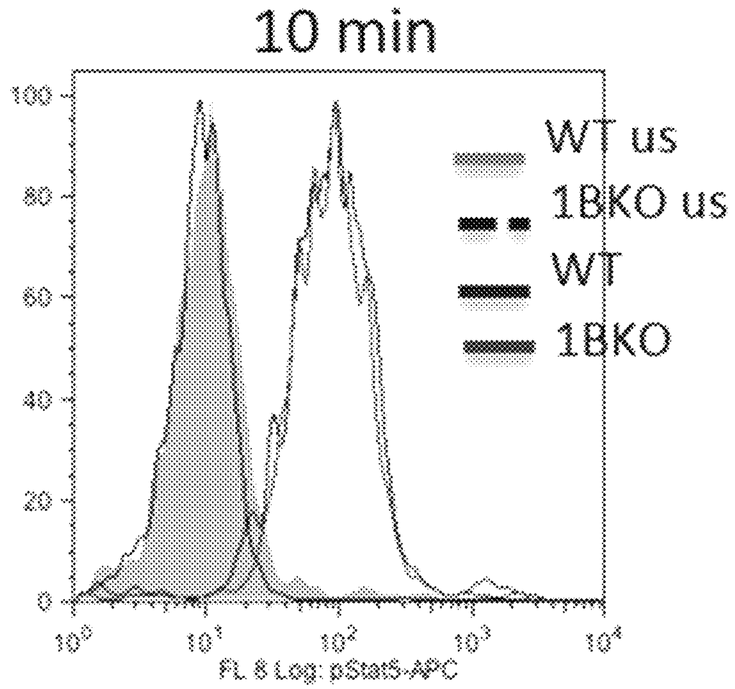
Figure 10:
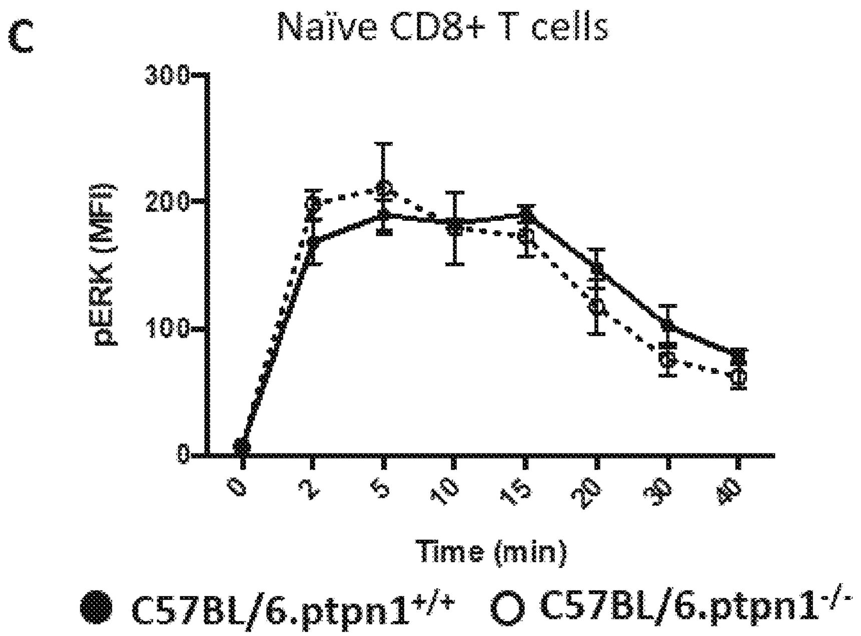
Figure 10:
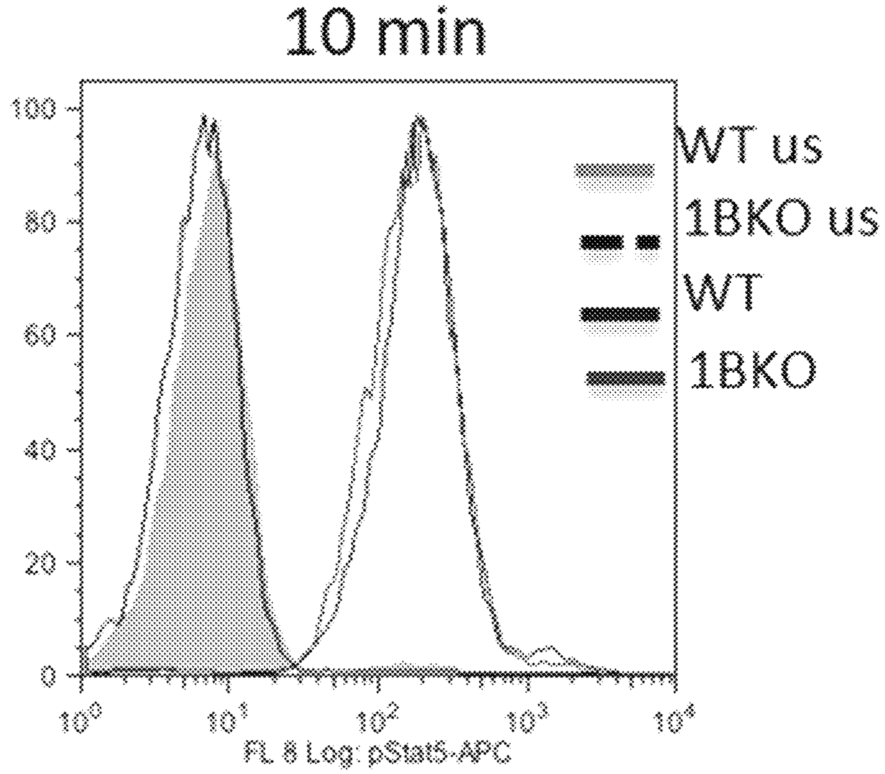
Figure 10:
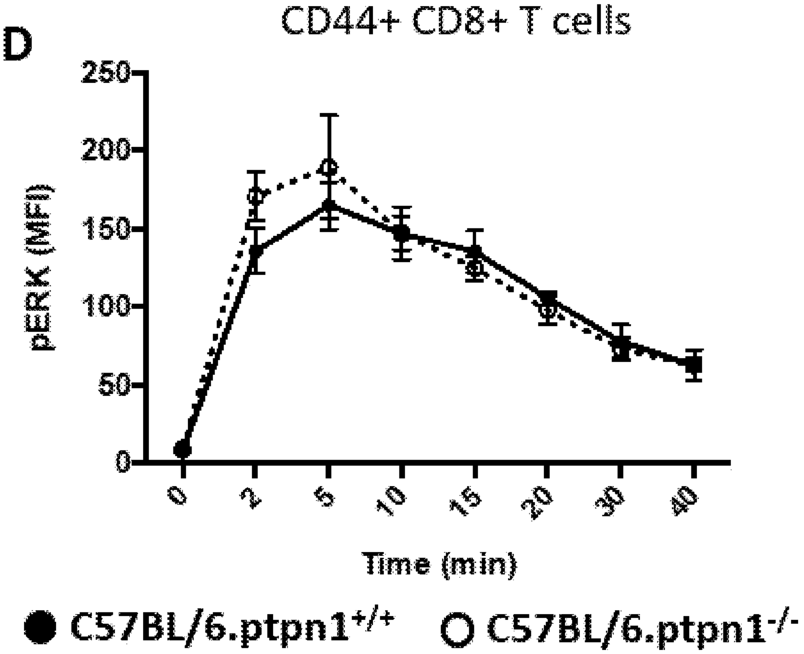
Figure 10:
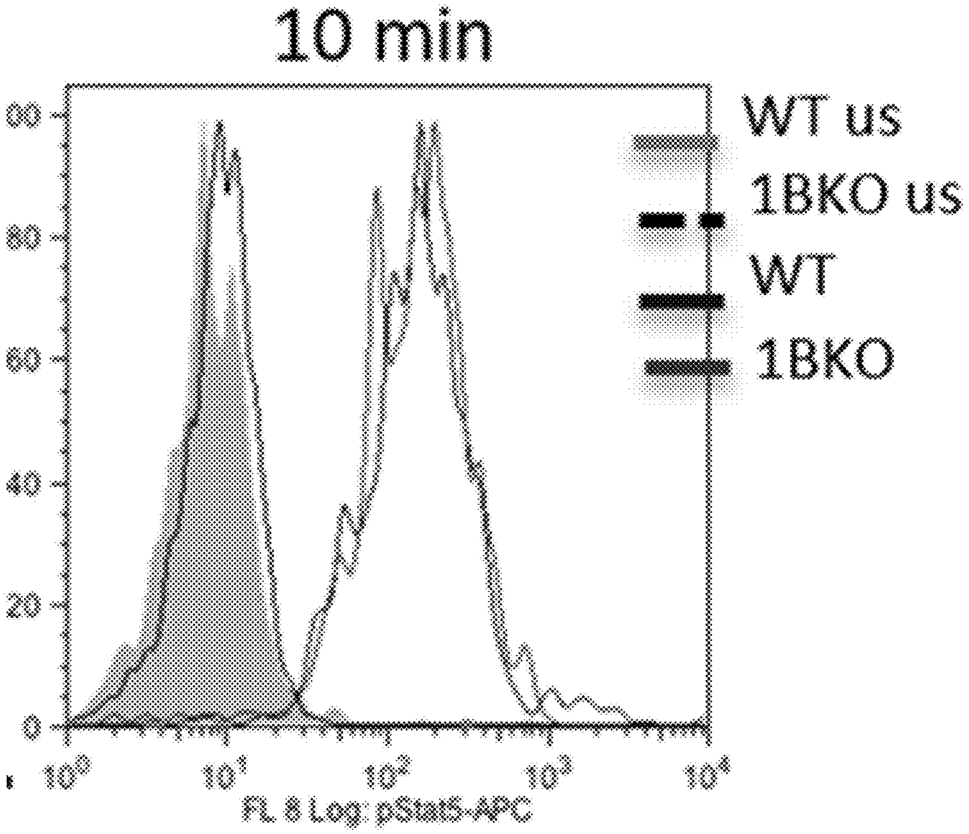
Figure 11:
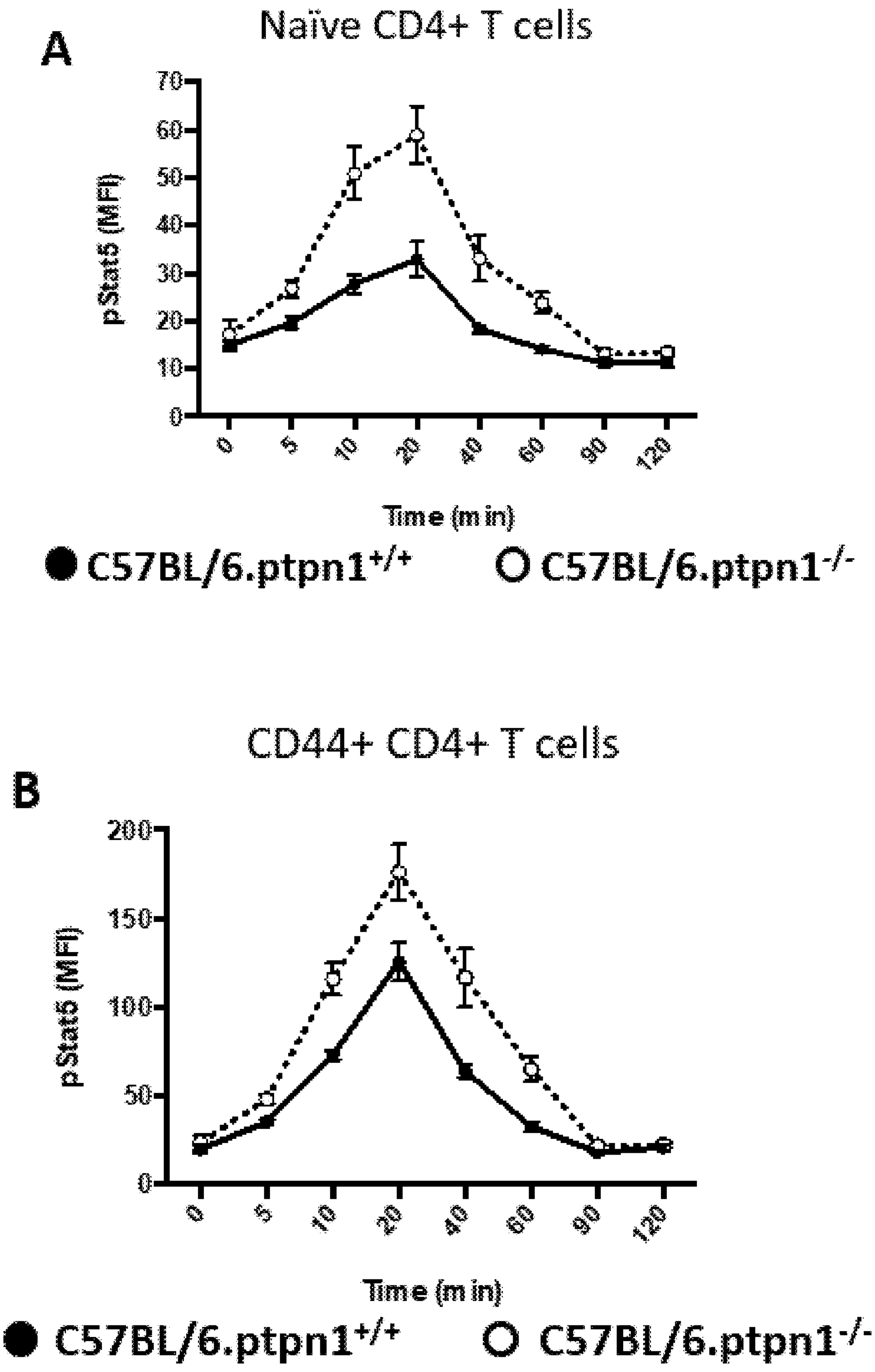
FIG. 11. Enhanced IL-15 induced Stat5 phosphorylation in CD4$^{+}$ and CD8$^{+}$ PTP1B-null T cells in vitro. CD4$^{+}$ and CD8$^{+}$ naïve (CD44$^{lo}$) and memory (CD44$^{hi}$) lymph node T cells (2×10$^{6}$) from 7 week old C57BL/6.Ptpn1$^{+/+}$ (n=4) and C57BL/6.Ptpn1$^{-/-}$ (n=4) mice were incubated with 5 ng/ml IL-15 for indicated time points at 37° C. Stat5 phosphorylation was determined by flow cytometry and presented as mean fluorescence intensity (MFI). Results shown are means±SEM and are representative of two independent experiments. Significance was determined using 2-way ANOVA test.
Figure 11:
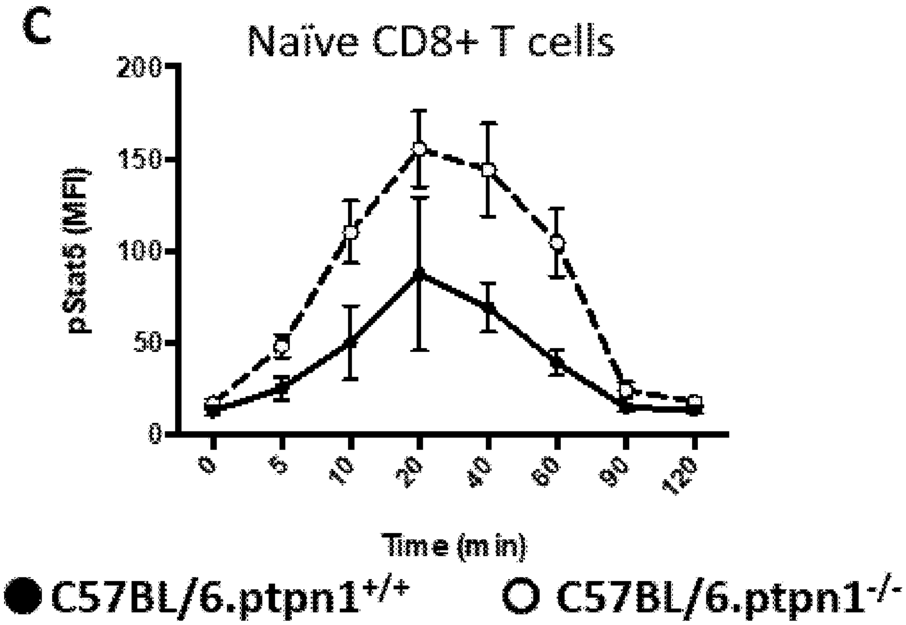
Figure 11:
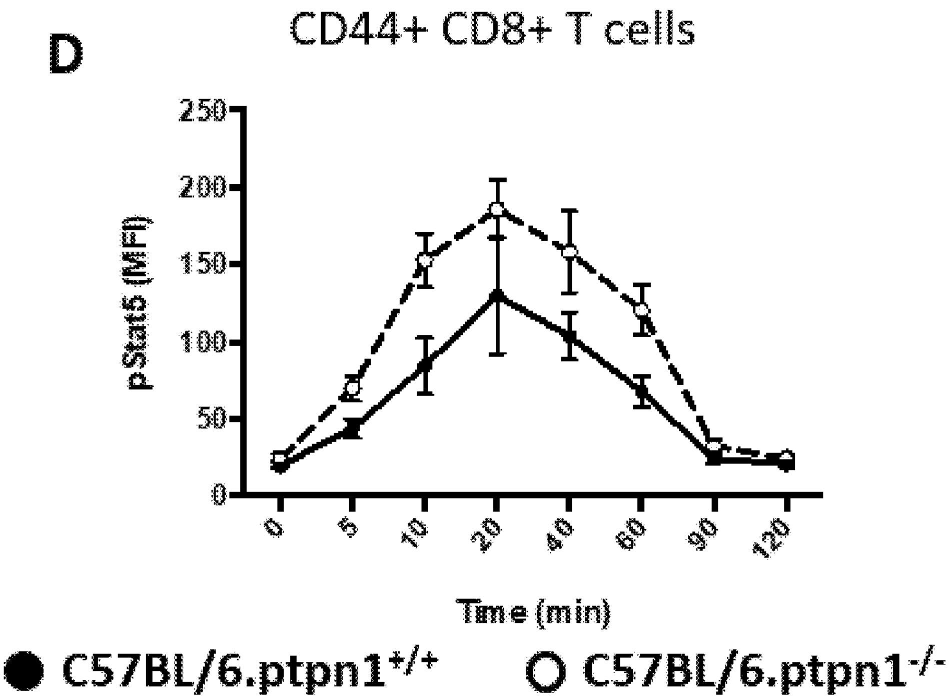

Lymphoid cells from Lck-Cre;Ptpn1$^{fl/fl}$ mice (n=5) and wild-type counter parts (n=5) were isolated and stimulated with various concentration of anti-CD3 and 1.25 μg/ml anti-CD28 antibodies for 72 hours. The proliferating cell numbers were significantly increased in CD4$^{+}$ T cells and CD8$^{+}$ T cells in various strength of anti-CD3 stimulation (see FIGS. 6-8).

Statistics was performed with Mann-Whitney test. Charts were representative from two independent experiments.

Example 6: Loss of Ptp1b Enhances the Killing Capacity of Chimeric Antigen Receptor (CAR) T Cells Splenic cells from Lck-Cre;Ptpn1$^{fl/fl}$ mice (n=5) and wild-type counter parts (n=5) were isolated and stimulated with 5 μg/ml anti-CD3 and 5 μg/ml anti-CD28 antibodies supplied with 5 ng/ml IL-2 and 0.2 ng/ml IL-7 on DO. Cells were then transduced twice with CAR-expressing vectors through retrovirus on D1 and D2. Transduced cells were then cultured with 5 ng/ml IL-2 and 0.2 ng/ml IL-7 in complete medium until D7 for the phenotype analysis and D10 for the killing assay.

CAR-T cells were co-cultured with target cells in different ratio for 4 hours before analysis. The Lck ptp1b CAR-T cells showed significantly better killing capacity in comparison to wild-type counter parts (FIG. 13A). When sorting out either central memory or effector/effector memory subpopulations before killing assay, in either subpopulations the Lck-Cre;Ptpn1$^{fl/fl}$ cells out compete the wild-type counterparts. In both genotypes, the effector/effector memory subpopulations performs better than the central memory populations in killing.

Figure 13:
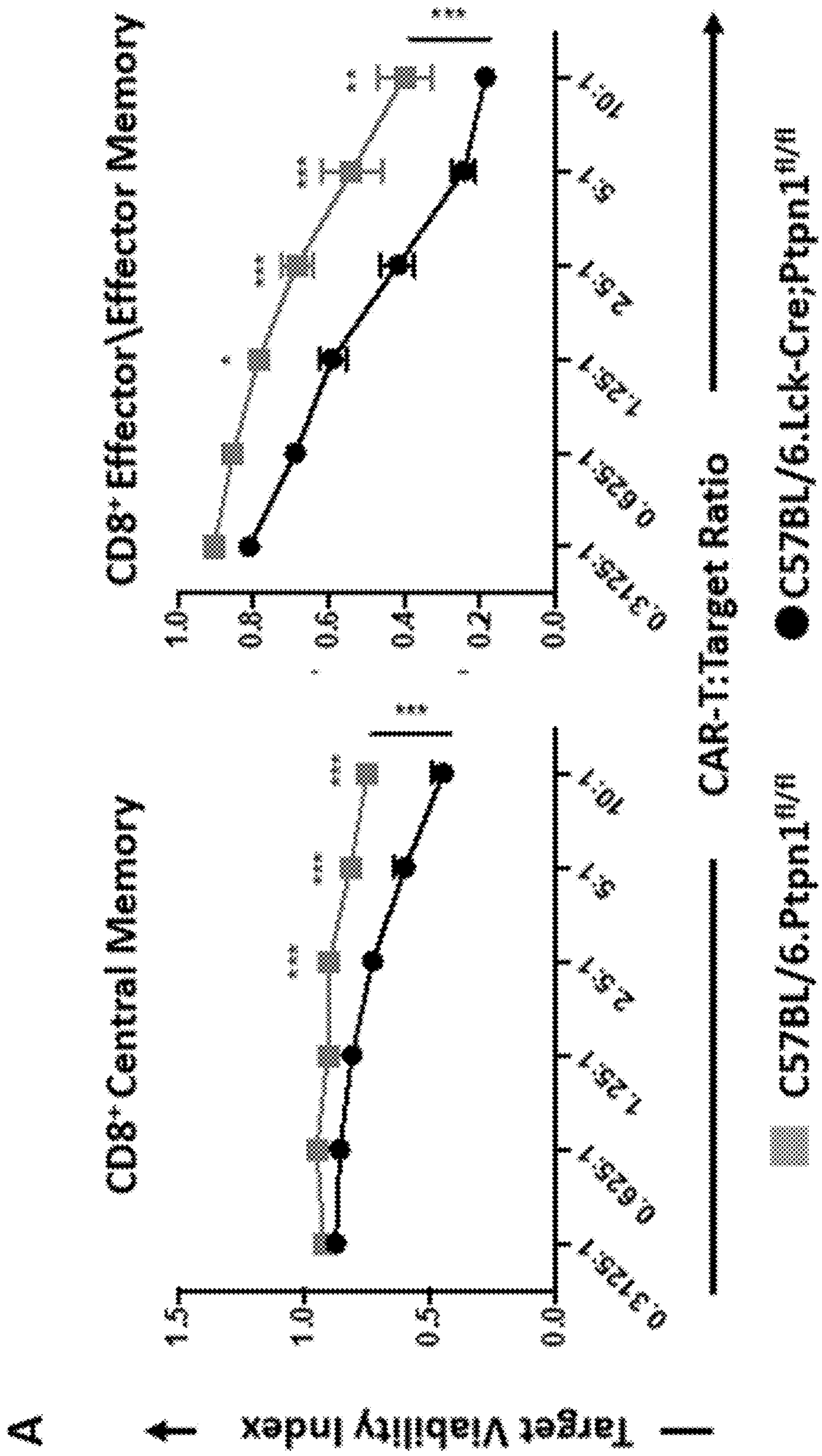
FIG. 13. PTP1B-deficiency enhances CAR T cell activation and cytotoxicity in vitro. Splenic cells from C57BL/6.Lck-Cre;Ptpn1$^{fl/fl}$ mice (n=5) and C57BL/6.Ptpn1$^{fl/fl}$ mice (n=5) were isolated and processed into single cells. $2.5\times10^7$ cells were stimulated with 5 μg/ml α-CD3 and 5 μg/ml α-CD28 antibodies supplemented with 5 ng/ml IL-2 and 0.2 ng/ml IL-7 on day 0. Cells were then transduced twice with a retrovirus carrying chimeric antigen receptor (CAR)-expressing vectors on day 1 and day 2. Transduced cells were then cultured with 5 ng/ml IL-2 and 0.2 ng/ml IL-7 in complete T cell medium for 7 days to assess CAR T cell phenotype and CAR T cell cytotoxicity. A) $CD8^+$ $CD44^+$ $CD62L^{hi}$ central memory and $CD8^+$ $CD44^+$ $CD62L^{lo}$ effector/effector memory CAR-T cells were sorted and then co-cultured with target cells in different CAR T:Target ratios for 4 hours. Target cells (HER-2 positive) were stained with 500 nM CTV and control cells (LML; HER-2 negative) were stained with 5 nM CTV. HER-2 positive target and HER-2 negative control cells were mixed 50:50 and co-cultured with CAR T cells. The Target Viability Index was calculated based on the cell numbers determined by flow cytometry and the following function.
Figure 13:
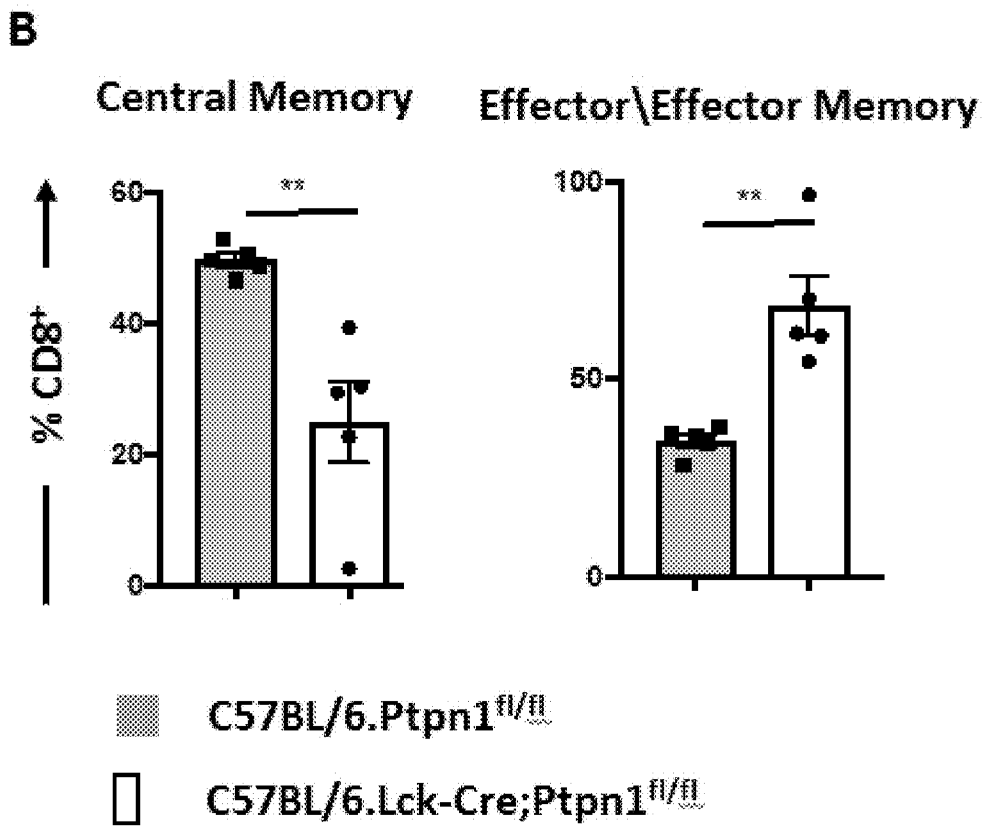
Figure 13:
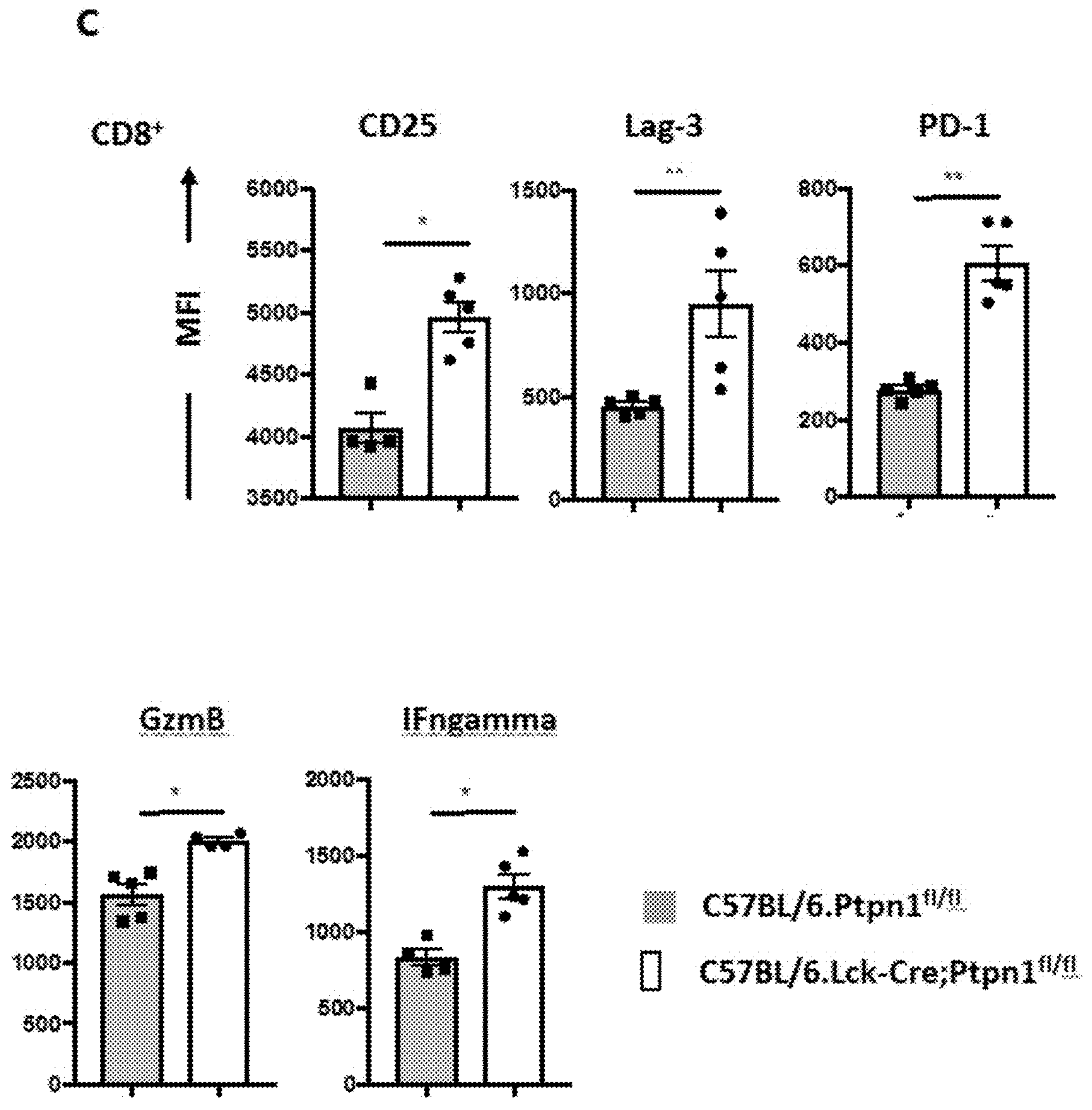

Loss of ptp1b leads to increased effector/effector memory subpopulations (FIG. 13).

The activation markers CD25, Lag3, and PD-1 were significantly increased the Lck-Cre;Ptpn1$^{fl/fl}$ CAR-T cells. Meanwhile, functional markers granzyme B and interferon gamma were also increased. (FIG. 13C).

Statistics was performed with 2-way ANOVA analysis in killing assay and with Mann-Whitney test for the phenotypes. Charts were representative from two independent experiments.

Example 7: Loss of Ptp1b Augments CAR-T Mediated Tumor Suppression and CAR-T Longevity CAR-T cells were manufactured as described above in Example 6.

2×10$^5$ Her-2 expressing E0771 cells were inoculated into mammary fat pad of Her-2 transgenic mice. CAR-T manufacturing was initiated simultaneously. 1×10$^7$ CAR-T cells were adoptively transferred i.v. along with and followed by 500 IU IL-2 for three times (FIG. 14A).

Tumor growth was monitored (FIG. 14B) and CAR-T cells were isolated from draining lymph nodes and spleens at the end point of tumor growth. Lck-Cre;Ptpn1$^{fl/fl}$ CAR-T cells performed significantly better suppression of tumor growth and were found to persist better in the mice (FIGS. 14C and D).

Statistics was performed with 2-way ANOVA for the tumor growth and with Mann-Whitney t-test for the cell numbers of CAR-T cells.

Example 8: Loss of Ptp1b Maintained CAR-T Cells with Less Exhausted Phenotypes

CAR-T cells were isolated from lymph nodes and spleens 20 days after being adoptively transferred into tumor bearing mice as described in Example 7.

The expression level of the exhaustion markers PD-1 and Lag-3 was analyzed with flow cytometry.

PD-1 expression level was significantly lower in Lck-Cre;Ptpn1$^{fl/fl}$ effector\effector memory CAR-T cells in draining lymph nodes (FIG. 15A). Lag-3 expression was lower in Lck-Cre;Ptpn1$^{fl/fl}$ central memory CAR-T cells in draining lymph nodes and spleens (FIG. 15B).

Statistics was performed with Mann-Whitney t-test.

Example 8: PTP1B Inhibition Represses Tumour Growth Via Action on T Cells

Breast cancer cells were transplanted into mammary fat pads of mice that were "globally" ptp1b-deficient (Ptpn1$^{-/-}$) or T-cell specific ptp1b-deficient (Lck-Cre;Ptpn1$^{fl/fl}$). Tumour growth was monitored for 28 days after transplantation. Mice that were globally deficient in ptp1b or heterozygous for ptp1b demonstrated significant suppression of tumour growth in comparison with controls (ptp1b+/+). (FIG. 18A). In T-cell specific ptp1b-deficient mice, tumour growth was significantly delayed and overall survival of tumour bearing mice was significantly improved compared to controls. (FIG. 19A). These results demonstrate that PTP1B deficiency in T cells enhances T cell-mediated immunosurveillances to repress the development of tumours.

The results presented in FIGS. 18-20 demonstrate that the growth of syngeneic tumours in mice is repressed if the mice are null for PTP1B (results in FIG. 18), or lack PTP1B in T cells only (see results in FIG. 19). Treatment of mice once every 3 days with the allosteric PTP1B inhibitor MS11436 (trudosquemine) also repressed the growth of the syngeneic mammary tumours (FIG. 20). Critically, the PTP1B inhibitor did not lead to further reductions in tumour burden in mice lacking PTP1B in T cells, which indicates that the PTP1B inhibitor elicits its anti-tumour effects by directly inhibiting PTP1B in T cells.

These results indicate that inhibition of PTP1B to elicit an anti-tumour effect can be accomplished either through direct inhibition of PTP1B in T cells prior to administration of the T cells to an individual, or alternatively by directly targeting PTP1B in T cells by direct administration of the inhibitor to the individual.

The invention claimed is:

1. A method for treating cancer in a subject in need thereof comprising administering a PTP1B inhibitor and CAR-T cell therapy to the subject, wherein the PTP1B inhibitor enhances activation of the CAR-T cells, thereby potentiating an immune response suitable for the treatment of cancer, wherein the PTP1B inhibitor is administered prior to or after administering the CAR-T cell therapy.

2. The method claim 1, wherein the cancer is a Her-2 positive cancer, a CD19 positive cancer, a CD171 positive cancer, an EGFR-positive cancer, a CD22-positive cancer, a CD123-positive cancer, a Lewis Y positive cancer cell, an MSLN-positive cancer, an FAP-positive cancer, or CD131-positive cancer.

3. The method of claim 1, wherein the PTP1B inhibitor is administered systemically or by any means that allows the PTP1B inhibitor to enter the circulation.

4. The method of claim 1, wherein the PTP1B inhibitor is a small molecule inhibitor selected from claramine or trodusquemine or derivatives thereof.

5. The method of claim 1, where the PTP1B inhibitor acts directly on the CAR-T cells.

6. The method of claim 1 where the method results in increased expansion and proliferation of the CAR-T cells, compared to a method where the PTP1B inhibitor is not administered.

7. The method of claim 1, wherein the method results in increased cell-killing capacity of the CAR-T cells, compared to a method where the PTP1B inhibitor is not administered.

* * * * *

SEQUENCE LISTING

```
<160> NUMBER OF SEQ ID NOS: 15

<210> SEQ ID NO 1
<211> LENGTH: 29
<212> TYPE: DNA
<213> ORGANISM: Artificial Sequence
<220> FEATURE:
<223> OTHER INFORMATION: synthetic

<400> SEQUENCE: 1
```

aattgcacca ggaagataat gactatatc 29

<210> SEQ ID NO 2
<211> LENGTH: 21
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (20)..(21)
<223> OTHER INFORMATION: n is deoxythymidine nucleotide (dT)

<400> SEQUENCE: 2
uagguacaga gacgucagun n 21

<210> SEQ ID NO 3
<211> LENGTH: 21
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (20)..(21)
<223> OTHER INFORMATION: n is deoxythymidine nucleotide (dT)

<400> SEQUENCE: 3
acugacgucu cuguaccuan n 21

<210> SEQ ID NO 4
<211> LENGTH: 21
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (20)..(21)
<223> OTHER INFORMATION: n is deoxythymidine nucleotide (dT)

<400> SEQUENCE: 4
uagguacaga gacgucagun n 21

<210> SEQ ID NO 5
<211> LENGTH: 21
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (20)..(21)
<223> OTHER INFORMATION: n is deoxythymidine nucleotide (dT)

<400> SEQUENCE: 5
acugacgucu cuguaccuan n 21

<210> SEQ ID NO 6
<211> LENGTH: 21
<212> TYPE: DNA
<213> ORGANISM: Artificial Sequence
<220> FEATURE:
<223> OTHER INFORMATION: synthetic

<400> SEQUENCE: 6
aaatcaacgg aagaagggtc t 21

<210> SEQ ID NO 7
<211> LENGTH: 21
<212> TYPE: RNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(2)
<223> OTHER INFORMATION: n is any nucleic acid

<400> SEQUENCE: 7
nnugaccaua gucggauuaa a 21

<210> SEQ ID NO 8
<211> LENGTH: 25
<212> TYPE: RNA
<213> ORGANISM: Artificial Sequence
<220> FEATURE:
<223> OTHER INFORMATION: synthetic

<400> SEQUENCE: 8
uugauguagu uuaauccgac uaugg 25

<210> SEQ ID NO 9
<211> LENGTH: 25
<212> TYPE: RNA
<213> ORGANISM: Artificial Sequence
<220> FEATURE:
<223> OTHER INFORMATION: synthetic

<400> SEQUENCE: 9
ccauagucgg auuaaacuac aucaa 25

<210> SEQ ID NO 10
<211> LENGTH: 20
<212> TYPE: DNA
<213> ORGANISM: Artificial Sequence
<220> FEATURE:
<223> OTHER INFORMATION: synthetic

<400> SEQUENCE: 10
ttcgagcaga tcgacaagtc 20

<210> SEQ ID NO 11
<211> LENGTH: 20
<212> TYPE: DNA
<213> ORGANISM: Artificial Sequence
<220> FEATURE:
<223> OTHER INFORMATION: synthetic

<400> SEQUENCE: 11
gatgtagttt aatccgacta 20

<210> SEQ ID NO 12
<211> LENGTH: 20
<212> TYPE: DNA
<213> ORGANISM: Artificial Sequence
<220> FEATURE:
<223> OTHER INFORMATION: synthetic

<400> SEQUENCE: 12
gagctgggcg gccatttacc 20

<210> SEQ ID NO 13
<211> LENGTH: 20

-continued

```
<212> TYPE: DNA
<213> ORGANISM: Artificial Sequence
<220> FEATURE:
<223> OTHER INFORMATION: synthetic

<400> SEQUENCE: 13

tgacgtctct gtacctattt                                              20


<210> SEQ ID NO 14
<211> LENGTH: 20
<212> TYPE: DNA
<213> ORGANISM: Artificial Sequence
<220> FEATURE:
<223> OTHER INFORMATION: synthetic

<400> SEQUENCE: 14

caaaagtgac cgcatgtgtt                                              20


<210> SEQ ID NO 15
<211> LENGTH: 20
<212> TYPE: DNA
<213> ORGANISM: Artificial Sequence
<220> FEATURE:
<223> OTHER INFORMATION: synthetic

<400> SEQUENCE: 15

gtctttcagt tgaccatagt                                              20
```